United States Patent
Holsboer et al.

(10) Patent No.: US 10,837,062 B2
(45) Date of Patent: *Nov. 17, 2020

(54) METHOD FOR PREDICTING A TREATMENT RESPONSE TO A CRHR1 ANTAGONIST AND/OR A V$_{1B}$ ANTAGONIST IN A PATIENT WITH DEPRESSIVE AND/OR ANXIETY SYMPTOMS

(71) Applicant: Max-Planck-Gesellschaft zur Förderung der Wissenschaften e.V., Munich (DE)

(72) Inventors: Florian Holsboer, Munich (DE); Bertram Müller-Myhsok, Munich (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,123

(22) Filed: Dec. 21, 2018

(65) Prior Publication Data

US 2019/0194752 A1 Jun. 27, 2019

Related U.S. Application Data

(63) Continuation of application No. 14/898,877, filed as application No. PCT/EP2014/062592 on Jun. 16, 2014, now Pat. No. 10,190,168.

(30) Foreign Application Priority Data

Jun. 17, 2013 (GB) .................................. 1310782.6

(51) Int. Cl.
| | | |
|---|---|---|
| C12Q 1/6883 | (2018.01) | |
| A61K 31/426 | (2006.01) | |
| A61K 31/44 | (2006.01) | |
| A61K 31/53 | (2006.01) | |

(52) U.S. Cl.
CPC .......... *C12Q 1/6883* (2013.01); *A61K 31/426* (2013.01); *A61K 31/44* (2013.01); *A61K 31/53* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,060,478 A | 5/2000 | Gilligan et al. | |
| 6,107,301 A | 8/2000 | Aldrich et al. | |
| 6,586,456 B1 | 7/2003 | Fontaine et al. | |
| 7,067,664 B1 | 6/2006 | Chen | |
| 8,420,679 B2 | 4/2013 | Fontaine et al. | |
| 10,190,168 B2 * | 1/2019 | Holsboer | A61K 31/426 |
| 2003/0092019 A1 | 5/2003 | Meyer et al. | |
| 2005/0069936 A1 | 3/2005 | Diamond et al. | |
| 2006/0240419 A1 | 10/2006 | Nakamura et al. | |
| 2007/0281919 A1 | 12/2007 | Fontaine et al. | |
| 2008/0118918 A1 | 5/2008 | Licinio et al. | |
| 2008/0194589 A1 | 8/2008 | Lanier et al. | |
| 2008/0318923 A1 | 12/2008 | Sekiguchi et al. | |
| 2009/0221009 A1 | 9/2009 | Bergmann et al. | |
| 2009/0306137 A1 | 12/2009 | Wolfgang et al. | |
| 2012/0115842 A1 | 5/2012 | Lubisch et al. | |
| 2012/0208195 A1 | 8/2012 | De Rijk et al. | |
| 2015/0094310 A1 | 4/2015 | Holsboer | |
| 2015/0150846 A1 | 6/2015 | Holsboer | |
| 2015/0278438 A1 | 10/2015 | Müller-Myhsok et al. | |
| 2016/0153043 A1 | 6/2016 | Holsboer et al. | |
| 2018/0042898 A1 | 2/2018 | Holsboer | |

FOREIGN PATENT DOCUMENTS

| | | | |
|---|---|---|---|
| EP | | 0773023 A1 | 5/1997 |
| EP | | 1659121 A1 | 5/2006 |
| JP | | H09-507249 A | 7/1997 |
| JP | | 2008-509674 A | 4/2008 |
| JP | | 2008-510151 A | 4/2008 |
| JP | | 2008-526702 A | 7/2008 |
| JP | | 2009-538331 A | 11/2009 |
| WO | WO 1994/013676 A1 | | 6/1994 |
| WO | WO 1995/033750 A1 | | 12/1995 |
| WO | WO 1996/009526 A1 | | 3/1996 |
| WO | WO 1997/029109 A1 | | 8/1997 |
| WO | WO 1998/003510 A1 | | 1/1998 |
| WO | WO 2001/005776 A1 | | 1/2001 |

(Continued)

OTHER PUBLICATIONS

Holsboer, "The rationale for corticotropin-releasing hormone receptor (CRH-R) antagonists to treat depression and anxiety," *J. Psychiatry Res.*, 33(3): 181-214 (1999).

Holsboer, "High-Quality Antidepressant Discovery by Understanding Stress Hormone Physiology," *Ann. N.Y. Acad. Sci.*, 1007: 394-404 (2003).

Holsboer, "How can we realize the promise of personalized antidepressant medicines?," *Nature Reviews Neuroscience*, 9: 638-646 (2008).

Rechtschaffen & Kales (Eds.), *A Manual of Standardized Terminology Techniques and Scoring System for Sleep Stages of Human Subjects*, BIS/BRI, UCLA, Los Angeles, 1968.

Japanese Patent Office, Notification of Reasons for Rejection in Japanese Patent Application No. 2016/520422 (dated Dec. 25, 2018).

U.S. Appl. No. 14/396,477, filed Oct. 23, 2014.

(Continued)

*Primary Examiner* — Jeffrey S Lundgren
*Assistant Examiner* — Michael J Schmitt
(74) *Attorney, Agent, or Firm* — Leydig, Voit & Mayer, Ltd.

(57) ABSTRACT

A method of treating a human patient with depressive and/or anxiety symptoms which includes administering an effective amount of a V1B receptor antagonist and/or CRHR1 antagonist to the patient in need thereof, wherein the patient's genome has certain polymorphoric variants.

10 Claims, 4 Drawing Sheets

Specification includes a Sequence Listing.

(56) References Cited

FOREIGN PATENT DOCUMENTS

| WO | WO 2002/072202 A1 | 9/2002 |
|---|---|---|
| WO | WO 2003/097877 A1 | 11/2003 |
| WO | WO 2004/047866 A2 | 6/2004 |
| WO | WO 2009/130232 A1 | 10/2004 |
| WO | WO 2004/094420 A1 | 11/2004 |
| WO | WO 2006/017854 A2 | 2/2006 |
| WO | WO 2006/044958 A1 | 4/2006 |
| WO | WO 2006/072458 A2 | 7/2006 |
| WO | 2006/080574 A1 | 8/2006 |
| WO | WO 2007/137227 A1 | 11/2007 |
| WO | WO 2008/080973 A1 | 7/2008 |
| WO | WO 2009/113985 A1 | 9/2009 |
| WO | WO 2013/160315 A2 | 10/2013 |
| WO | WO 2013/160317 A2 | 10/2013 |
| WO | WO 2013/186399 A1 | 12/2013 |

OTHER PUBLICATIONS

U.S. Appl. No. 14/396,617, filed Oct. 23, 2014.
U.S. Appl. No. 14/407,594, filed Dec. 12, 2014.
U.S. Appl. No. 14/898,877, filed Dec. 16, 2015.
U.S. Appl. No. 15/794,520, filed Oct. 26, 2017.
Ben-Efraim et al., "Family-Based Study of AVPR1B Association and Interaction with Stressful Life Events on Depression and Anxiety in Suicide Attempts," *Neuropsychopharmacology*, 38(8): 1504-1511 (2013).
Binneman et al., "A 6-Week Randomized, Placebo-Controlled Trial of CP-316,311 (a Selective $CRH_1$ Antagonist) in the Treatment of Major Depression," *Am. J. Psychiatry*, 165(5): 617-620 (2008).
Brenner et al., "Gene expression analysis by massively parallel signature sequencing (MPSS) on microbead arrays," *Nature Biotechnology*, 18: 630-634 (2000).
Broad Institute, "SNAP: SNP Annotation and Proxy Search," http:--www.broadinstitute.org-mpg-snap (downloaded Apr. 22, 2015).
Brouwer et al., "Prediction of treatment response by HPA-axis and glucocorticoid receptor polymorphisms in major depression," *Psychoneuroendocrinology*, 31(10): 1154-1163 (2006).
Budziszewska et al., "Regulation of the Human Coricotropin-Releasing-Hormone Gene Promoter Activity by Antidepressant Drugs in Neuro-2A and AtT-20 Cells," *Neuropsychopharmacology*, 29(4): 785-794 (2004).
Carlson et al., "Selecting a Maximally Informative Set of Single-Nucleotide Polymorphisms for Association Analyses Using Linkage Disequilibrium," *Am. J. Hum. Genet.*, 74(1): 106-120 (2004).
Carpenter et al., "Cerebrospinal Fluid Corticotropin-Releasing Factor and Perceived Early-Life Stress in Depressed Patients and Healthy Control Subjects," *Neuropsychopharmacology*, 29(4): 777-784 (2004).
Chen et al., "Synthesis and SAR of 2-Aryloxy-4-alkoxy-pyridines as Potent Orally Active Corticotropin-Releasing Factor 1 Receptor Antagonists," *Journal of Medicinal Chemistry*, 51(5): 1377-1384 (2008).
Coplan et al., "Persistent elevations of cerebrospinal fluid concentrations of corticotropin-releasing factor in adult nonhuman primates exposed to early-life stressors: Implications for the pathophysiology of mood and anxiety disorders," *Proc. Natl. Acad. Sci. USA*, 93(3): 1619-1623 (1996).
Coric et al., "Multicenter, Randomized, Double-Blind, Active Comparator and Placebo-Controlled Trial of a Corticotropin-Releasing Factor Receptor-1 Antagonist in Generalized Anxiety Disorder," *Depress Anxiety*, 27(5): 417-425 (2010).
Crisafulli et al., "Pharmacogenetics of Antidepressants," *Frontiers in Pharmacology*, 2: Article 6 [21 pages] (Feb. 16, 2011).
Dabla et al., "Co-peptin: Role as a novel biomarker in clinical practice," *Clinica Chimica Acta*, 412: 22-28 (2011).
Dempster, "Evidence of an Association Between the Vasopressin Vlb Receptor Gene (AVPRIB) and Childhood-Onset Mood Disorders," *Archives of General Psychiatry*, 64(10): 1189 (2007).

Devlin et al., "A Comparison of Linkage Disequilibrium Measures for Fine-Scale Mapping," *Genomics*, 29(2): 311-322 (1995).
Evaluatepharma, "Should Neurocrine get stressed over CFR1 failure" (Sep. 16, 2010) [obtained from internet at http:--www.evaluategroup.com-Universal-View.aspx?type=Story&id=224081&sectionID=&isEPVantage=yes].
Gabriel et al., "The Structure of Haplotype Blocks in the Human Genome," *Science*, 296(5576): 2225-2229 (2002).
Griebel et al., "Nonpeptide vasopressin $V_{1b}$ receptor antagonists as potential drugs for the treatment of stress-related disorders," *Curr. Pharm. Design*, 11: 1549-1559 (2005).
Griebel et al., "Neuropeptide receptor ligands as drugs for psychiatric diseases: the end of the beginning?," *Nature Reviews Drug Discovery*, 11(6): 462-478 (2012).
Griebel et al., "The Vasopressin V1b Receptor Antagonist SSR149415 I nthe Treatment of Major Depressive and Generalized Anxiety Disorders: Results from 4 Radomized, Double-Blind, Placebo-Controlled Studies," *J. Clin. Psychiatry*, 73(11): 1403-1411 (2012).
Griebel et al., "Anxiolytic- and antidepressant-like effects of the non-peptide vasopressin $V_{1b}$ receptor antagonist SSR149415, suggest an innovative approach for the treatment of stress-related disorders," *PNAS*, 99(9): 6370-6375 (2002).
Hamilton, "A Rating Scale For Depression," *J. Neurol. Neurosurg. Psychiat.*, 23(1): 56-62 (1960).
Heim et al., "The Dexamethasone-Corticotropin-Releasing Factor Test in Men with Major Depression: Role of Childhood Trauma," *Biol. Psychiatry*, 63(4): 398-405 (2008).
Hennings et al., "Clinical characteristics and treatment outcome in a representative sample of depressed inpatients—Findings from the Munich Antidepressant Response Signature (MARS) project," *Journal of Psychiatric Research*, 43: 215-229 (2009).
Heuser et al., "The Combined Dexamethasone-CRH Test: A Refined Laboratory Test for Psychiatric Disorders," *J. Psychiatr. Res.*, 28(4): 341-356 (1994).
Holsboer, "CNHR1 Antagonists as Novel Treatment Strategies," *CNS Spectrum*, 6(7): 590-594 (2001).
Ishizuka et al., "Involvement of vasopressin VI b receptor in anti-anxiety action of SSRI and SNRI in mice," *Neuroscience Research*, 66(3): 233-237 (2010).
Ising et al., "$CRH_1$ Receptor Antagonists for the Treatment of Depression and Anxiety," *Exp. Clin. Psychoparmacol.*, 15(6): 519-528 (2007).
Ising et al., "The combined dexamethasone-CRH test as a potential surrogate marker in depression," *Progress in Neuro-Psychopharmacology & Biological Psychiatry*, 29(6): 1085-1093 (2005).
Ising, "A Genomewide Association Study Points to Multiple Loci That Predict Antidepressant Drug Treatment Outcome in Depression," *Archives of General Psychiatry*, 66(9): 966-975 (2009).
Jüppner, "Functional Properties of the PTH-PTHHrP Receptor," *Bone*, 17(2): 39S-42S (1995).
Katan et al., "Copeptin, a stable peptide derived from the vasopressin precursor, correlates with the individual stress level," *Neuroendocrinol. Lett.*, 29(3): 341-346 (2008).
Keck et al., "Vasopressin Mediates the Response of the Combined Dexamethasone-CRH Test in Hyper-anxious Rats: Implications for Pathogenesis of Affective Disorders", *Neuropsychopharmacology*, 26(1): 94-105 (2002).
Keck et al., "Combined Effects of ExonicPolymorphisms in CRHR1 and AVPR1B Genes in a Case-Control Study for Panic Disorder," *American Journal of Medical Genetics Part B (Neuropsychiatric Genetics)*, 147B: 1196-1204 (2008).
Kimura et al., "Conditional corticotropin-releasing hormone overexpression in the mouse forebrain enhances rapid eye movement sleep," *Mol. Psychiatry*, 15(2): 154-165 (2010).
Künzel et al., "Pharmacological and Nonpharmacological Factors Influencing Hypothalamic-Pituitary-Adrenocortical Axis Reactivity in Acutely Depressed Psychiatric In-patients, Measured by the Dex-CRH Test," *Neuropsychopharmacology*, 28(12): 2169-78 (2003).
Landgraf, "The Involvement of the Vasopressin System in Stress-Related Disorders," *CNS & Neurological Disorders—Drug Targets*, 5: 167-179 (2006).
Leszczynska-Rodziewicz et al., "Association between functional polymorphism of the AVPRIb gene and polymorphism rs1293651

(56) References Cited

OTHER PUBLICATIONS of the CRHR1 gene and bipolar disorder with psychotic features," *Journal Of Affective Disorders*, 138(3): 490-493 (2012).
Licinio et al., "Association of a corticotropin-releasing hormone receptor 1 haplotype and antidepressant treatment response in Mexican-Americans," *Molecular Psychiatry*, 9(12): 1075-1082 (2004).
Liu et al., "Association of corticotropin-releasing hormone receptor1 gene SNP and haplotype with major depression," *Neuroscience Letters*, 484(3): 358-362 (2006).
Liu et al., "Association study of corticotropin-releasing hormone receptor 1 gene polymorphisms and antidepressant response in major depressive disorders," *Neuroscience Letters*, 414(2): 155-158 (2007).
Mardis, "Next-Generation DNA Sequencing Methods," *Annual Review of Genomics and Human Genetics*, 9: 387-402 (2008).
Max Planck Institute of Psychiatry, "Mars—The Munich Antidepressant Response Signature Project," www.mars-depression.de (downloaded Apr. 22, 2015).
Moore et al., "Molecular Diagnostics for the Clinical Laboratorian," William B. Coleman and Gregory J. Tsongalis, Editors, Humana Press (2007).
Morgenthaler et al., "Assay for the Measurement of Copeptin, a Stable Peptide Derived from the Precursor of Vasopressin," *Clin. Chem.*, 52(1): 112-119 (2006).
Müller et al., "Limbic corticotropin-releasing hormone receptor 1 mediates anxiety-related behavior and hormonal adaptation to stress," *Nat. Neurosci.*, 6(10): 1100-1107 (2003).
Murgatroyd et al., "Dynamic DNA methylation programs persistent adverse effects of early-life stress", *Nature Neuroscience*, 12(12): 1559-1566 (2009).
Nemeroff et al., "Elevated concentrations of CSF corticotropin-releasing factor-like immunoreactivity in depressed patients," *Science*, 226(4680): 1342-1344 (1984).
Nemeroff et al., "Reduced Corticotropin Releasing Factor Binding Sites in the Frontal Cortex of Suicide Victims," *Arch. Gen. Psychiatry*, 145(6): 577-579 (1988).
Nickel et al., "The role of copeptin as a diagnostic and prognostic biomarker for risk stratification in the emergency department," *BMC Medicine*, 10(1): 7 (2012).
Oost et al., "Potent and selective oxindole-based vasopressin 1b receptor antagonists with improved pharmacokinetic properties," *Biorg. Med. Chem. Lett.*, 21: 3828-3831 (2011).
Overstreet et al., "Antidepressant-like effects of the vasopressin V1b receptor antagonist SSR149415 in the Flinders Sensitive Line rat", *Pharmacology, Biochemistry and Behavior*, 82: 223-227 (2005).
Paez-Pereda et al., "Corticotropin releasing factor receptor antagonists for major depressive disorder," *Expert Opin. Investig. Drugs*, 20(4): 519-35 (2011).
Purba et al., "Increased Number of vasopressin- and oxytocin-expressing neurons in the paraventricular nucleus of the hypothalamus in depression," *Arch Gen Psychiatry*, 53(2): 137-143 (1996).
Ripke et al., "A mega-analysis of genome-wide association studies for major depressive disorder," *Molecular Psychiatry*, 18(4): 497-511 (2012).
Roberts, Stuart (Analyst, Southern Cross Equities), "Bionomics (BNO): Anxiety can be a good thing," pp. 1-37 (Apr. 11, 2011) [obtained from internet at http:--www.bionomics.com.au-siteFiles-files-Sourthern%20Cross%20Equities%20-%2011Apr11.pdf].
Sánchez et al., "Early adverse experience as a developmental risk factor for later psychopathology: Evidence from rodent and primate models," *Dev. Psychopathol.*, 13(3): 419-49 (2001).
Schüle et al., "The Combine Dexamethasone-CRH Test (DEX-CRH Test) and Prediction of Acute Treatment Response in Major Depression," *PLoS ONE*, 4(1): e4324 (2009).
Schuster, "Next-generation sequencing transforms today's biology," *Nature Methods*, 5(1): 16-18 (2008).
Serradeil-Le Gal et al., "Characterization of (2S,4R)-1-[5-Chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide (SSR149415), a Selective and Orally Active Vasopressin $V_{1b}$ Receptor Antagonist," *JPET*, 300(3): 1122-1130 (2002).
Spencer et al., "Designing Genome-Wide Association Studies: Sample Size, Power, Imputation, and the Choice of Genotyping Chip," *PLOS Genetics*, 5(5): e100047715 (2009).
Stoyanovich, "MutaGeneSys: estimating individual disease susceptibility based on genome-wide SNP array data," *Bioinformatics*, 24(3): 440-442 (2008).
Szymczak et al., "Machine Learning in Genome-Wide Association Studies," *Genetic Epidemiology*, 33(Supplement 1): S51-S57 (2009).
Thode et al., "Hypothalamic-pituitary-adrenal axis activation in response to stress is moderated by polymorphic variants within the corticotropin-releasing hormone receptor 1," *Biological Psychiatry*, 63(7-Suppl. S): 85S (2008).
Thode et al., "Hypothalamic-pituitary-adrenal axis activation in response to stress is moderated by polymorphic variants within the corticotropin-releasing hormone receptor 1," 63rd Annual Convention of the Society-of-Biological-Psychiatry, Washington, DC, USA (2008) [poster presentation retrieved from internet at http:--psychiatry.uthscsa.edu-RRTrack-images-Thode_Poster_08.pdf].
Timpl et al., "Impaired stress response and reduced anxiety in mice lacking a functional corticotropin-releasing hormone receptor 1," *Nature Genetics*, 19(2): 162-166 (1998).
Trivedi et al., "Evaluation of Outcomes With Citalopram for Depression Using Measurement-Based Care in STAR*D: Implications for Clinical Practice," *Am. J. Psychiatry*, 163(1): 28-40 (2006).
Tyrka et al., "Interaction of Childhood Maltreatment with the Corticotropin-Releasing Hormone Receptor Gene: Effects on Hypothalamic-Pituitary-Adrenal Axis Reactivity," *Biological Psychiatry*, 66(7): 681-685 (2009).
Uhr et al., "Polymorphisms in the Drug Transporter Gene ABCB1 Predict Antidepressant Treatment Response in Depression," *Neuron*, 57(2): 203-209 (2008).
Van Rossum et al., "Polymorphisms of the Glucocorticoid Receptor Gene and Major Depression," *Biological Psychiatry*, 59(8): 681-688 (2006).
Van West et al., "A major SNP haplotype of the arginine vasopressin IB receptor protects against recurrent major depression," *Molecular Psychiatry*, 9(3): 287-292 (2004).
Van West et al., "P.7.b.005 Arginine vasopressin receptor gene-based single nucleotide polymorphism (SNP) analysis in ADHD," *European Neuropsychopharmacology*, Elsevier Science Publishers BV, Amsterdam, NL, 19: 5686 (2009).
Van West et al., "Arginine vasopressin receptor gene-based single-nucleotide polymorphism analysis in attention deficit hyperactivity disorder", *Psychiatric Genetics*, 19: 102-103 (2009).
Van West et al., "Associations between common arginine vasopressin lb receptor and glucocorticoid receptor gene variants and HPA axis responses to psychosocial stress in a child psychiatric population," *Psychiatry Research*, 179(1): 64-68 (2010).
Zobel et al., "Effects of the high-affinity corticotrophin-releasing hormone receptor 1 antagonist R121919 in major depression: the first 10 patients treated," *J. Psych. Res.* 34: 171-181 (2000).
Zorilla et al., "Progress in corticotropin-releasing factor-1 antagonist development," *Drug Discovery Today*, 15(9-10): 371-383 (2010).
United Kingdom Intellectual Property Office, Combined Search and Examination Report in Great Britain Patent Application No. 1207102.3 (dated Aug. 21, 2012).
United Kingdom Intellectual Property Office, Combined Search and Examination Report in Great Britain Patent Application No. 1210686.0 (dated Oct. 16, 2012).
European Patent Office, International Search Report in International Patent Application No. PCT/EP2013/062552 (dated Sep. 13, 2013).
European Patent Office, Written Opinion in International Patent Application No. PCT/EP2013/062552 (dated Sep. 13, 2013).
European Patent Office, International Search Report in International Patent Application No. PCT/EP2013/058413 (dated Nov. 18, 2013).
European Patent Office, Written Opinion in International Patent Application No. PCT/EP2013/058413 (dated Nov. 18, 2013).
European Patent Office, International Search Report in International Patent Application No. PCT/EP2013/058411 (dated Nov. 21, 2013).
European Patent Office, Written Opinion in International Patent Application No. PCT/EP2013/058411 (dated Nov. 21, 2013).

(56) References Cited

OTHER PUBLICATIONS

European Patent Office, International Search Report in International Application No. PCT/EP2014/062592 (dated Oct. 14, 2014).
European Patent Office, Written Opinion in International Application No. PCT/EP2014/062592 (dated Oct. 14, 2014).
European Patent Office, Communication Pursuant to Article 94(3) EPC in European Patent Application No. 13717792.9 (dated May 12, 2016).
Japanese Patent Office, Notification of Reasons for Rejection in Japanese Patent Application No. 2015/516647 (dated Mar. 28, 2017).

* cited by examiner

METHOD FOR PREDICTING A TREATMENT RESPONSE TO A CRHR1 ANTAGONIST AND/OR A $V_{1B}$ ANTAGONIST IN A PATIENT WITH DEPRESSIVE AND/OR ANXIETY SYMPTOMS

CROSS-REFERENCE TO RELATED APPLICATIONS

This patent application is a continuation of copending U.S. patent application Ser. No. 14/898,877, filed Dec. 16, 2015, which is the U.S. national phase of International Patent Application No. PCT/EP/2014/062592, filed on Jun. 16, 2014, which claims the benefit of Great Britain Patent Application No. 1310782.6, filed Jun. 17, 2013, the disclosures of which are incorporated herein by reference in their entireties.

Incorporation-By-Reference of Material Electronically Submitted Incorporated by reference in its entirety herein is a computer-readable nucleotide/amino acid sequence listing submitted herewith and identified as follows: 2,762 bytes ASCII (Text) file named "741374_SequenceListing_ST25.txt," created Dec. 21, 2018.

FIELD OF THE INVENTION

The present invention relates to a method for predicting a treatment response to a corticotropin releasing hormone receptor type 1 (CRHR1) antagonist and/or a vasopressin receptor 1B ($V_{1B}$) antagonist in a patient with depressive and/or anxiety symptoms. The present invention furthermore relates to a $V_{1B}$ receptor antagonist and/or fluid control CRHR1 antagonist for use in the treatment of depressive symptoms and/or anxiety symptoms in a patient. Also, kits, diagnostic compositions, devices and microarrays allowing the determination of the presence or absence of at least one polymorphic variant in the AVPR1B gene and the presence or absence of at least one polymorphic variant in the patient's genome excluding the AVPR1B gene in the nucleic acid sample are described.

BACKGROUND OF THE INVENTION

While current antidepressant drugs are effective treatments of depression and anxiety symptoms in a number of psychiatric disorders, a large fraction of patients only show partial remission of symptoms or do not respond at all (Trivedi et al., *Am J Psychiatry*. January 2006; 163(1):28-40). This is likely due to the fact that these drugs do not target the inherent pathophysiologic disturbances leading to the clinical condition. A number of antidepressant strategies derived from both animal as well as human studies have been tested, but so far with little success. One of these approaches is the use of corticotropin releasing hormone receptor type 1 (CRHR1) and/or $V_{1B}$ antagonists. Increased activity or concentrations of its ligand CRH in the brain or the cerebrospinal fluid have been shown to be associated with depression and anxiety in humans (Nemeroff et al., *Arch Gen Psychiatry*. June 1988; 45(6):577-579; Nemeroff et al., *Science*. Dec. 14 1984; 226(4680):1342-1344; Purba et al., *Arch Gen Psychiatry*. February 1996:53(2): 137-143; Carpenter et al., *Neuropsycho-pharmacology*. April 2004; 29(4):777-784.), primates (Coplan et al., *Proc Natl Acad Sci USA*. Feb. 20 1996; 93(4):1619-1623; Sanchez et al., *Dev Psychopathol*. Summer 2001; 13(3):419-449.) and rodents (Muller et al., *Nat Neurosci*. October 2003:6(10): 1100-1107; Timpl et al., *Nat Genet*. June 1998; 19(2): 162-166.). In addition, a wealth of data ranging from molecular studies in experimental animals to open label studies in human patients indicate that CRHR1 and/or $V_{1B}$ antagonists are a promising approach in the treatment of depression and anxiety (Ising et al., *Exp Clin Psychopharmacol*. December 2007; 15(6):519-528; Holsboer F., *CNS Spectr*. July 2001; 6(7):590-594; Paez-Pereda et al.; *Expert Opin Investig Drugs*. April; 20(4):519-535). However, so far all randomized clinical trials have failed to demonstrate the superiority of these drugs to placebo (Coric et al., *Depress Anxiety*. May 2010; 27(5):417-425; Binneman et al., *Am J Psychiatry*. May 2008:165(5):617-620).

Hence, there is still a need for methods for predicting a treatment response to CRHR1 and/or $V_{1B}$ antagonists as well as to other antidepressant and/or anxiolytic drugs effective in the treatment of depressive symptoms and/or anxiety symptoms in a number of psychiatric disorders.

SUMMARY OF THE INVENTION

It has now been found that despite the so far unsuccessful clinical trials, a specific group of patients showing depressive symptoms and/or anxiety symptoms, including patients with central CRH overactivity exhibit a treatment response to CRHR1 antagonists and/or $V_{1B}$ antagonists. It has also been found that the presence or absence of at least one polymorphic variant in the AVPR1B gene in combination with the presence or absence of at least one polymorphic variant in the patient's genome excluding the AVPR1B gene is indicative for a treatment response of patients suffering from depression and/or anxiety symptoms to CRHR1 antagonists and/or VIE antagonists.

In one aspect, the present invention relates to a method for predicting a treatment response to a corticotropin releasing hormone receptor type 1 (CRHR1) antagonist and/or a vasopressin receptor 1B ($V_{1B}$ receptor) antagonist in a patient with depressive and/or anxiety symptoms comprising the following steps:

(i) determining the presence or absence of at least one polymorphic variant in the vasopressin receptor 1B (AVPR1B) gene in a nucleic acid sample of said patient, and (ii) determining the presence or absence of at least one polymorphic variant in the patient's genome excluding the AVPR1B gene in the nucleic acid sample of said patient, wherein the combination of the presence or absence of at least one polymorphic variant in the AVPR1B gene with the presence or absence of at least one polymorphic variant in the patient's genome excluding the AVPR1B gene is indicative for the treatment response.

In one embodiment of the method according to the present invention, the method is for predicting a treatment response to a vasopressin receptor 1B ($V_{1B}$ receptor) antagonist in a patient with depressive and/or anxiety symptoms and comprises the following steps:

(i) determining the presence or absence of at least one polymorphic variant in the vasopressin receptor 1B (AVPR1B) gene in a nucleic acid sample of said patient, and (ii) determining the presence or absence of at least one polymorphic variant in the patient's genome excluding the AVPR1B gene in the nucleic acid sample of said patient, wherein the combination of the presence or absence of at least one polymorphic variant in the AVPR1B gene with the presence or absence of at least one polymorphic variant in the patient's genome excluding the AVPR1B gene is indicative for the treatment response.

In one embodiment of the method according to the present invention the polymorphic variant in the AVPR1B gene and/or in the patient's genome excluding the AVPR1B gene is a single nucleotide polymorphism (SNP). For example, the polymorphic variant in the AVPR1B gene is an SNP. In another exemplary embodiment, the polymorphic variant in the patient's genome excluding the AVPR1B gene is an SNP.

In one embodiment, a polymorphic variant in the patient's genome is SNP rs28373064 which is represented by a single polymorphic change at position 27 of SEQ ID NO: 1, wherein in one or two alleles of the wild-type nucleotide A is replaced by indicator nucleotide G.

In another embodiment, the at least one polymorphic variant in the patient's genome excluding the AVPR1B gene is selected from the group of biomarkers comprising:

SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

In another embodiment of the method according to the invention the group of biomarkers comprises at least 2, at least 5, at least 8 or at least 11 of the biomarkers defined herein. For example, the presence or absence of at least 2, at least 5, at least 8 or at least 11 polymorphic variants or biomarkers as defined above is determined in step (ii) of the method described above.

In one embodiment, the group of biomarkers consists of the biomarkers as defined herein. For example, the presence or absence of all 14 polymorphic variants or biomarkers in the patient's genome excluding the AVPR1B gene as defined above are determined in step (ii) of the method described above.

In a further embodiment of the method described herein the combination of the presence or absence of SNP rs28373064 with the presence or absence of at least 1, at least 2, at least 3, at least 4, at least 5, at least 6, at least 7, at least 8, at least 9, at least 10, at least 11, at least 12, at least 13 or all of the biomarkers as defined herein for polymorphic variants excluding the AVPR1B gene is determined.

In another embodiment, a polymorphic variant in the AVPR1B gene of the patient's genome is SNP rs28373064 which is represented by a single polymorphic change at position 27 of SEQ ID NO: 1, wherein in one or two alleles of the wild-type nucleotide A is replaced by indicator nucleotide G or an SNP in strong linkage disequilibrium with SNP rs28373064.

In another embodiment, the at least one polymorphic variant in the patient's genome excluding the AVPR1B gene is selected from the group of biomarkers comprising SNP rs9880583 which is represented by a single polymorphic change at position 27 of SEQ ID NO: 2; wherein in one or two alleles the wild-type nucleotide C is replaced by indicator nucleotide G, SNP rs13099050 which is represented by a single polymorphic change at position 27 of SEQ ID NO: 3; wherein in one or two alleles the wild-type nucleotide A is replaced by indicator nucleotide C, SNP rs7441352 which is represented by a single polymorphic change at position 27 of SEQ ID NO: 4; wherein in one or two alleles the wild-type nucleotide A is replaced by indicator nucleotide G; SNP rs730258 which is represented by a single polymorphic change at position 27 of SEQ ID NO: 5, wherein in one or two alleles the wild-type nucleotide C is replaced by indicator nucleotide T; SNP rs12654236 which is represented by a single polymorphic change at position 27 of SEQ ID NO: 6, wherein in one or two alleles the wild-type nucleotide A is replaced by indicator nucleotide G; SNP rs17091872 which is represented by a single polymorphic change at position 27 of SEQ ID NO: 7, wherein in one or two alleles the wild-type nucleotide A is replaced by indicator nucleotide G; SNP rs12254219 which is represented by a single polymorphic change at position 27 of SEQ ID NO: 8, wherein in one or two alleles the wild-type nucleotide C is replaced by indicator nucleotide T; SNP rs11575663 which is represented by a single polymorphic change at position 27 of SEQ ID NO: 9, wherein in one or two alleles the wild-type nucleotide A is replaced by indicator nucleotide G; SNP rs7080276 which is represented by a single polymorphic change at position 27 of SEQ ID NO: 10, wherein in one or two alleles the wild-type nucleotide A is replaced by indicator nucleotide G; SNP rs7416 which is represented by a single polymorphic change at position 27 of SEQ ID NO: 11, wherein in one or two alleles the wild-type nucleotide A is replaced by indicator nucleotide G; SNP rs12424513 which is represented by a single polymorphic change at position 27 of SEQ ID NO: 12, wherein in one or two alleles the wild-type nucleotide C is replaced by indicator nucleotide T; SNP rs1035050 which is represented by a single polymorphic change at position 27 of SEQ ID NO: 13, wherein in one or two alleles the wild-type nucleotide C is replaced by indicator nucleotide T; SNP rs9959162 which is represented by a single polymorphic change at position 27 of SEQ ID NO: 14, wherein in one or two alleles the wild-type nucleotide A is replaced by indicator nucleotide C; SNP rs8088242 which is represented by a single polymorphic change at position 27 of SEQ ID NO: 15, wherein in one or two alleles the wild-type nucleotide A is replaced by indicator nucleotide G; and/or an SNP in strong linkage disequilibrium with any of the foregoing SNPs.

Another aspect of the invention relates to a $V_{1B}$ receptor antagonist and/or CRHR1 antagonist for use in the treatment of depressive symptoms and/or anxiety symptoms in a patient, the patient showing a combination of the presence or absence of at least one polymorphic variant in the AVPR1B gene with the presence or absence of at least one polymorphic variant in the patient's genome excluding the AVPR1B gene.

In one embodiment, the invention relates to a $V_{1B}$ receptor antagonist for use in the treatment of depressive symptoms and/or anxiety symptoms in a patient, the patient showing a combination of the presence or absence of at least one polymorphic variant in the AVPR1B gene with the presence or absence of at least one polymorphic variant in the patient's genome excluding the AVPR1B gene.

In one embodiment of the $V_{1B}$ receptor antagonist and/or CRHR1 antagonist for use according to the present invention, the polymorphic variant in the AVPR1B gene and/or in the patient's genome excluding the AVPR1B gene is a single nucleotide polymorphism (SNP). For example, the polymorphic variant in the AVPR1B gene is an SNP. In another exemplary embodiment, the polymorphic variant in the patient's genome excluding the AVPR1B gene is an SNP.

In one embodiment of the invention a polymorphic variant in the AVPR1B gene is SNP rs28373064 which is represented by a single polymorphic change at position 27 of SEQ ID NO: 1, wherein in one or two alleles of the wild-type nucleotide A is replaced by indicator nucleotide G.

In one embodiment of the $V_{1B}$ receptor antagonist and/or CRHR1 antagonist for use according to the invention, the at least one polymorphic variant in the patient's genome excluding the AVPR1B gene is selected from the group of biomarkers comprising:

SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

In one embodiment, the group of biomarkers comprises at least 2, at least 5, at least 8 or at least 11 of the biomarkers defined herein. For example, the patient shows the presence or absence of at least 2, at least 5, at least 8 or at least 11 polymorphic variants or biomarkers in his genome excluding the AVPR1B gene as defined above.

In another embodiment, the group of biomarkers consists of the biomarkers as defined herein. For example, the patient shows the presence or absence of all 14 polymorphic variants or biomarkers in his genome excluding the AVPR1B gene as defined above.

In a further embodiment, the patient shows a combination of the presence or absence of SNP rs28373064 with the presence or absence of at least 1, at least 2, at least 3, at least 4, at least 5, at least 6, at least 7, at least 8, at least 9, at least 10, at least 11, at least 12, at least 13 or all of the biomarkers defined herein for polymorphic variants excluding the AVPR1B gene.

In another embodiment, a polymorphic variant in the AVPR1B gene of the patient's genome is SNP rs28373064 which is represented by a single polymorphic change at position 27 of SEQ ID NO: 1, wherein in one or two alleles of the wild-type nucleotide A is replaced by indicator nucleotide G or an SNP in strong linkage disequilibrium with SNP rs28373064.

In another embodiment, the at least one polymorphic variant in the patient's genome excluding the AVPR1B gene is selected from the group of biomarkers comprising SNP rs9880583 which is represented by a single polymorphic change at position 27 of SEQ ID NO: 2; wherein in one or two alleles the wild-type nucleotide C is replaced by indicator nucleotide G. SNP rs13099050 which is represented by a single polymorphic change at position 27 of SEQ ID NO: 3; wherein in one or two alleles the wild-type nucleotide A is replaced by indicator nucleotide C, SNP rs7441352 which is represented by a single polymorphic change at position 27 of SEQ ID NO: 4; wherein in one or two alleles the wild-type nucleotide A is replaced by indicator nucleotide G; SNP rs730258 which is represented by a single polymorphic change at position 27 of SEQ ID NO: 5, wherein in one or two alleles the wild-type nucleotide C is replaced by indicator nucleotide T; SNP rs12654236 which is represented by a single polymorphic change at position 27 of SEQ ID NO: 6, wherein in one or two alleles the wild-type nucleotide A is replaced by indicator nucleotide G; SNP rs17091872 which is represented by a single polymorphic change at position 27 of SEQ ID NO: 7, wherein in one or two alleles the wild-type nucleotide A is replaced by indicator nucleotide G; SNP rs12254219 which is represented by a single polymorphic change at position 27 of SEQ ID NO: 8, wherein in one or two alleles the wild-type nucleotide C is replaced by indicator nucleotide T; SNP rs11575663 which is represented by a single polymorphic change at position 27 of SEQ ID NO: 9, wherein in one or two alleles the wild-type nucleotide A is replaced by indicator nucleotide G; SNP rs7080276 which is represented by a single polymorphic change at position 27 of SEQ ID NO: 10, wherein in one or two alleles the wild-type nucleotide A is replaced by indicator nucleotide G; SNP rs7416 which is represented by a single polymorphic change at position 27 of SEQ ID NO: 11, wherein in one or two alleles the wild-type nucleotide A is replaced by indicator nucleotide G; SNP rs12424513 which is represented by a single polymorphic change at position 27 of SEQ ID NO: 12, wherein in one or two alleles the wild-type nucleotide C is replaced by indicator nucleotide T; SNP rs1035050 which is represented by a single polymorphic change at position 27 of SEQ ID NO: 13, wherein in one or two alleles the wild-type nucleotide C is replaced by indicator nucleotide T; SNP rs9959162 which is represented by a single polymorphic change at position 27 of SEQ ID NO: 14, wherein in one or two alleles the wild-type nucleotide A is replaced by indicator nucleotide C; SNP rs8088242 which is represented by a single polymorphic change at position 27 of SEQ ID NO: 15, wherein in one or two alleles the wild-type nucleotide A is replaced by indicator nucleotide G; and/or an SNP in strong linkage disequilibrium with any of the foregoing SNPs.

In one embodiment, the $V_{1B}$ receptor antagonist is selected from the group consisting of SSR149415, Org 52186, ABT-436 and/or ABT-558.

In a further embodiment, the CRHR1 antagonist is a class I or a class II antagonist. Optionally, the CRHR1 antagonist is selected from the group consisting of CP154,526, Antalarmin, CRA 5626, Emicerfont, DMP-696, DMP-904, DMP-695, SC-241, BMS-561388, Pexacerfont, R121919, NB130545, PD-171729, Verucerfont, NB134041, NB135965, SN003, CRA0450, SSR125543A, CP-316,311, CP-376,395, NBI-27914, ONO-2333Ms, NBI-34101, PF-572778, GSK561579 and GSK586529.

Another aspect of the present invention relates to a group of biomarkers, comprising:
SNP rs28373064 which is represented by a single polymorphic change at position 27 of SEQ ID NO: 1, wherein in one or two alleles of the wild-type nucleotide A is replaced by indicator nucleotide G, SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

In one embodiment of the invention the group of biomarkers consists of the biomarkers as defined herein.

Another aspect of the present invention relates to a group of biomarkers, comprising:
SNP rs28373064 which is represented by a single polymorphic change at position 27 of SEQ ID NO: 1, wherein in one or two alleles of the wild-type nucleotide A is replaced by indicator nucleotide G, SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G.

SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, SNP rs8088242 which is represented by a single polymorphic change at position 27 of SEQ ID NO: 15, wherein in one or two alleles the wild-type nucleotide A is replaced by indicator nucleotide G, and/or an SNP in strong linkage disequilibrium with any of the foregoing SNPs.

Another aspect of the invention relates to a kit, diagnostic composition or device for the analysis of the combination of at least one polymorphic variant in the AVPR1B gene with at least one polymorphic variant in the patient's genome excluding the AVPR1B gene, wherein the combination is indicative for the treatment response to $V_{1B}$ antagonists and/or CRHR1 antagonists.

One embodiment of the invention relates to a kit, diagnostic composition or device for the analysis of the combination of at least one polymorphic variant in the AVPR1B gene with at least one polymorphic variant in the patient's genome excluding the AVPR1B gene, wherein the combination is indicative for the treatment response to $V_{1B}$ antagonists.

Another embodiment relates to the kit, diagnostic composition or device, wherein a polymorphic variant in the AVPR1B gene is SNP rs28373064 which is represented by a single polymorphic change at position 27 of SEQ ID NO: 1, wherein in one or two alleles of the wild-type nucleotide A is replaced by indicator nucleotide G.

In one embodiment of the present invention the at least one polymorphic variant in the patient's genome excluding the AVPR1B gene is selected from the group of biomarkers comprising SNP rs9880583 which is represented by a single polymorphic change at position 27 of SEQ ID NO: 2, wherein in one or two alleles the wild-type nucleotide C is replaced by indicator nucleotide G, SNP rs3099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

In one embodiment of the invention, the kit, diagnostic composition or device comprises a probe selective for SNP rs28373064 and at least 1, at least 2, at least 3, at least 4, at least 5, at least 6, at least 7, at least 8, at least 9, at least 10, at least 11, at least 12, at least 13, or at least 14 probes selective for the biomarkers defined herein for polymorphic variants excluding the AVPR1B gene.

In another embodiment, a polymorphic variant in the AVPR1B gene of the patient's genome is SNP rs28373064 which is represented by a single polymorphic change at position 27 of SEQ ID NO: 1, wherein in one or two alleles of the wild-type nucleotide A is replaced by indicator nucleotide G or an SNP in strong linkage disequilibrium with SNP rs28373064.

In another embodiment, the at least one polymorphic variant in the patient's genome excluding the AVPR1B gene is selected from the group of biomarkers comprising SNP rs9880583 which is represented by a single polymorphic change at position 27 of SEQ ID NO: 2: wherein in one or two alleles the wild-type nucleotide C is replaced by indicator nucleotide G. SNP rs13099050 which is represented by a single polymorphic change at position 27 of SEQ ID NO: 3; wherein in one or two alleles the wild-type nucleotide A is replaced by indicator nucleotide C. SNP rs7441352 which is represented by a single polymorphic change at position 27 of SEQ ID NO: 4; wherein in one or two alleles the wild-type nucleotide A is replaced by indicator nucleotide G; SNP rs730258 which is represented by a single polymorphic change at position 27 of SEQ ID NO: 5, wherein in one or two alleles the wild-type nucleotide C is replaced by indicator nucleotide T; SNP rs12654236 which is represented by a single polymorphic change at position 27 of SEQ ID NO: 6, wherein in one or two alleles the wild-type nucleotide A is replaced by indicator nucleotide G; SNP rs17091872 which is represented by a single polymorphic change at position 27 of SEQ ID NO: 7, wherein in one or two alleles the wild-type nucleotide A is replaced by indicator nucleotide G; SNP rs12254219 which is represented by a single polymorphic change at position 27 of SEQ ID NO: 8, wherein in one or two alleles the wild-type nucleotide C is replaced by indicator nucleotide T; SNP rs11575663 which is represented by a single polymorphic change at position 27 of SEQ ID NO: 9, wherein in one or two alleles the wild-type nucleotide A is replaced by indicator nucleotide G; SNP rs7080276 which is represented by a single polymorphic change at position 27 of SEQ ID NO: 10, wherein in one or two alleles the wild-type nucleotide A is replaced by indicator nucleotide G; SNP rs7416 which is represented by a single polymorphic change at position 27 of SEQ ID NO: 11, wherein in one or two alleles the wild-type nucleotide A is replaced by indicator nucleotide G; SNP rs12424513 which is represented by a single polymorphic change at position 27 of SEQ ID NO: 12, wherein in one or two alleles the wild-type nucleotide C is replaced by indicator nucleotide T; SNP rs1035050 which is represented by a single polymorphic change at position 27 of SEQ ID NO: 13, wherein in one or two alleles the wild-type nucleotide C is replaced by indicator nucleotide T; SNP rs9959162 which is represented by a single polymorphic change at position 27 of SEQ ID NO: 14, wherein in one or two alleles the wild-type nucleotide A is replaced by indicator nucleotide C; SNP rs8088242 which is represented by a single polymorphic change at position 27 of SEQ ID NO: 15, wherein in one or two alleles the wild-type nucleotide A is replaced by indicator nucleotide G; and/or an SNP in strong linkage disequilibrium with any of the foregoing SNPs.

In a further embodiment of the invention, the kit, diagnostic composition or device further comprises an enzyme for primer elongation, nucleotides and/or labeling agents.

A further aspect of the invention relates to a microarray for the analysis of at least two SNPs indicative for a treatment response to a $V_{1B}$ receptor antagonist and/or a CRHR1 antagonist in a patient with depressive and/or anxiety symptoms, comprising at least one probe selective for a polymorphic variant in the AVPR1B gene and at least one probe selective for a polymorphic variant in the patient's genome excluding the AVPR1B gene.

In one embodiment, the invention relates to a microarray for the analysis of at least two SNPs indicative for a treatment response to a $V_{1B}$ receptor antagonist in a patient with depressive and/or anxiety symptoms, comprising at least one probe selective for a polymorphic variant in the AVPR1B gene and at least one probe selective for a polymorphic variant in the patient's genome excluding the AVPR1B gene.

In one embodiment of the microarray, the probe selective for a polymorphic variant in the AVPR1B gene is selective for SNP rs28373064 which is represented by a single polymorphic change at position 27 of SEQ ID NO: 1, wherein in one or two alleles of the wild-type nucleotide A is replaced by indicator nucleotide G.

In one embodiment, the probe selective for the least one polymorphic variant in the patient's genome excluding the AVPR1B gene is selected from a group of probes comprising probes selective for:

SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs7091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

In one embodiment, the microarray comprises a group of probes comprising a probe selective for SNP rs28373064 and at least 1, at least 2, at least 3, at least 4, at least 5, at least 6, at least 7, at least 8, at least 9, at least 10, at least 11, at least 12, at least 13, at least 14 or at least 15 probes selective for the biomarkers defined herein for polymorphic variants excluding the AVPR1B gene.

In another embodiment, the probe selective for a polymorphic variant in the AVPR1B gene is selective for SNP rs28373064 which is represented by a single polymorphic change at position 27 of SEQ ID NO: 1, wherein in one or two alleles of the wild-type nucleotide A is replaced by indicator nucleotide G and/or an SNP in strong linkage disequilibrium with SNP rs28373064.

In another embodiment, the probe selective for the least one polymorphic variant in the patient's genome excluding the AVPR1B gene is selected from a group of probes comprising probes selective for SNP rs9880583 which is represented by a single polymorphic change at position 27 of SEQ ID NO: 2: wherein in one or two alleles the wild-type nucleotide C is replaced by indicator nucleotide G, SNP rs13099050 which is represented by a single polymorphic change at position 27 of SEQ ID NO: 3; wherein in one or two alleles the wild-type nucleotide A is replaced by indicator nucleotide C, SNP rs7441352 which is represented by a single polymorphic change at position 27 of SEQ ID NO: 4; wherein in one or two alleles the wild-type nucleotide A is replaced by indicator nucleotide G; SNP rs730258 which is represented by a single polymorphic change at position 27 of SEQ ID NO: 5, wherein in one or two alleles the wild-type nucleotide C is replaced by indicator nucleotide T; SNP rs12654236 which is represented by a single polymorphic change at position 27 of SEQ ID NO: 6, wherein in one or two alleles the wild-type nucleotide A is replaced by indicator nucleotide G; SNP rs17091872 which is represented by a single polymorphic change at position 27 of SEQ ID NO: 7, wherein in one or two alleles the wild-type nucleotide A is replaced by indicator nucleotide G; SNP rs12254219 which is represented by a single polymorphic change at position 27 of SEQ ID NO: 8, wherein in one or two alleles the wild-type nucleotide C is replaced by indicator nucleotide T; SNP rs11575663 which is represented by a single polymorphic change at position 27 of SEQ ID NO: 9, wherein in one or two alleles the wild-type nucleotide A is replaced by indicator nucleotide G; SNP rs7080276 which is represented by a single polymorphic change at position 27 of SEQ ID NO: 10, wherein in one or two alleles the wild-type nucleotide A is replaced by indicator nucleotide G; SNP rs7416 which is represented by a single polymorphic change at position 27 of SEQ ID NO: 1, wherein in one or two alleles the wild-type nucleotide A is replaced by indicator nucleotide G; SNP rs12424513 which is represented by a single polymorphic change at position 27 of SEQ ID NO: 12, wherein in one or two alleles the wild-type nucleotide C is replaced by indicator nucleotide T; SNP rs1035050 which is represented by a single polymorphic change at position 27 of SEQ ID NO: 13, wherein in one or two alleles the wild-type nucleotide C is replaced by indicator nucleotide T; SNP rs9959162 which is represented by a single polymorphic change at position 27 of SEQ ID NO: 14, wherein in one or two alleles the wild-type nucleotide A is replaced by indicator nucleotide C; SNP rs8088242 which is represented by a single polymorphic change at position 27 of SEQ ID NO: 15, wherein in one or two alleles the wild-type nucleotide A is replaced by indicator nucleotide G; and/or an SNP in strong linkage disequilibrium with any of the foregoing SNPs.

DETAILED DESCRIPTION OF THE INVENTION

Figure 1:
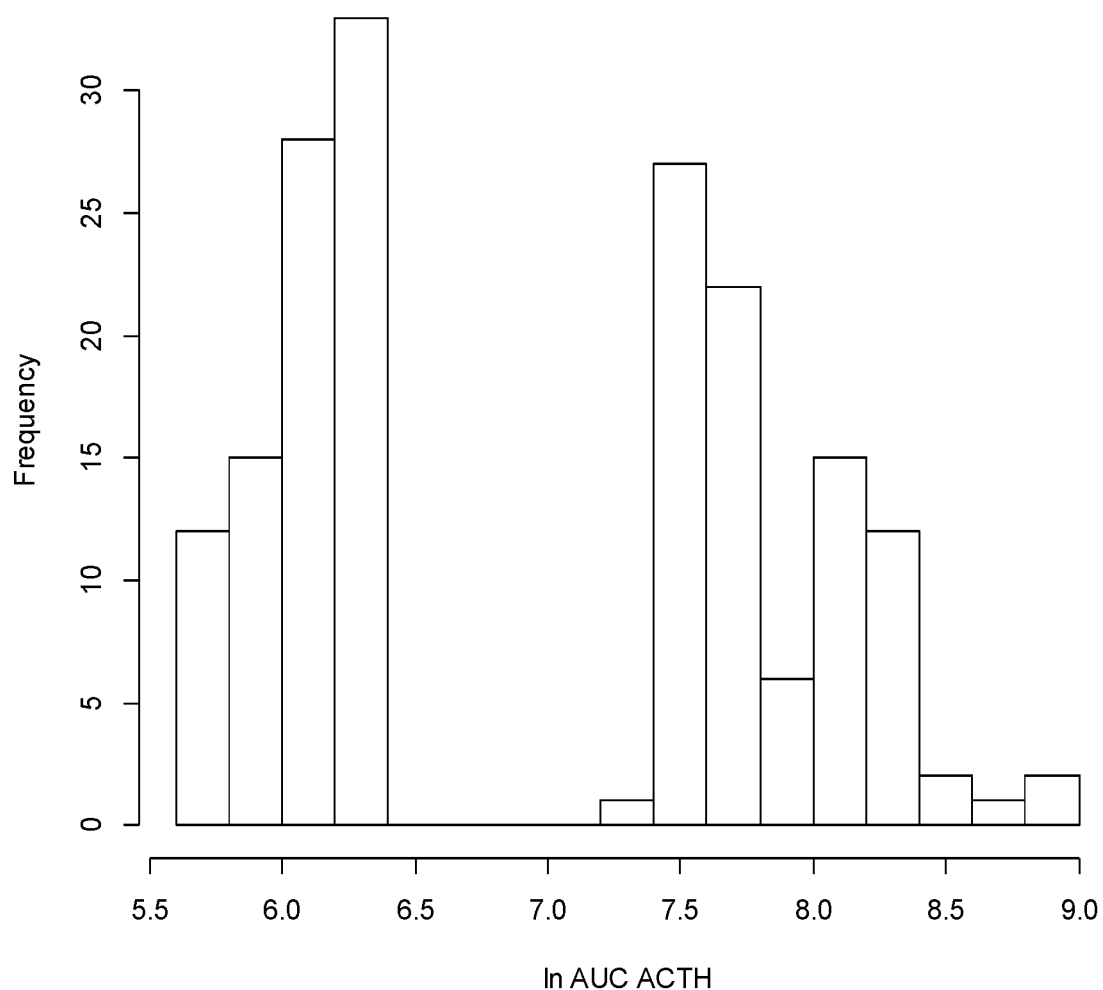
FIG. 1: Graph of the phenotypic distribution of ln(AAUC) at in-patient admission. The X-axis shows the ln of the AUC of the ACTH response and the Y-axis the frequency in total N/bin. #

Where the term "comprise" or "comprising" is used in the present description and claims, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or a definite article is used when referring to a singular noun such as "a" or "an" or "the", this includes a plural form of that noun unless specifically stated. Vice versa, when the plural form of a noun is used it refers also to the singular form. For example, when SNPs are mentioned, this is also to be understood as a single SNP.

Furthermore, the terms first, second, third or (a), (b), (c) or (i), (ii), (iii) and the like in the description and in the claims are used for distinguishing between similar elements and not necessarily for describing a sequential or chronological order. Also, if method steps are described herein in a certain order, it is to be understood that said steps do not necessarily have to be performed in the described sequential or chronological order. It is to be understood that the terms so used or the method steps described are interchangeable under appropriate circumstances and that the embodiments of the invention described herein are capable of operation in other sequences than described or illustrated herein.

Further definitions of the terms will be given below in the context of which the terms are used.

So far clinical trials have failed to demonstrate the superiority over placebos of CRHR1 antagonists and/or $V_{1B}$ receptor antagonists in the treatment of depression and/or anxiety symptoms. This lack of superiority to placebo may be due to the fact that only patients who suffer from central CRH overactivity would indeed profit from treatment with CRHR1 and/or $V_{1B}$ receptor antagonists. If an assessment of CRH activity is not made prior to CRHR1 antagonist treatment, effects would be diluted by patients without CRH system overactivity not responding to the CRHR1 antagonist (Holsboer F., *Nat Rev Neurosci*. August 2008; 9(8):638-646) or $V_{1B}$ receptor antagonist. Overactivity of the CRH system in patients may be reflected by the extent of the corticotropin (ACTH) and cortisol response to the combined dexamethasone (dex) suppression/CRH stimulation test (Holsboer F., *J Psychiatr Res*. May-June 1999; 33(3): 181-214: Holsboer F., *Ann N Y Acad Sci*. December 2003; 1007:394-404.).

It has now been found that CRH overactivity and, consequently, a treatment response to CRHR1 antagonists and/or $V_{1B}$ receptor antagonists of a patient suffering from depressive and/or anxiety symptoms may be predicted by determining the presence or absence of at least one polymorphic variant in the vasopressin receptor 1B (AVPR1B) gene in combination with the presence or absence of at least one polymorphic variant in the patient's genome excluding the AVPR1B gene.

In one aspect the present invention relates to a method for predicting a treatment response to a corticotropin releasing hormone receptor type 1 (CRHR1) antagonist and/or a vasopressin receptor 1B ($V_{1B}$ receptor) antagonist in a patient with depressive and/or anxiety symptoms comprising the following steps:

(i) determining the presence or absence of at least one polymorphic variant in the vasopressin receptor 1B (AVPR1B) gene in a nucleic acid sample of said patient, and (ii) determining the presence or absence of at least one polymorphic variant in the patient's genome excluding the AVPR1B gene in the nucleic acid sample of said patient, wherein the combination of the presence or absence of at least one polymorphic variant in the AVPR1B gene with the presence or absence of at least one polymorphic variant in the patient's genome excluding the AVPR1B gene is indicative for the treatment response.

In one embodiment the present invention relates to a method for predicting a treatment response to a vasopressin receptor 1B ($V_{1B}$ receptor) antagonist in a patient with depressive and/or anxiety symptoms comprising the following steps:

(i) determining the presence or absence of at least one polymorphic variant in the vasopressin receptor 1B (AVPR1B) gene in a nucleic acid sample of said patient, and (ii) determining the presence or absence of at least one polymorphic variant in the patient's genome excluding the AVPR1B gene in the nucleic acid sample of said patient, wherein the combination of the presence or absence of at least one polymorphic variant in the AVPR1B gene with the presence or absence of at least one polymorphic variant in the patient's genome excluding the AVPR1B gene is indicative for the treatment response.

A "polymorphic site" or "polymorphic variant" or "biomarker" as used herein relates to the position of a polymorphism or single nucleotide polymorphism (SNP) as described herein within the genome or portion of a genome of a subject, or within a genetic element derived from the genome or portion of a genome of a subject. In particular, the polymorphic variant in the AVPR1B gene and/or in the patient's genome excluding the AVPR1B gene is a single nucleotide polymorphism. The term "single nucleotide polymorphism" is well understood by the skilled person and refers to a point mutation at a certain position in the nucleotide sequence. In other words, only one nucleotide differs in a certain region or portion or genetic element of the subject's genome.

The SNPs as described herein may be present on the Watson or the Crick strand, with presence of the corresponding base. If, for example, a polymorphism is present on the Watson strand as A, it is present on the Crick strand as T, if the polymorphism is present on the Watson strand as T, it is present on the Crick strand as A, if the polymorphism is present on the Watson strand as G, it is present on the Crick strand as C, and if the polymorphism is present on the Watson strand as C, it is present on the Crick strand as G, and vice versa. Also, the insertion or deletion of bases may be detected on the Watson and/or the Crick strand, with correspondence as defined above. For analytic purposes the strand identity may be defined, or fixed, or may be choose at will, e.g. in dependence on factors such the availability of binding elements. GC-content etc. Furthermore, for the sake of accuracy, the SNP may be defined on both strands (Crick and Watson) at the same time, and accordingly be analyzed.

The term "allele" or "allelic sequence" as used herein refers to a particular form of a gene or a particular nucleotide, e.g. a DNA sequence at a specific chromosomal location or locus. In certain embodiments of the present invention a SNP as defined herein may be found at or on one of two alleles in the human genome of a single subject. In further specific embodiments, a SNP as defined herein may also be found at or on both alleles in the human genome of a single subject. The presence of an indicator nucleotide or an indicator triplet as defined herein on both alleles may have a higher predictive value than the presence of an indicator nucleotide or an indicator triplet on one allele only, the other allele comprising a wild-type genotype.

The nucleotide that is present in the majority of the population is also referred to as wild-type allele or major allele. In one embodiment, the term "wild-type sequence" as used herein refers to the sequence of an allele, which does not show the phenotype with CRH overactivity or does not indicate a treatment response to CRHR1 receptor antagonists and/or $V_{1B}$ receptor antagonists. In another embodiment, the term "wild-type sequence" as used herein refers to the sequence of an allele, which shows the phenotype with CRH overactivity or indicates a treatment response to CRHR1 receptor antagonists and/or $V_{1B}$ receptor antagonists. The term may further refer to the sequence of the non phenotype-associated allele with the highest prevalence within a population, e.g. within a Caucasian population. As used herein, this state is defined as "absence of a SNP".

The specific nucleotide that is present in the minority of the population is also referred as the point mutation, mutated nucleotide or minor allele. As used herein, this state is defined as "presence of a SNP", "the presence of a polymorphic variant" or "the presence of a biomarker".

In theory, the wild-type allele could be mutated to three different nucleotides. However, the event of a mutation to a first nucleotide in the reproductive cells of an individual that gets established in a population occurs very rarely. The event that the same position is mutated to a second nucleotide and established in the population virtually never occurs and can be therefore neglected. Therefore, as used herein, a certain nucleotide position in the genome of an individual can have two states, the wild-type state (absence of a SNP) and the mutated state (presence of a SNP).

As described above, the combination of the presence or absence of at least one polymorphic variant in the AVPR1B gene with the presence of at least one polymorphic variant in the patient's genome excluding the AVPR1B gene as described herein in a sample of a patient is indicative for a treatment response to CRHR1 antagonists and/or $V_{1B}$ receptor antagonists. The at least one polymorphic variant in the AVPR1B gene and/or in the patient's genome excluding the AVPR1B gene may be selected from a group of biomarkers. The term "biomarker", as used herein, relates to any nucleic acid sequence of any length, or a derivative thereof, which comprises a polymorphic variant such as the polymorphic variant in the AVPR1B gene or the polymorphic variants in the patient's genome excluding the AVPR1B gene as defined herein. In particular, the term "biomarker" may relate to SNPs. Thus, the at least one polymorphic variant in the AVPR1B gene and/or in the patient's genome excluding the AVPR1B gene may be selected from a group of biomarkers comprising SNP rs28373064 which is represented by a single polymorphic change at position 27 of SEQ ID NO: 1, wherein in one or two alleles of the wild-type nucleotide A is replaced by indicator nucleotide G.

SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

A biomarker may, for instance, be represented by a nucleic acid molecule of a length of e.g. 1 nt, 2 nt, 3 nt, 4 nt, 5 nt, 10 nt, 15 nt, 20 nt, 25 nt, 30 nt, 35 nt, 40 nt, 45 nt, 50 nt, 60 nt, 70 nt, 80 nt, 90 nt, 100 nt, 200 nt, 300 nt, 400 nt, 500 nt, 1000 nt, 2000 nt, or more or any length in between these lengths. The representing nucleic acid may be any suitable nucleic acid molecule, e.g. a DNA molecule, e.g. a genomic DNA molecule or a cDNA molecule, or a RNA molecule, or a derivative thereof. The biomarker may further be represented by translated forms of the nucleic acid, e.g. a peptide or protein as long as the polymorphic modification leads to a corresponding modification of the peptide or protein. Corresponding information may be readily available to the skilled person from databases such as the NCBI SNP repository and NCBI Genbank.

"Combinations of polymorphic variants" as used herein may refer to the presence or absence of at least one polymorphic variant in the AVPR1B gene in combination with the presence or absence a set or group of polymorphic variants in the patient's genome excluding the AVPR1B gene in a sample of a patient, e.g. to the presence of a combination of a polymorphic variant in the AVPR1B gene in combination with the presence of 1, 2, 3, 4, 5, 6, 7, 8, 9, 10, 11, 12, 13, or 14 polymorphic variant(s) as described herein for polymorphic variants in the patient's genome excluding the AVPR1B gene. Combinations of polymorphic variants may relate to the presence of at least one polymorphic variant in the AVPR1B gene, optionally SNP rs28373064, in combination with the presence of 1, 2, 3, 4, 5, 6, 7, 8, 9, 10, 11, 12, 13, or 14 poly-morphic variant(s) as described herein for polymorphic variants in the patient's genome excluding the AVPR1B gene. Combinations of polymorphic variants may also relate to the absence of at least one polymorphic variant in the AVPR1B gene, optionally SNP rs28373064, in combination with the absence of 1, 2, 3, 4, 5, 6, 7, 8, 9, 10, 1, 12, 13, or 14 polymorphic variant(s) as described herein for polymorphic variants in the patient's genome excluding the AVPR1B gene. Combinations of polymorphic variants may also relate to the presence of at least one polymorphic variant in the AVPR1B gene, optionally SNP rs28373064, in combination with the absence of 1, 2, 3, 4, 5, 6, 7, 8, 9, 10, 11, 12, 13, or 14 polymorphic variant(s) as described herein for polymorphic variants in the patient's genome excluding the AVPR1B gene. Combinations of polymorphic variants may also relate to the absence of at least one polymorphic variant in the AVPR1B gene, optionally SNP rs28373064, in combination with the presence of 1, 2, 3, 4, 5, 6, 7, 8, 9, 10, 11, 12, 13, or 14 polymorphic variant(s) as described herein for polymorphic variants in the patient's genome excluding the AVPR1B gene. In one embodiment, combinations of polymorphic variants relates to the presence of at least one polymorphic variant in the AVPR1B gene, optionally SNP rs28373064, in combination with the presence of 1, 2, 3, 4, 5, 6, 7, 8, 9, 10, 11, 12, 13, or 14 polymorphic variant(s) as described herein for polymorphic variants in the patient's genome excluding the AVPR1B gene. In another embodiment, combinations of polymorphic variants relates to the absence of at least one polymorphic variant in the AVPR1B gene, optionally SNP rs28373064, in combination with the absence of 1, 2, 3, 4, 5, 6, 7, 8, 9, 10, 11, 12, 13, or 14 polymorphic variant(s) as described herein for polymorphic variants in the patient's genome excluding the AVPR1B gene.

The presence or absence of a combination of polymorphic variants may be associated with a specific weighting factor describing the impact of the presence of such a combination on the prediction of the treatment response to a CRHR1 antagonist and/or a $V_{1B}$ receptor antagonist. Thus, a specific weighting factor describing the impact of the presence or absence of such a combination on the prediction of the treatment response to a CRHR1 antagonist and/or a $V_{1B}$ receptor antagonist may be associated with the fact that
at least one polymorphic variant in the AVPR1B gene, optionally SNP rs28373064, is present and 1, 2, 3, 4, 5, 6, 7, 8, 9, 10, 11, 12, 13, or 14 poly-morphic variant(s) as described herein for polymorphic variants in the patient's genome excluding the AVPR1B gene is/are present,
at least one polymorphic variant in the AVPR1B gene, optionally SNP rs28373064, is absent and 1, 2, 3, 4, 5, 6, 7, 8, 9, 10, 11, 12, 13, or 14 poly-morphic variant(s) as described herein for polymorphic variants in the patient's genome excluding the AVPR1B gene is/are absent,
at least one polymorphic variant in the AVPR1B gene, optionally SNP rs28373064, is present and 1, 2, 3, 4, 5, 6, 7, 8, 9, 10, 11, 12, 13, or 14 poly-morphic variant(s) as described herein for polymorphic variants in the patient's genome excluding the AVPR1B gene is/are absent,
at least one polymorphic variant in the AVPR1B gene, optionally SNP rs28373064, is absent and 1, 2, 3, 4, 5, 6, 7, 8, 9, 10, 11, 12, 13, or 14 poly-morphic variant(s) as described herein for polymorphic variants in the patient's genome excluding the AVPR1B gene is/are present.

Table 1 provides an overview of SNPs (inside and outside of the AVPR1B gene) according to the present invention and being suitable for predicting a treatment response of patients suffering from depressive and/or anxiety symptoms to a treatment with a CRHR1 antagonist and/or a $V_{1B}$ receptor antagonist, whereby the presence or absence of the indicated polymorphic change (i.e. the presence or absence of the indicator nucleotide) in one or more of the biomarkers may be indicative for a patient responding to the treatment with a CRHR1 receptor antagonist and/or a $V_{1B}$ receptor antagonist.

The term "indicator nucleotide" refers to a non-wild-type nucleotide at positions of SEQ ID NO: 1 to 15 as described in Table 1.

In one embodiment, the set of biomarkers which may be used in the method of the present invention comprises at least 2, at least 5, at least 8 or at least 11 of the biomarkers defined in Table 1. It is understood that the set of biomarkers may comprise any further biomarker not explicitly described herein but considered suitable by the person skilled in the art. Such additional biomarkers may include additional polymorphic variants which have been obtained by a genome wide screening for polymorphic variants in a patient having depressive symptoms and/or anxiety symptoms and optionally identified as being associated with an increased ACTH response to a combined dex/CRH test.

In one embodiment, the group of biomarkers whose presence or absence is determined in methods according to the present invention comprises biomarkers which are selected from biomarkers as defined in Table 1 and SNPs in strong linkage disequilibrium with any of the SNPs shown in Table 1.

In another embodiment, the group of biomarkers whose presence or absence is determined in a method according to the present invention consists of the biomarkers defined in Table 1.

TABLE 1

SNPs (together with flanking sequences) which may be used to predict the response to $V_{1B}$ receptor antagonists and/or CRHR1 antagonists in patients with depressive symptoms and/or anxiety symptoms. The position on the SNP is indicated as [wild-type nucleotide/indicator nucleotide].

| SNP_ID | Sequence | SEQ ID NO | Position of polymorphic change |
|---|---|---|---|
| rs28373064 | TCCTGCACCGGCTAGCCGGCTGGCAG[A/G]GGG CGCGCCAACAGCCGCCAGCCGA | 1 | 27 |
| rs9880583 | AAATGAAGCCACTTGTTTCTTCTCCA[C/G]CTAT GACCTAGACACCCCCTCCCCA | 2 | 27 |
| rs13099050 | AATGAATAAGAAGCCTCTCAAGACAG[A/C]AGG ATTCAACCTTATAGCTTTGATA | 3 | 27 |
| rs7441352 | TCCTCTCCCCCTATCTCTGCTTTTCA[A/G]CATTG TACTGGAAGTCCTAGCTAAT | 4 | 27 |
| rs7441352 | AGAAATAAAATCATTTCATATTCATG[C/T]AATA GATACAAGAAATGTATTAAAG | 5 | 27 |

TABLE 1-continued

SNPs (together with flanking sequences) which may be used to predict the response to V$_{1B}$ receptor antagonists and/or CRHR1 antagonists in patients with depressive symptoms and/or anxiety symptoms. The position on the SNP is indicated as [wild-type nucleotide/indicator nucleotide].

| SNP_ID | Sequence | SEQ ID NO | Position of polymorphic change |
|---|---|---|---|
| rs730258 | GGACTGTTTTTGTATTCAGTGCACAG[A/G]TGTGTGTGAAGACACCCAGCATGTT | 6 | 27 |
| rs12654236 | AATGCAAATTTTTATCAAGTACCTAC[A/G]ATGTGCGGGCAATTTTGCAAGGTGC | 7 | 27 |
| rs12254219 | CTGTGTCCTTGAAGCCCATGACAGTG[C/T]CTGACACAAAGTAGTTGCTCAATAA | 8 | 27 |
| rs11575663 | CTTTATTTACAAAAACAAAACTGCTA[A/G]GCTTGGCCCAAGGGCCCTTATTTGC | 9 | 27 |
| rs7080276 | GTCCACGTGACTTCACACATCAGCCA[A/G]TGAGGTCTGGCCTCTGTCACCAAAC | 10 | 27 |
| rs7416 | GTAACCGGATGCATTTTTTNNNNNNA[A/G]AATTTCTCCCTTATCTACTATGATG | 11 | 27 |
| rs12424513 | GCAGCCGGACCCTGTATTGAGGAGGA[C/T]GGGCAGGGAAAGCATGCTTTAGAGA | 12 | 27 |
| rs1035050 | CTCCCCATCTTTGTATTGATGTAAGC[C/T]TCACCTCTCTGCCCACTGGCATCCG | 13 | 27 |
| rs9959162 | TCCTCCTGATTGCCTTCAAATTAGGA[A/C]ATCAGTTGAAGTTCCTGCTTTCAGA | 14 | 27 |
| rs8088242 | AACATCTGACAAAAGGTAAGAACTCA[A/G]TAAATGCTTTGATAGAACTTAAATA | 15 | 27 |

Polymorphisms in linkage disequilibrium with a SNP of Table 1 can be identified by by methods known in the art. For example, Develin and Risch (Genomics, 1995) provide guidance for determining the parameter delta (also referred to as the "r") as a standard measure of the disequilibrium. Gabriel et al. (Science, 2002) provides instructions for finding the maximal r$^2$ value in populations for disease gene mapping. Further, Carlson et al. (Am J. Hum. Genet. (2003) disclose methods for selecting and analyzing polymorphisms based on linkage disequilibrium for disease gene association mapping. Stoyanovich and Pe'er (Bioinformatics, 2008) show that polymorphisms in linkage disequilibrium with indentified SNPs have virtually identical response profiles. Currently, several databases provide datasets that can be searched for polymorphisms in strong linkage disequilibrium, which can be accessed by the following addresses: http://1000.genomes.org, http://www.hapmap.org, http://www.broadinsitute.org/mpg/snap. An example workflow for determining SNPs linkage disequilibrium to a specific SNP is outlined in Uhr et al. (Neuron, 2008).

SNP in strong linkage disequilibrium as used herein means that the SNP is in linkage disequilibrium with an r$^2$ higher than 0.7 or higher than 0.8 in the tested population or an ethnically close reference population with the identified SNP.

In one embodiment, the polymorphic variant in the AVPR1B gene whose presence or absence is determined is SNP rs28373064. In a further embodiment, the polymorphic variant in the patient's genome excluding the AVPR1B gene whose presence or absence is determined is selected from the group of the biomarkers (except SNP rs28373064) provided in Table 1. For example, the polymorphic variant in the patient's genome excluding the AVPR1B gene whose presence or absence is selected from biomarkers having SEQ ID NO: 2 to 15.

In a further embodiment of the method described herein, the combination of the presence or absence of SNP rs28373064 in combination with the presence or absence of at least 1, at least 2, at least 3, at least 4, at least 5, at least 6, at least 7, at least 8, at least 9, at least 10, at least 11, at least 12, at least 13 or all of the biomarkers (except SNP rs28373064) provided in Table 1 is determined. For example, the combination of the presence or absence of SNP rs28373064 in combination with the presence or absence of at least 1, at least 2, at least 3, at least 4, at least 5, at least 6, at least 7, at least 8, at least 9, at least 10, at least 11, at least 12, at least 13 or all biomarkers selected from the group of biomarkers having SEQ ID NO: 2 to 15 is determined.

In one embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 is indicative for a treatment response to a CRHR1 antagonist and/or a V$_{1B}$ receptor antagonist. In another embodiment the absence of SNP rs28373064 in combination with the absence of SNP rs13099050, SNP rs7441352 and SNP rs12424153 is indicative for a treatment response to a CRHR1 antagonist and/or a V$_{1B}$ receptor antagonist. In a specific embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153 is indicative for a treatment response to a CRHR1 antagonist and/or a $V_{1B}$ receptor antagonist.

In specific embodiments, the group of biomarkers whose presence or absence is determined in a method according to the present invention further comprises biomarkers as described in WO 2013/160315. For example, these additional biomarkers may be selected from the group consisting of SNP rs6437726, SNP rs1986684, SNP rs7380830, SNP rs3903768, SNP rs7325978, SNP rs13585, SNP rs9368373, SNP rs10935354, SNP rs8095703, SNP rs10206851, SNP rs9542977, SNP rs4942879, SNP rs9542954, SNP rs1593478, SNP rs9542951, SNP rs2188534, SNP rs12524124, SNP rs4352629, SNP rs7448716, SNP rs11873533, SNP rs10062658, SNP rs12547917, SNP rs1038268, SNP rs2375811, SNP rs1352671, SNP rs364331, SNP rs1924949, SNP rs11025990, SNP rs3758562, SNP rs10156056, and an SNP in strong linkage disequilibrium with any of the foregoing SNPs.

In some embodiments, the group of biomarkers whose presence or absence is determined in a method according to the present invention further comprises SNP's selected from the group consisting of SNP rs6437726, SNP rs1986684, SNP rs7380830, SNP rs3903768, SNP rs7325978, SNP rs13585, SNP rs9368373, SNP rs10935354, SNP rs8095703, SNP rs10206851, SNP rs9542977, SNP rs4942879, SNP rs9542954, SNP rs1593478, SNP rs9542951, SNP rs2188534, SNP rs12524124, SNP rs4352629, SNP rs7448716, SNP rs11873533, SNP rs10062658, SNP rs12547917, SNP rs1038268, SNP rs2375811, SNP rs1352671, SNP rs364331, SNP rs1924949, SNP rs11025990, SNP rs3758562, and SNP rs10156056, wherein the SNPs have nucleotide sequences (together with flanking sequences) as disclosed in WO 2013/160315 and shown in Table 2 below.

TABLE 2

SNPs (together with flanking sequences) which may be used to predict the response to CRHR1 antagonists and/or $V_{1B}$ antagonists in patients with depressive symptoms and/or anxiety symptoms. The position Utile SNP is indicated in bold as [wild-type allele/mutated allele] The sequence listing and the corresponding SEQ ID NOs relate to the wild-type allele.

| SNP_ID | SEQUENCE |
| --- | --- |
| RS6437726 SEQ ID NO. 16 | CAAGAAAGAGAGTAATAAAAATAACCACAATGAGGGCTCTCATTAA TACTGGATCTTATGGAAACCAATTGTTCAGTCCCTCAACAAAAGAC CAGATGGGCAGGAAGCTAAATATACACCATGCACTAAACATTATGA GTATCATAGTTTACAAGTCAAAGGGGGCTCTATTGAAGATAGTTCT ATTTTCCCTCTATATT[A/G]TCTGCTAGACAATACCTGATAACATTAT CCAAGTAAATGACAACTTGATAAATAGTAATTTCCAATGGTGAACA GAGGTGACATTTCCTCATTACAAAAATATTTTCTTTGGCAGATGAGA TTAACTGAATAAGAAATCCACTGACACTGAAATCACAGAGCCAAAT TCCCTATCACAGCACTTATCACATTGCGTTAGG |
| RS1986684 SEQ ID NO. 17 | TTCCTTGTAGCGGGGAGAGAGACTCAGGGAAGGCAGGGTGATAC CTGAGTTGGGGCTTAAAGCAAGGTAGGGTGTGTGGTGATGGCA AAATAGGTAGGAAGACAGCACGGGCAAAGTCCTGGAGGCAAGGA CAGAAAGAGGAAGTGGCAGGAAGTGAGGCTGGGGAAATGAGTAG GGGTCAATCATGATGTTTCTGGT[A/G]TAGGGAAGAGTTTGGAATG CATCCTCTAGGCCATACGCCATTGGGGGCTTTTAAGAAAGACAGT GATGTTGGTTTGATTTGCATTTTATATAGACTTTTCTGGCAGCTGAG AGGAAGGTGGTTTTGAGAATCACAAAGCTGCGGGAAGATCAGTCA GGAGGGTTCTAGAATAATCCAGGCAAGAGCTGATGGGGACTGAG |
| RS7380830 SEQ ID NO. 18 | ACAGGGGTGGCTACTCTTTCTCCAGAAATAGGTGTCCTGTGGGGC ATTTTGAAGTAGAATGTTGATAGTTGCTTTCAATTTTAGACTGGTAA ATAAGAATTGGGCATTTGAATTTCAATATACTCACTGTGTAACTGTT ATTGAGTATGCTTTAAGTGACCTATAATACTGCTTCATTTAACTTTAT TGTCCTAATAACT[C/T]TCTTAGAGTGACAATAACTTAGGTTAGCCA CTTGCCTAGGGTTCTGAAACCAAGTAAATGGTGGAGCTGGAATTG CTGTTCTTGTCAGTCATTAGACTAGATCGGTTTTCTTCTTCCTACAA ATTTTATATACTAAAAAATTTTGAGACATTTTTCTTTGGGAAA AATAGGGAATGTCAGATCCCTTTGGAGATG |
| RS3903768 SEQ ID NO. 19 | CTCGCAGCAACCAAGCCTGCCCAAGCCGGGGAAACCTGGGGAGC AAACCTTCACCTGCACTGTACATCAGAGACCAGTTGGCCCTATTTT GGCTCCTGTGGACAGGTAAGTATCCCTTTTGACTCATCCCCCAAAT ATCAGGTGAGCCAGGAAAATAAGGCCTTTGGCTTAGACAGTCAATT CAAAGTCTGCCATAGCAT[A/C]CCTAATTACATCCCTATTGCCCCTT TTCTAGGTCGTTTCTCCTCTAACACGATTTTATTTTTCTGTCAGCCA TTTTATTTTATTTCTCACCTTGAAATATATGTTTTCTTTGCAGTTTTT GCTTTGGCTTCCTGCTAACTCTATTTGGGCAATTGTTTAAGGCTGA ACACTTGGTTATGAGAGGTACCCTGTTGTGTTGA |
| RS7325978 SEQ ID NO. 20 | TCATCAAGTCTCCTTTTTCTCTAGGAAAAATAACATTGTCAAGGTTA TTAACAGTCAATAAGCTGTCATAGGCTCAGCATGGATGGGGATATT GGGTTTCCTTGTGCTTATATGAAAGATGGGAAAATCCGAAGTTCTT TTCACCCTGATATGGAAAATACCCAACATGAGGAGAAGCAGCAGC TATATGATTCTGAGCA[C/T]AGAATGGGAGTAAGAATAGGGTCATG CTGTACTGATTATCTGCTAATAAAATGCAAAAGTGTTAGGTAATTTC |

TABLE 2-continued

SNPs (together with flanking sequences) which may be used to predict the response to CRHR1 antagonists and/or V$_{1B}$ antagonists in patients with depressive symptoms and/or anxiety symptoms. The position Utile SNP is indicated in bold as [wild-type allele/mutated allele] The sequence listing and the corresponding SEQ ID NOs relate to the wild-type allele.

| SNP_ID | SEQUENCE |
|---|---|
| | ATCAATATCCAGTTAATACTAATATAGTTAATATTTCATGACTGGGT<br>AATATTTTATAATGATAAATATTTTTATAGATCTTAGCTCTTTTTATTC<br>TCATATCAACTGTATGAAATCAGTGATTGGT |
| RS13585<br>SEQ 10<br>NO. 21 | CTGGGGACCTCAGGGAGAGGTACGCAGGTTGCCATGGCTGCGTC<br>TGCAGTCCACCTGCCTTTCCACGCCAGGGAGTCAGTGATGTGGAG<br>CCCCCTGGGCCCCAGTGGAAGCAGCGATCAGACTATGTGTCCTTG<br>AAATAATGTTTATTCCACGCTGTCCCGACAGCCCCCTCTGCAGGTC<br>CCCT[C/T]GGTGTACTCTGAGGTGGGAAACCCTCCCTGGGGCGG<br>TGAAGGGGAACTCGGGCCACCCCACCAGCCAGCAGATGCTCCAG<br>CAGCCAGAGCCCCAGCCTGGAGCTGAGGCTCTTCCTGGGGCTCG<br>CCGGGCCCCTGCAGGCTTTTCGGACCCTCAGCCAGCCCGGCTTC<br>CTCTGCTTTGGGCAGCAGCAAGCTGGCCCTT |
| RS9368373<br>SEQ ID<br>NO. 22 | TTCCTGTGCCTCAGCTCCTCTGTAGAATGGTGCTGGCAATACAGTT<br>TGCCTCATTGGGCTCTTGTAAGCTTTAAATAGGTTATTATACATAAA<br>GAGCTAATAGTGATGCCTGTAGCCGTTGTCTAAGTGCTAGCTCTGA<br>TGATGGTGACAAAGAAGTAATAGCAATCAGTGGTTTAGATTAAACC<br>ATTTTAGGCATAAAC[C/T]GTTCTGCTAGAATCCAAGGGGAGATTTT<br>TTCCCATCAAGGAGACATAGCTTGTTGGGAAGATAAGACATACCCA<br>ATTGCAGAAGTAATTAATTAATTCTTTTTTTTTTTTTTTTTTTTTT<br>GCGATGGAGTTTCGCTCTTGTTGCCCAGGCTGGAGTGCAATAGCA<br>TGATCTCGGCTCACCACAACCTCTGCCTCCT |
| RS10935354<br>SEQ ID<br>NO. 23 | ATAGGCCCTATACAGCTCTCAATTTCTTTAATCAATCTTCCTAGCAG<br>CCCGTGAGAAATATTACTGTCTTCAGCTTCCTAAAGGAGAAAACAG<br>AGGCCTGGAGGGATTAAAAGACTTTTCTAAGATTTTAGAGGGCATG<br>TTAGGGTTCAGGCCCAGGGCTGTCTAACCCAAGGCCTAATTCCTT<br>CTATTACATCCATCAT[A/G]CATGAGTGAGCACTGGGCATGAGGAT<br>ACGTCAGTGAAAGGGGCCCTGTAACATGGACCTTACATTTTGGCT<br>GGGGGAGACAGGCAATGAATACATAGGACCATGTTGGGAAGTGCT<br>AAGTACTCTGATGATAACACAGCAGGGTGAGGTGACAGAGGTCTA<br>GGGAGAGTGGTGTTCAGCAAAAACTTCTCTGGGGAGAGA |
| RS8095703<br>SEQ ID<br>NO. 24 | AAAATTTACCAGGTTTAAAAAAAAAAAAACTCAAATGATATTTCAGA<br>AACCTACCCCTTTCAAAACAAGGAGGAGAAAAATCTTCTCCACAAA<br>AGCACATATTGAAAAAATATTTTGGGGGCAAGGCCTGAAAGGGTTG<br>GCAGTGTGCAGTTCTGTTATTATTCCCGTGGCCATTTTATGGGCCT<br>CAGCAAAACACTGGG[A/G]TCATTATCTGTCTTCTGGTTACTCCAG<br>GAGAGCTAGCCATCACAACCCAATGGAAGAGACTTCAGAGAAACC<br>CACACAGGCACCAGAAGTCCTTCCCTTTCATCTGCCACTGTGGGG<br>TTTTGTCCTCATCTATTACAATGTTGTCCAATCTCAGACTGCATTCA<br>GAACAAAGGCTCTCAGACTGAGGATGAGTTCTTGGA |
| RS10206851<br>SEQ ID<br>NO. 25 | CCAAATAATTGTTATTGTTGTTTTAACATGGCAATCACGTTATTTGC<br>CATATGTGAAAAGAATATTTAAATGCTTTTTAAAACTATGTATGTA<br>AAAGAATGTTTAAATTGTTTTAAAAATATGTTATATCTACCTTGGCAC<br>CATCCTTGCTGTTGAGAAATGACTTTTACCTGCTTACTTAGAAGGA<br>AATGTCAGAAG[C/T]AGAAGTACATTTGAATACGATTATTTGAAAGC<br>TTCATCCATTTTTCAAAGAATGTATACAGTAACACTAAATAGAAAGC<br>ATAGTTTATCAACTCTTCACTAAGAACAGTCTAGCAAGTATATCAGA<br>GTGGCTGTGGTTCCAGTTGGACTAACCTAATCATTTATGAAAAGGT<br>GATAATAAGCTTGGACCAAGAGCACCCA |
| RS9542977<br>SEQ ID<br>NO. 26 | CAGATGTTATGTGAAACTCTGGAGAAATAGTAGCAAGCAAGACTCA<br>CATGCCTCCTGCCCTCACAGAGCTCCATGATCTGGTGAAAGTGCC<br>AGATATTTAAACCCATGGATGTGTGCACACAAAATAACAATTCTCTC<br>AAGCGTTGTGAAGAAAAGTCACAGAGCACTACAAAAGCATGTAAGA<br>GTGAGGCAAAACCTAT[C/T]GTGTTAGGACAGGGAAGGCTTCTGTG<br>AGCTAACCTGAAGGATGAGTAGGGGTGAGCCAGATGAAAAGGCGA<br>GAGAAAAACATTCTGAGCAGAGACTGCCACTGAGTGCATCCCAGT<br>TTTCCCAACATCTTAACACTGTATAATGACTACACTGGATTTTCTTC<br>ATCCTGGATCCATGGTTAGACATGTTAATATGCCTTC |

TABLE 2-continued

SNPs (together with flanking sequences) which may be used to predict the response to CRHR1 antagonists and/or $V_{1B}$ antagonists in patients with depressive symptoms and/or anxiety symptoms. The position Utile SNP is indicated in bold as [wild-type allele/mutated allele] The sequence listing and the corresponding SEQ ID NOs relate to the wild-type allele.

| SNP_ID | SEQUENCE |
| --- | --- |
| RS4942879 SEQ ID NO. 27 | CCCAGTCTGTGGTATTTTTTTATAGCAGCACAAACAGACTAACACA AGAGGTGGATAGGATTTGCGAGCATGGACCTTGGAGGTTTGTGGC CTCAATTTAAAGTGAGTACATTCACCCAGCTGGTGTTTTTCTCTTGC TGCTTGGGCACAGAGATGGAGTAAATGGGTCTAATCAAGGATAAA GGGAGAGCCAAAGAGAT[A/G]GTAATATTTGAAAGGAAGTGTTTTT AATGATGTGCCATGTAATCTGAGGTGGGTCAGGAATGAAGTGAAAA ACTAAGAGATGATGGATGATGATAGGGGCTGTGAAAGGAAAACAA ATCTTGGGGCCCCCAAATCACTAAGCTAAAGGAGAAAGTCAAGCT GGGAACTGTTTAGGGCAATCCTGCCTCCCATTTTATTCA |
| RS9542954 SEQ 10 NO. 28 | TATTACTGCTGAGAAAACTGGGTTTGATAAACTAAAGATGCCCATG TATATCAGTCATGCTCCTGGTGAGAACAGGTGGCTCACTGCATAAT GAGAGGAATATTCAATTAACTATTTACAAAGCTATGGATGACATGTA GGGAAGCCACAGAGAGAGTACAGTATCTAGAGCTAGTAAGAGTAG AAGGCCATCACTGTCC[A/C]CAGGCCTAAAGGAGGTAGAGCAGTC AAAGGAAACAAGAGACAAGGGAGGCTGCGAGGACAGGGCCACCT GGCAGAGCCATAACCTTAAACTAGGTAGTCACTTCTTGGCAACTCT GCAGGTAGGGAGCCAACCTCACTTTTAACCCTCCCTCTGATGCCC AGCTGGTTTACCCCATTGGTGAAAATCAGTGGGTGAGGGA |
| RS1593478 SEQ ID NO. 29 | CATGAAAAGATACTTAACATTGTAACATCTTTGCATTAGGGAACTGC AAATCAAAATCATAACAAAATAGTACTGCATGCTCATTAGGATGACT ATAATCCAAAAGAATAAAAAAGAAAATAACAGGTGTTGGTAGGGAT ACAGATATAGAGAAACTGGAGCTCTCATGCCTTGCTGGGGGGCAT GTAAAATGATTCTGC[C/T]GCTTTGGAAAACAGTTTGGTGGTTCCTC AAAAAGTTAAACATATAATCCAACAATTCCACCCAAAAGAATTGAAA GCAGGGTCTAGTACACCAACGTTCATAGCAGCTTTATTCACATCAA GCCAAAGGTGGAAGCAGCCCAAATGTCTACTGATGGATGAGTTGA TACACAAAATGTGGTATATATATGCAATGGAATA |
| RS9542951 SEQ ID NO. 30 | GCCACTTGAATGCCCCAAAATGGAGAGATGGGCGTGGGAAGAGAA AGACACCTCAGCAACACAGAGCTGAGAAAACACTGTGAGTTTTATT TAATTCCTACTTACCGTTATTTTGCATAGTAAACAAAAGGGATATTT TTGAAAATCCCTTTGGATAATTTCTGCCACCTAAAATTCTGAGCATT TTGACTCACTGCCTT[A/G]TAAAAGAATCAATTAATTGAATAAGAG AAGGGATTCTCCCCTGATCTTTTCAAGAATCCTTAAAAGGCACATTT CTCACTAAGGATCTTGAAAGTGTATTTCTAGCCAATCCCAGGAGTC ACTGCTCAGAGATTTACATTTCACAAATGTAATCAACAGCCTAAGC AGAATATTGACGTTTGGACTGCAGAGCTCTGCT |
| RS2188534 SEQ 10 NO. 31 | AGGGTCCCCAAATATTTCCATTTGAGATGACAAAGTGCTCTTCAGT CATTTAGCTTACTCTTCAGTTCAGATGACTTATCATCTTGATTTCAG AGAGTTCATATATGTCTGTTTTAAAAAACTGGTTCAAAAAGTCTGAA GTTACGAAACTAAACCAAATATGCATTACTCTCATGTCAAATTACAA GCTCTTAGCTGC[G/T]GGGATTTTTTCACATGCAGCCTGGAGCCCT TGAAAACCTCTGTTTTCTGTTAGACTCTCCAGGGTACACAGAAGTT GCCTCATTATTTTAGTTAATGGTGACTGCAAATAAGCCCCCCAAGT CATTTAACTATGTGCTTACCACTGCTTTAAAAGAACCCCAAGTTAG GTCCTCATGTAGGTAAAGGAGCTCCCTTCACA |
| RS12524124 SEQ ID NO. 32 | ACTTGGGCCCAAAGGCATTCAACTAGAAAGCTGGTAATAATAACAG CGACAGTTTATTGAGTCTTAGTGTTTCTGAGAACTTTTCTAAGTACT TTACACATATTAAATTTTTAAATCTTCACATTAGTCCTGTGAGGAAG GTACTATTGTTATGTCTGTATTACCCATGGGGATACTGACGCACAA AGAAGTCAAGTAAT[A/G]TATTTAAGATTCTAGTAAGTGCAGAGCCC AGGTGCATGCAGTGCCTGGGCTCTGCCACCCATGCAGTGCTGACT AGGGCTTCCACCCATGGATTTTTTTTTTTTTTTTTTTTTGAGACA GAGTTTCGCTCTTGTTGCCCAGGCTGGAGTGCAATGGCATGATCT CGGCTCACCACAACCTCCGCCTCTCGGGTTCAA |
| RS4352629 SEQ 10 NO. 33 | CCCATAATAATGAAGGATTGGACCTGATAATCTATCAGGTACATTTT AGCCTGAAATTTATTTGTACACACGCACAAACACAGACATGTGCAC ACACACATACACATATATATATAACATTTATAAATTTTAAAACATAAA GCTATACTAGAAATGAAAGCTTATATATTGAACTGCCCCACCTTTCT ATTTGCAGCCAG[C/T]TACCACCCCAGTCTAATGTTTCACTTTATAT AAATTCATTTATTCTTTTACTCATTTCAAATATATGATGATGTAACTA TAAAATCAACATTTAGTCACTCTGAATAACCCAAAATAGCAAATAAT TTAAAAATCACTTCCACTTGACTTTAGAATCTATTACATGCATTGTTT TTCCAGAAAATTTACCTCATAATTAT |

TABLE 2-continued

SNPs (together with flanking sequences) which may be used to predict the response to CRHR1 antagonists and/or V$_{1B}$ antagonists in patients with depressive symptoms and/or anxiety symptoms. The position Utile SNP is indicated in bold as [wild-type allele/mutated allele] The sequence listing and the corresponding SEQ ID NOs relate to the wild-type allele.

| SNP_ID | SEQUENCE |
|---|---|
| RS7448716 SEQ ID NO. 34 | CTACTTATATGATTAGAGAACAAGAATACTAGGGGGAAAATCAGCA TGCATATAATCTAAGAAATTGTCATTATAATTTTAAAATCCTTTGCAA AATCAGTAAATATGAGTTTAACTTATATAATGATACACACACACACT GATATGATGCTTTATTGTCTAAACACTGGCTGCTTGTGGAGACGTA TTCTGGTAACAAA[A/G]AATATAGCATCTTAAAATTGATGCTAGCAT TGTATATCCAAATAGAGAGTAAATGCAACCAGAATATTTTTTATATG TTTAACATTGTAGTGTTGCTGACATCATTATATATTTGGTTATGTTAA TCTCAAAATGCACAATATAGCTGTATGATCTGTATAATGCAAAAAAA TGTAGAGCTTCATTTTGATATTTATTAT |
| RS11873533 SEQ ID NO. 35 | CTGGAAGGGAACAATGGAAGAGGTGCATTAGTCACATTCCAAAAT GCAGGAAGCAATAACATGTGGCACTATTGTCATTTATGTAGCACCC TAAATACTGGGACAAATGACATAGATGCCCTTCTGTGATTACTAAA CTCCCCCACAGTGTCTCAGAAGGAAGAGCTTTTGACAGGAAATCAT CAAGATCTGATGACATT[A/C]GAGAGCAATTAACATTCTCTTCAACC ATGAACTAATTGCCTCATTCACATTTTTCTAGCCATCCTAGGAAGCA GATAATAAGCAGCAATTGTCCTGCCCAGGAATTCTGACTTGTGTAA TTTGTAAAGCTTTTCTTTGTATCTATTTCTTTCCTGTGGCCATCTTTT TGTTTTTGACTGTTTGGTAACAGTAAGTGGGT |
| RS10062658 SEQ ID NO. 36 | ATCATTCAGTATTAAGAGAGAAATGAATACATTTTCAGATATACAAG AATTCAGTTTACCTCCCACAGAATCTCTGAAAAAAATATTAGATTAC TATAGTTAAAAAGGAAAATAAAATAAGTCCTGTTAGAAATAATTGGT AAAAAAGCAAAGGTGATGAAAACTTATTGAAATATATTATTAAAGTA ATTGTTAAAAAT[A/G]TACACTAAATCTAGAATATATAAATGTAGCAG TTGTTAAGGGGAAGGGGAAATAGAAGTGGAAGAAAATGAACATTA GAACAAATGTTTAGCAGTGGGATTATTTTATTGGAAGTCTAATGTAA GAAGTATATTCTCCAGGGAGGTATTTCAAGGACATATGAATAGTAA AGGGATAATAAAACAACTCTATAAGGTAGT |
| RS12547917 SEQ ID NO. 37 | CACACACAACGCTGGGCCCAGTAAATAAGTTTTGTTETTTCCCAGG GAAAAGTTGAACAACAATGGTGAGACCAGGAAGGCTCTCCGTTCA CAGGAAATACTGTGTCACCGCTCGGCCGCAGGCTGTGTGAGGTCA CGGGCGACGCTCGGGTCACGTGTGGCGGCTCCTGTTCACAGTGC CGTGTGTGATAAACTGGGAC[C/T]TTCTGGTGAGGGGAGACTGGC GGGGGGTGGGGAGGGCAAGGAGTGGGAAAGTCGCCTATAAATGT TTAACAAAAGATCCGCAATGGGAACAGGAACTTGCATTCTTTCTTT CAATGGACAAAGCTTCCACATCAAGATACGCTTGTGTGCTGGGAC CAAATGCCACAGTGCGGCGAAACTCGTGAGCACAAGTCCTGCGT |
| RS1038268 SEQ ID NO. 38 | ACAACAGGGTATCCTAGCCCAGCAAAATTGACTCATAAATTTAATG ATCACGCAATTGGTAATTCTAAATCCAGTCAGAAGTCTACATTCTGT GTCCACAGTGTCATGTCTAGATGTTGGTCCAGTCTCCCATGGACTG TGCCTTGTTATTTGTTTTCTCTTTGCTAAGCCACATCCCCTGAGGG CTCTGTTTATGCTCA[C/T]TGCAAAATCTTTGACTTTTTAACTTACTG GGCATATTGTCTTCCTACTTTTGTTCTCTTCTGTTATTTTATTTACTT GACTCTGACATGTCTCATTCCC |
| RS2375811 SEQ 10 NO. 39 | TTTCAATGGGACTGGTTGGACAGTGGGTGCAGCCCATGAAGGGCA AGCCAAAGCAGGCCGGGGCATCACCTCACCCGGGAAGCACAAGG GGTCAGGCGATTTCTCTTTCCTAGTCAAGGGAAGCCATGGCAGAC TGCACCTGGAAAAACGAGACACTTCCACCCAAATACTGCGTTTTTC GCAAGGTCTTAGCAACTAAC[A/G]GACAAGGAGATTCTCTCCCGTG CCTGGCTCGGCTGGTCCCACACCCACGGTGACTTGTTCACTGCTA GCACAGCAGTTTGAGATCGAACTACGAGGCAACAACCTGGCTAAG GGAGGGGCATCTGCCATTGCTGAGGCTTGAGTAGGTAAACAAAGT GGCCAGGAAGCTCGAACTGGGTGGAGCCCACTGCAGCTTAGCA |
| RS1352671 SEQ ID NO. 40 | ACTTTAGGGACTTTGAGTGATGGACAACCCCCTATCAGATATCATC AGCCTGAAACATCCTTATCTTGGCATTAAATTAGAAGGAACCCCAG ACCCTGCGTACCAGAATTGTTAGAATCACAGTCTCAGTAAAGAACC AACTCCTGATCACTTCTCTAAAGGAAAGTTCTAGAAGTCTGCACAC TCTGCAGTCACTTTCA[A/C]TTCTATCCAAGTGTACACTTAGAACTC TAGAAAACACTACGGACAGTCTTCAGCCAGGTAAAGCCTAAAACCA GCAAAGAACAGGGAGAGTGAGGGA |
| RS364331 SEQ ID NO. 41 | CGGATTATCACAGTTCTCAAAAGAGGAGTATGCATTTGCTTGCTCC AATTCCTCTTCTTCTACACTCTCTTAAGCATTCCTCAACCAGTCTAA TATCTCATAGTTCCCCAAAACTGCTCTGTTCAAGACCATTAGTAAGA TCTTTGATGTTAATCTGTGGACCGTATCTCTGTCCTTATTTTACTTG AAGCCCAACAGCA[A/C]ATAAAAAAGTTGTTCTCCTCTCCTCCCTGC TACACTTTCCTTATGTGGCTTGCTGGGCTCCTCAGTCCCCTGTGAA |

TABLE 2-continued

SNPs (together with flanking sequences) which may be used to predict the response to CRHR1 antagonists and/or V$_{1B}$ antagonists in patients with depressive symptoms and/or anxiety symptoms. The position Utile SNP is indicated in bold as [wild-type allele/mutated allele] The sequence listing and the corresponding SEQ ID NOs relate to the wild-type allele.

| SNP_ID | SEQUENCE |
|---|---|
|  | AAACTCTGACATGGAGATACTGCAGACCAGTAGAAGGGCTGGGCA GACACTATACAGAAACAGTATGCCCTACATGCTCCTTGGCTAAATC TCTAGAATTTTTTTCAGAACTCATCCACAAATT |
| RS1924949 SEQ ID NO. 42 | ATTTTATCTCATTTACTTATTAAATCAAACCAATATTTTATGAAGTGA TTCCAGTATTGGAATAAAAATGTAATTCTTTAATCATTAAAAAATCTT TATGAATACCTTACATCAACTGTAGGGGACCAACCAGGGAAAAGCA GGGAGACTTGTAGAATCTACACCTCCAGAACAACCGACCTCCATCT TCTGGACAACTC[A/C]TCTTCTAAAGTGCAGGACAGACTAGTTGGG GGAGAAAGGAGGAAATGAAAGAGATAGACTAAAAGGGAGGGAGA GAACAGATATTTTTTAAGTACCTGTTATGTTCTGGATACAGCACAGA GTACATTGTATCTATTATTATAAGGCATAAAGAAAGATTTCTCAGGT TTTTGGAGTCAGATTGCAATATAAAATAATAG |
| RS11025990 SEQ ID NO. 43 | TAACTTCAAATTGTTTTGCAAAATCTCTGTCATAAAAATGCTTACCA ACAAATACTGATACTAAATTTAGATGTGGGGGTATTAGTTATAATCC TGAAGTGGGAGGGGGAACTTCTTAATTCCAATTTAGTTCTAAGAGA AGGAAGAGTATTTAGGCCCAGAGAAGGTTACGCTTAAAGGTCTGA TAGTGTTTTCTTTGA[A/G]AAATATGTCTCAAACTAGAGAATAAAACT AATTATCTCATCTAAGTTACCTAGAGACATTTATGCTCATCAGTTTG ATAAAGGACTGCAAGTAGACACAGAAGCTGTATTTTCAGTCTTGAA CCCAGCAATAGTACATTAACAAGATTGGGGCAAGGCAAAGGGACT TTTGTGGCACAAGATACAATATATGGATTGCGT |
| RS3758562 SEQ ID NO. 44 | CTCTTCAAAGGCCTTTGCCCTTGGGTACCACAGGTTCTGAGACAA GAGGGCTATGGAGAGCCCCCATTATAGCTGGAGCCTCCTGCCCTG CCCAAAGGTGTGACTTGAAGGGTGGAATTTCAGGCAGCGTGGCTC GCCCCAGGGAGGCAAAGAGGCCAGGGGAATCTTCAAAGGCCCTG GGCTCATCCCAGCTAGGAGGC[A/G]GGCACAGTCATAACCCTAAT CCAGTGAACTCAGCCCTCATCCTGACTCTCATGGTATTCTGTCCCA GGGAGCCTCTTTCCAGCTTTCTTAGAAGCTTTAATGTCAGCACTTG CAGGGCCTTAGAAACTGCACGCTACCTCTTCATTTCATACATGAGG AAACTGAGGCCCAGGGTGGACACAGGGCTGCCCAGCGAGTTA |
| RS10156056 SEQ ID NO. 45 | ATTATAAAGCAAAGCACTAACCTCATAGAATACCTGAGTCAAGTTC CCTGTGTTCTCATTTTCTAGCCTCTTCTACCAGACACTATGAAAAAT AACAGCCCCATCTCTCCAGAAAATCTTAGGAGATATAGGCGTGCTG AATTTAAGGTGTCTGTGGCACATGCAAGTGGATCAGCCACTGGGC TGTCCAGAATGCAAGA[C/G]AGAACTCAGAGTTGGGGACATAAACT TGGCAGTCATCTGTGTAAAAGAGAAAAGGTAGGTAAAGTCCCACAA GGATGGGTTGGCCTACAGAAGGCACAGAGAGAAGAGAGCCTGGT TTAGCATGGGCTACGATCAGAGTCCCTGGGTTCAAATCTTGGCTC CACCCATTTCTATCTGGTTGCTCTAGGGCATGTTACCTA |

It is to be understood that the analysis of further parameters, such as the gender of the patient in combination with the presence or absence of each of the SNPs defined in Table 1 may be added as further factors to the prediction analysis for the treatment response to a CRHR1 antagonist and/or a V$_{1B}$ receptor antagonist.

The method according to the present invention may include a further step of determining the presence of a clinical marker. Such clinical markers may include the AVP level, the copeptin level and/or the response to the combined dexamethasone supression/CRH stimulation test (combined dex/CRH test) as described herein below, whereby an elevated AVP level, an elevated copeptin level and/or an increased ACTH response in the combined dexamethasone supression/CRH stimulation test are in addition indicative for a patient showing a positive response to treatment with a CRHR1 antagonist and/or a V$_{1B}$ receptor antagonist. In addition or alternatively, a clinical marker may include a value indicative for the rapid-eye-movement (REM) density, e.g. a value indicative for the rapid-eye-movement (REM) density during a first REM night sleep episode of a patient. For example, a value indicative for the rapid-eye-movement (REM) density may be a clinical marker in a method for predicting the treatment response to a CRHR1 antagonist as described herein.

Elevated AVP levels may be indicated by an AVP concentration in the sample of cerebrospinal fluid in the range from 4 to 8 pg/ml AVP, optionally in the range from 4 to 6 pg/ml AVP. Elevated copeptin levels and therefore also elevated AVP levels may be indicated by a copeptin blood concentration in the range from 5 to 9 pmol/L, optionally in the range from 5 to 7 pmol/L.

The combined dex/CRH test has been described by Heuser et al. (*The combined dexamethasone/CRH test: a refined laboratory test for psychiatric disorders*, J Psychiatr Res, 1994, 28:341-356) and can be used for screening for compounds which may be useful in the treatment of depressive symptoms and/or anxiety symptoms. In detail, in the combined dex/CRH test subjects are pre-treated with dexamethasone (e.g. 1.5 mg dexamethasone) and blood is drawn in certain intervals after the dexamethasone treatment. This blood sample shows the suppression of cortisol by dexamethasone. The pre-treatment is normally performed in the evening prior to the day of the CRH administration. Human CRH (e.g. 100 pg CRH) is administered after the first pre-treatment with dexamethasone, e.g. 16 hours after the pre-treatment. Subsequently, blood samples are drawn (e.g. in intervals of 15 minutes) from the patient and the plasma ACTH and/or cortisol concentrations are determined. The neuroendocrine response to the dex/CRH test may be analyzed using the total area under the curve (AUC) of the ACTH response. Patients suffering from depression normally show an increased release of cortisol and of adrenocorticotropic hormone (ACTH) in response to the combined treatment with dexamethasone and CRH as performed during the test, thus indicating a dysregulation of the hypothalamic-pituitary-adrenal (HPA) axis. Patients with a high HPA axis dysregulation show AUC values of cortisol of between 3000 and 18000 AUC units (ng/ml×75 min) and/or AUC values of ACTH of between 1000 and 6500 AUC units (pg/ml×75 min). Patients having a low HPA axis dysregulation show AUC values of cortisol of between 300 and 2500 AUC units (ng/ml×75 min) and/or AUC values of ACTH of between 250 and 1000 AUC units (pg/ml×75 min). An "increased ACTH response" as used herein thus relates to an increased release of ACTH in response to the combined treatment with dexamethasone and CRH during the combined dex/CRH test, in particular to AUC values of ACTH of between 1000 and 6500 AUC units (pg/ml×75 min) which may be observed in a patient subjected to the combined dex/CRH test.

Various antidepressants may lead to a reduction of these increased cortisol and ACTH levels in a combined dex/CRH test performed after the treatment with the antidepressants. Treatment response to antidepressants can thus be determined by performing a second dex/CRH test after treatment with the antidepressant and comparing the neuroendocrine response to the one shown in a combined dex/CRH test performed prior to treatment with the antidepressant.

An increased ACTH response in the patient subjected to the combined dex/CRH test may point to a CRH overactivity in said patient, i.e. to a patient showing a positive treatment response to treatment with CRHR1 antagonists and/or $V_{1B}$ receptor antagonists.

As already mentioned above, the method for predicting a treatment response to CRHR1 antagonists and/or V1B receptor antagonists in patients with depressive symptoms and/or anxiety symptoms may be accompanied by analyzing the rapid-eye-movement (REM) during night sleep of a patient in a sleep EEG. REM sleep typically comprises a characteristic coincidence of nearly complete muscle atonia, a waking-like pattern of brain oscillations and rapid eye movements (REMs). The amount of REMs during consecutive REM sleep episodes is usually increasing throughout the night. Single and short REMs with low amplitude can be characteristic for initial parts of REM sleep. The amount of REMs in particular within the first REM sleep episode can be of clinical relevance. Recent clinical and animal data supports the correlation of REM density with an increased CRH activity. For example, Kimura et al. (Mol. Psychiatry, 2010) showed that mice overexpressing CRH in the forebrain exhibit constantly increased rapid eye movement (REM) sleep compared to wildtype mice. In addition, it could be shown that treatment with the CRHR1 antagonist DMP696 could reverse the REM enhancement. Thus, SNP analysis and REM density analysis as described herein may be combined for predicting the response of patients with depressive symptoms and/or anxiety symptoms to treatment with a CRHR1 antagonist. The REM analysis may be carried out before, concomitant or after the SNP analysis as described herein. For example, the REM density analysis may be carried out on persons that where identified by the SNP analysis as described herein as CRH hyperdrive patients.

The recording of a "sleep-EEG" (also referred to "polysomatic recordings") may comprise electroencephalography (EEG), vertical and horizontal electrooculography (EOG), electromyography (EMG) and/or electrocardiography (ECG). In EOG, muscle activities of right and left eye may be recorded by electrooculograms (one or typically two channels) in order to visualize the phasic components of REM sleep.

"REM analysis" or "analyzing the rapid-eye-movement (REM)" may refer to a method comprising recoding of muscle activities of right and left eye by EOG and then analyzing the electrooculogram. The recognition of REM in the electrooculogram may be done manually (for example by standard guidelines Rechtschaffen and Kales, 1968, Bethesda, Md.: National Institute of Neurological Diseases and Blindness).

The terms "CRH overactivity", "CRH system overactivity", "CRH hyperactivity", "CRH hyperdrive" or "central CRH hyperdrive" are used herein interchangeable. An indication for CRH overactivity may be an increase in activity or concentration of CRH or of one or several molecules downstream of the CRHR1 receptor, that are activated or whose concentration is increased based on the activation of CRHR1 receptor upon CRH binding. A further indication for CRH overactivity may be a decrease in activity or concentration of one or several molecules downstream of the CRHR1 receptor, that are inactivated or whose concentration is decreased based on the activation of CRHR1 receptor upon CRH binding. A value indicative for CRH overactivity is usually considered to be indicative or predictive for a patient responding to a treatment with a CRHR1 antagonist or a $V_{1B}$ antagonist. Normal CRH activity vs. CRH overactivity may be defined relatively to the whole group, e.g. by using a median split of the area under the curve of the ACTH response in the dex/CRH test. Responses in the upper median may be categorized as being predictive of CRH overactivity, while responses in the lower median are indicative of normal CRH activity.

The at least one polymorphic variant in the patient's genome may be obtained by a genome wide screening for polymorphic variants in a patient having depressive symptoms and/or anxiety symptoms and by identifying at least one polymorphic variant associated with increased ACTH response to a combined dexamethasone supression/CRH stimulation test (combined dex/CRH test) in the patient and, optionally showing an interaction with a polymorphic variant in the AVPR1B gene, in particular with SNP rs28373064.

The terms "treatment response to a CRHR1 or $V_{1B}$ receptor antagonist in patients with depressive symptoms and/or anxiety symptoms" or "positive treatment response" as used herein refers to a response in a patient with depressive symptoms and/or anxiety symptoms during and/or after the treatment with one or more CRHR1 or $V_{1B}$ antagonists compared to the state before the treatment. The response may range from a partial alleviation of the symptoms to a complete remission of the symptoms, indicated by the change of symptoms strength and/or frequency of relapse of individual symptoms and/or the mean change on a depression scale, e.g. as described herein. Accordingly, a patient responding to the treatment with CRHR1 or $V_{1B}$ receptor antagonists shows any of the responses to the treatment with CRHR1 or $V_{1B}$ receptor antagonists. The response can occur shortly after treatment or after a certain time period. A decrease in symptom severity from pre-treatment of 25% or more is usually considered a partial alleviation of symptoms. Remission may be defined as achieving a value of 8 or less, e.g. 7 or less, on the Hamilton Depression Rating Scale (HAM-D) or equivalent values on other rating scales named herein.

The term "patient eligible for a therapy with a CRHR1 antagonist and/or $V_{1B}$ receptor antagonist" as used herein may refer to a patient with depressive symptoms and/or anxiety symptoms who shows, or is predicted to show, a positive treatment response during and/or after the treatment with one or more CRHR1 or $V_{1B}$ antagonists compared to the state before the treatment.

Depressive symptoms comprise inter alia low mood, low self-esteem, loss of interest or pleasure, psychosis, poor concentration and memory, social isolation, psychomotor agitation/retardation, thoughts of death or suicide, significant weight change (loss/gain), fatigue, and a feeling of worthlessness. The depressive disorders can last for weeks to lifelong disorder with periodic reoccurring depressive episodes. For the assessment of depression severity (e.g. moderate or severe depression) the Hamilton Depression Rating Scale (HAM-D) (Hamilton, J Neurol Neurosurg Psychiatry, 1960) may be used. The depression mode may be also rated by alternative scales as the Beck Depression Inventory (BDI), the Montgomery-Asberg Depression Scale (MADRS), the Geriatric Depression Scale (GDS), the Zung Self-Rating Depression Scale (ZSRDS).

Anxiety symptoms comprise inter alia panic disorders, generalized anxiety disorder, phobias and posttraumatic stress disorder. Typical symptoms of anxiety are avoidance behavior which may lead to social isolation, physical ailments like tachycardia, dizziness and sweating, mental apprehension, stress and tensions. The strength of these symptoms ranges from nervousness and discomfort to panic and terror in humans or animals. Most anxiety disorders may last for weeks or even months, some of them even for years and worsen if not suitably treated. For measuring the severity of anxiety symptoms, the Hamilton Anxiety Rating Scale (HAM-A) or the State-Trait Anxiety Rating Scale (STAI) can be used.

Hence, "a patient with depressive and/or anxiety symptoms" may suffer from one or more of the above mentioned symptoms. The patient may suffer from depressive symptoms only, thus including patients suffering from only one of the depressive symptoms described herein, combinations of the depressive symptoms described herein or combinations of the depressive symptoms described herein in combination with any further symptoms pointing to a depressive disorder and not explicitly mentioned herein. Also, the patient may suffer from anxiety symptoms only, thus including patients suffering from only one of the anxiety symptoms described herein, combinations of the anxiety symptoms described herein or combinations of the anxiety symptoms described herein in combination with any further symptoms pointing to an anxiety disorder and not explicitly mentioned herein. The patient may also suffer from depressive and anxiety symptoms, in particular combinations of the depressive and anxiety symptoms mentioned herein. In particular, a patient suffering from depressive and/or anxiety symptoms denotes any person having a score of above 7 according to the Hamilton Depression Rating Scale and/or a score of above 6 on the Montgomery-Asberg Depression Scale and/or a score of above 44 on the Zung Self-Rating Depression Scale and/or a score of more than 14 on the Hamilton Anxiety Rating Scale. In addition, or alternatively, a patient suffering from depressive and/or anxiety symptoms denotes any person having a score considered to be pathologic in any of the known scales for assessment of depression and/or anxiety.

In contrast, a "healthy individual" as used herein, denotes any person not suffering from anxiety and/or depressive symptoms. In particular, a healthy individual denotes any person having a score of 0-7 according to the Hamilton Depression Rating Scale and/or a score of 0-6 on the Montgomery-Asberg Depression Scale and/or a score of 20-44 on the Zung Self-Rating Depression Scale and/or a score of less than 14 on the Hamilton Anxiety Rating Scale. In addition, or alternatively, a healthy individual denotes any person having a score considered to be normal in any of the known scales for assessment of depression and/or anxiety.

Another aspect of the invention concerns the provision of an algorithm for predicting a treatment response to CRHR1 antagonists and/or $V_{1B}$ receptor antagonists in patients with depressive symptoms and/or anxiety symptoms. The method may comprise the following steps:

(a) performing a single nucleotide polymorphism (SNP) genotyping analysis in a group of patients with depressive symptoms and/or anxiety symptoms;

(b) determining a value indicative for CRH activity in each patient of the group, wherein a value indicative for CRH overactivity is indicative or predictive for a patient responding to a treatment with a CRH1 antagonist and/or $V_{1B}$ receptor antagonist:

(c) determining whether the presence or absence of at least one SNP and/or the combination of the presence or absence of at least two SNPs is associated with a value indicative for CRH overactivity as determined in step (b);

(d) determining the algorithm by machine-learning from the association of the presence or absence of the at least one SNP identified in step (c) with the value indicative for CRH overactivity and from the association of the combination of the presence or absence of at least two SNPs identified in step (c) with a value indicative for CRH overactivity.

One embodiment of the invention concerns the provision of an algorithm for predicting a treatment response to $V_{1B}$ receptor antagonists in patients with depressive symptoms and/or anxiety symptoms. The method may comprise the following steps:

(a) performing a single nucleotide polymorphism (SNP) genotyping analysis in a group of patients with depressive symptoms and/or anxiety symptoms;

(b) determining a value indicative for CRH activity in each patient of the group, wherein a value indicative for CRH overactivity is indicative or predictive for a patient responding to a treatment with a $V_{1B}$ receptor antagonist;

(c) determining whether the presence or absence of at least one SNP and/or the combination of the presence or absence of at least two SNPs is associated with a value indicative for CRH overactivity as determined in step (b);

(d) determining the algorithm by machine-learning from the association of the presence or absence of the at least one SNP identified in step (c) with the value indicative for CRH overactivity and from the association of the combination of the presence or absence of at least two SNPs identified in step (c) with a value indicative for CRH overactivity.

In a step (a), a single nucleotide polymorphism (SNP) genotyping analysis in a group of patients with depressive symptoms and/or anxiety symptoms is performed.

A "group of patients" as used herein comprises at least two patients, such as at least 10 patients, or at least 100 patients, or at least 150 patients. Patients included in the analysis of step (a) may exhibit at least a moderate to severe depressive mode. The group of patients may comprise patients with CRH overactivity and/or patients with normal CRH activity.

SNP genotyping analysis can be performed by methods known in the art such as microarray analysis or sequencing analysis or PCR related methods or mass spectrometry or 5'-nuclease assays or allele specific hybridization or high-throughput variants of these techniques or combinations thereof. These and other methods are known in the art. See for example Rampal, DNA Arrays: Methods and Protocols (Methods in Molecular Biology) 2010; Graham & Hill, DNA Sequencing Protocols (Methods in Molecular Biology) 2001; Schuster, Nat. Methods, 2008 and Brenner, Nat. Biotech., 2000: Mardis, Annu Rev Genomics Hum Genet., 2008. Genomewide arrays can be purchased from different suppliers such as Illumia and Affymetrix.

For example, the determination of the nucleotide sequence and/or molecular structure may be carried out through allele-specific oligonucleotide (ASO)-dot blot analysis, primer extension assays, iPLEX SNP genotyping, dynamic allele-specific hybridization (DASH) genotyping, the use of molecular beacons, tetra primer ARMS PCR, a flap endonuclease invader assay, an oligonucleotide ligase assay, PCR-single strand conformation polymorphism (SSCP) analysis, quantitative real-time PCR assay, SNP microarray based analysis, restriction enzyme fragment length polymorphism (RFLP) analysis, targeted resequencing analysis and/or whole genome sequencing analysis.

In some embodiments, any of the methods described herein comprises the determination of the haplotype for two copies of the chromosome comprising the SNPs identified herein.

Typically, a SNP is considered in the genotyping analysis if it occurs in a certain percentage in the population, for example in at least 5% or at least 10% of the population. In other words, the minor allele frequency (MAF) is larger than 0.05 or 0.10 (MAF>0.05 or MAF>0.10).

For the SNP genotyping analysis a nucleic acid or DNA sample from a patient may be used. The nucleic acid or DNA sample can be a blood sample, a hair sample, a skin sample or a *salvia* sample of the patient. Any other sample obtainable from the patient and containing patient nucleic acid or DNA can also be used. The sample can be collected from the patient by any method known in the art. For example, a blood sample can be taken from a patient by use of a sterile needle. The collection of *salvia* out of the mouth and throat of the patient can be performed by use of a sterile cotton bud or by flushing said area and collecting the flushing solution.

Usually, the nucleic acid or DNA is extracted or isolated or purified from the sample prior to SNP genotyping analysis. Any method known in the art may be used for nucleic acid or DNA extraction or isolation or purification. Suitable methods comprise inter alia steps such as centrifugation steps, precipitation steps, chromatography steps, dialyzing steps, heating steps, cooling steps and/or denaturation steps. For some embodiments, a certain nucleic acid or DNA content in the sample may be reached. Nucleic acid or DNA content can be measured for example via UV spectrometry as described in the literature. However, in alternative embodiments SNP genotyping analysis may also be performed by using a non-extracted or non-purified sample.

Nucleic acid or DNA amplification may also be useful prior to the SNP analysis step. Any method known in the art can be used for nucleic acid or DNA amplification. The sample can thus be provided in a concentration and solution appropriate for the SNP analysis.

The analyzed SNPs may be represented by values 0, 1 or 2. The value "0" may indicate that the SNP is present on none of the two homologous chromosomes. The value "1" may indicate that the SNP is present on one of the two homologous chromosomes. The value "2" may indicate that the SNP is present on both homologous chromosomes. Homologous chromosomes correspond to each other in terms of chromosome length, gene loci and staining pattern. One is inherited from the mother, the other is inherited from the father.

In a step (b) of the method for providing a prediction algorithm, a value indicative for CRH activity in each patient is determined.

A "value indicative for CRH activity", a "value indicative for CRH overactivity" and/or a "value indicative for normal CRH activity" can be obtained by determining the concentration or activity of CRH and/or of a downstream target of the CRHR1 receptor. The analysis is usually set up in a way that it can be excluded that the modulation of activity or concentration of a downstream target of the CRHR1 receptor is due to another disturbance than CRH activity. For instance, the concentrations or activities of adrenocorticotrophin (ACTH) and/or cortisol are useful biomarkers for determining a value indicative for CRH overactivity. Typically, the CRH overactivity in each patient may be determined by measuring the ACTH and/or cortisol level response to a combined dexamethasone suppression/CRH stimulation test as described herein.

Steps (c) and (d) of the method for providing a prediction algorithm may analyze the association of the analyzed SNPs with the value indicative for CRH overactivity and/or normal CRH activity and generate an algorithm for predicting the treatment response to CRHR1 antagonists and/or $V_{1B}$ receptor antagonists. In addition or alternatively, steps (c) and (d) of the method for providing a prediction algorithm may analyze the association of a combination of the presence or absence of at least two of the analyzed SNPs, in particular a combination of the presence or absence of at least one SNP in the AVPR1B gene with the presence or absence of at least one SNP in the genome of the patient excluding the AVPR1B gene with a value indicative for CRH overactivity and/or normal CRH activity and generate an algorithm for predicting the treatment response to CRHR1 antagonists and/or $V_{1B}$ receptor antagonists. Additionally, steps (c) and (d) of the method for providing a prediction algorithm may analyze the association of the gender of the patient from which the sample was derived with a value indicative for CRH overactivity and/or normal CRH activity and generate an algorithm for predicting the treatment response to CRHR1 antagonists and/or $V_{1B}$ receptor antagonists.

In an exemplary embodiment, the group of patients may be split into two sets of similar size and similar values for descriptors such as demographic descriptors or clinical descriptors. These two sets are hereinafter also referred to as "training set" and "test set".

In step (c) of the method of this exemplary embodiment, at least one SNP associated with the value indicative for CRH overactivity and/or normal CRH activity as determined in step (b) is identified in the training set. In addition or alternatively, in step (c) the association of a combination of the analyzed SNPs with a value indicative for CRH overactivity and/or normal CRH activity as determined in step (b) may be identified in the training set. Optionally, in step (c) the association of the gender of the patient from which the sample was derived with a value indicative for CRH overactivity and/or normal CRH activity as determined in step (b) is identified in the training set.

Further, there can be at least two alternatives for the result provided by the prediction algorithm. First, the result may be a categorical answer whether the patient responds to CRHR1 antagonist and/or $V_{1B}$ receptor antagonist treatment or not. Second, the prediction algorithm may provide the answer to which degree or likelihood the patient may respond or may not respond to the treatment. Depending on the desired result provided by the prediction algorithm the way of determining the algorithm may differ.

In the alternative the prediction algorithm will analyze whether a patient responds or does not respond to CRHR1 antagonist and/or $V_{1B}$ receptor antagonist treatment, the values indicative for CRH activity may be provided as logic data variable (e.g., Boolean type; 0 vs. 1; true vs. false, high vs. low responder). Therefore, if the test performed to determine values indicative for CRH overactivity provides a data range, the patients may be dichotomized by a threshold into high vs. low responders.

In the alternative the test will analyze to which degree or likelihood the patient may respond or may not respond to the CRHR1 antagonist and/or $V_{1B}$ receptor antagonist treatment, the values indicative for CRH activity may be provided as numerical values.

Typically, SNPs that are modified in a significant percentage of the population are used in the method for providing a prediction algorithm. For example, only SNPs with a minor allele frequency (MAF) greater than 0.05 or 0.10 may be selected for further analysis. This means that only SNPs that are modified in at least 5% or 10% of the population are selected for further analysis.

Association for all SNPs or combinations of SNPs with the value indicative for CRH activity is tested by an association analysis testing the likelihood for a patient to be CRH overactive vs. CRH non-overactive in dependence of the genotype of said patient. Said association analysis may be conducted for example by an additive genetic model and/or by a logistic regression. An SNP and/or a combination of at least two SNPs is e.g. identified to be associated with a value indicative for CRH overactivity if the corresponding p-value is less than $1\times10^{-3}$ or less than $1\times10^{-4}$ or less than $1\times10^{-5}$. The lower the p-value the more the SNP or the combination of at least two SNPs is associated with a value indicative for CRH overactivity. Accordingly, an SNP or a combination of at least two SNPs is e.g. identified to be associated with a value indicative for normal CRH activity if the corresponding p-value is at least $1\times10^{-3}$ or at least $1\times10^{-4}$ or at least $1\times10^{-5}$. In one embodiment of the invention, only SNPs or combination of SNPs with a p-value of $<1\times10^{-5}$ are used.

In step (d) of this exemplary embodiment, the algorithm for predicting a treatment response to CRHR1 antagonists and/or $V_{1B}$ receptor antagonist may be determined by the use of SNPs or combination of SNPs in the test set by a machine learning method.

The term "algorithm for predicting" as used herein may refer to a classification function (also known as binary classification test).

The term "machine-learning" as used herein may refer to a method known to the person skilled in the art of machine learning. In particular, machine learning is concerned with the design and development of algorithms that allow computers to evolve behaviors based on empirical data, such as from sensor data or databases. It may be selected from the group consisting of artificial neural network learning, decision tree learning, support vector machine learning, Bayesian network learning, clustering, and regression analysis.

The term "reliable prediction of the treatment response to CRHR1 antagonists and/or $V_{1B}$ receptor antagonist" as used herein may refer to a high performance of the prediction algorithm. The evaluation of the performance of the prediction algorithm may depend on the problem the algorithm is applied for. If the algorithm is used to identify patients that are likely to respond to the treatment with CRHR1 antagonists and/or $V_{1B}$ receptor antagonists the performance is usually expressed by a high accuracy and/or sensitivity and/or precision. If patients should be identified which are likely not to respond to the treatment with CRHR1 antagonists and/or $V_{1B}$ receptor antagonist, specificity and/or negative predictive value are typical statistical measures to describe the performance of the prediction algorithm.

For optimizing the prediction performance of the algorithm, the step of determining the algorithm by a machine-learning method in a first subset of the test set and testing the prediction performance in an second independent subset of the test set may be repeated based on different numbers and groups of SNPs, until the desired prediction performance is reached.

Accuracy, sensitivity, precision, specificity and negative predictive value are exemplary statistical measure of the performance of the prediction algorithm. In the following, examples are given for determining the performance of the prediction algorithm.

As used herein, accuracy may be calculated as (number of true positives+number of true negatives)/(number of true positives+number of false positives+number of true negatives+number of false negatives), e.g. (number of patients correctly diagnosed as responding to CRHR1 antagonist and/or $V_{1B}$ receptor antagonist+number of patients correctly diagnosed as not responding to CRHR1 antagonist and/or $V_{1B}$ receptor antagonist)/(number of patients correctly diagnosed as responding to CRHR1 antagonist and/or $V_{1B}$ receptor antagonist+number of patients wrongly diagnosed as responding to CRHR1 antagonist and/or $V_{1B}$ receptor antagonist+number of patients correctly diagnosed as not responding to CRHR1 antagonist and/or $V_{1B}$ receptor antagonist+number of patients wrongly diagnosed as not responding to CRHR1 antagonist and/or $V_{1B}$ receptor antagonist). The accuracy of prediction may e.g. be at least 60%, at least 70%, at least 80% or at least 90%.

A used herein, sensitivity may be calculated as (true positives)/(true positives+false negatives), e.g.: (number of patients correctly diagnosed as responding to CRHR1 antagonist and/or $V_{1B}$ receptor antagonist)/(number of patients correctly diagnosed as responding to CRHR1 antagonist and/or $V_{1B}$ receptor antagonist+number of patients wrongly diagnosed as not responding to CRHR1 antagonist and/or $V_{1B}$ receptor antagonist). The sensitivity of prediction may be at least 60%, at least 70%, at least 80% or at least 90%.

As used herein, precision (also referred to as positive predictive value) may be calculated as (true positives)/(true positives+false positives), e.g.: (number of patients correctly diagnosed as responding to CRHR1 antagonist and/or $V_{1B}$ receptor antagonist)/(number of patients correctly diagnosed as responding to CRHR1 antagonist and/or $V_{1B}$ receptor antagonist+number of patients wrongly diagnosed as responding to CRHR1 antagonist and/or $V_{1B}$ receptor antagonist). The precision of prediction may be at least 60%, at least 70%, at least 80% or at least 90%.

As used herein, specificity is calculated as (true negatives)/(true negatives+false positives). e.g.: (number of patients correctly diagnosed as not responding to CRHR1 antagonist and/or $V_{1B}$ receptor antagonist)/(number of patients correctly diagnosed as not responding to CRHR1 antagonist and/or $V_{1B}$ receptor antagonist+number of patients wrongly diagnosed as responding to CRHR1 antagonist and/or $V_{1B}$ receptor antagonist). The specificity of prediction may be at least 60%, at least 700/o, at least 80% or at least 90%.

As used herein, negative predictive value is calculated as (true negatives)/(true negatives+false negatives), e.g.: (number of patients correctly diagnosed as not responding to CRHR1 antagonist and/or $V_{1B}$ receptor antagonist)/(number of patients correctly diagnosed as not responding to CRHR1 antagonist and/or $V_{1B}$ receptor antagonist+number of patients wrongly diagnosed as not responding to CRHR1 antagonist and/or $V_{1B}$ receptor antagonist). The negative predictive value may be at least 60%, at least 70%, at least 80% or at least 90%.

Other statistical measures useful for describing the performance of the prediction algorithm are geometric mean of sensitivity and specificity, geometric mean of positive predictive value and negative predictive value, F-measure and area under ROC curve, and the positive and negative likelihood ratios, the false discovery rate and Matthews correlation coefficient. These measures and method for their determination are well known in the art.

In general, a prediction algorithm with high sensitivity may have low specificity and vice versa. The decision to select an algorithm having certain statistical characteristics such as accuracy, sensitivity or specificity may also depend on the costs associated with a treatment with a CRHR1 antagonist and/or $V_{1B}$ receptor antagonist should the prediction be positive and/or whether such a treatment is detrimental in cases where the result is a false positive.

For a prediction whether a patient is likely to respond to the treatment with a CRHR1 antagonist and/or a $V_{1B}$ receptor antagonist the prediction algorithm may be based on a number of SNPs and/or combinations of SNPs sufficient to achieve a prediction sensitivity and/or precision of at least 55%, optionally at least 70% or at least 80%.

For the prediction whether it is unlikely that a patient responds to the treatment with a CRHR1 antagonist and/or a $V_{1B}$ receptor antagonist the prediction algorithm may be based on a number of SNPs and/or combinations of SNPs sufficient to achieve a prediction specificity and/or negative predictive value of at least 55%, optionally at least 70% or at least 80%.

For a prediction whether a patient responds to a treatment with CRHR1 antagonists and/or $V_{1B}$ receptor antagonists or not the prediction algorithm may be based on a number of SNPs and/or combinations of SNPs sufficient to achieve sensitivity and/or precision and/or specificity and/or negative predictive value of at least 55%, optionally at least 70% or at least 80%.

In one embodiment, a number N of SNPs and/or combinations of SNPs is associated with a value indicative for CRH overactivity or normal CRH activity in step (c) of the method for providing an algorithm, wherein N is sufficient to provide an accuracy of at least 80% and a sensitivity of at least 70% and a specificity of at least 70%. In another embodiment. N is sufficient to provide an accuracy of at least 85% and a sensitivity of at least 80% and a specificity of at least 80%. In one embodiment, a sufficient number N of SNPs and/or combinations of SNPs comprises at least one polymorphic variant in the AVPR1B gene in combination with a set or group of polymorphic variants in the patient's genome excluding the AVPR1B gene, e.g. to a combination of a polymorphic variant in the AVPR1B gene, optionally SNP rs28373064, with at least 1, at least 2, at least 3, at least 4, at least 5, at least 6, at least 7, at least 8, at least 9, at least 10, at least 11, at least 12, at least 13, or at least 14 polymorphic variant(s) as described herein, e.g. in Table 1, for polymorphic variants in the patient's genome excluding the AVPR1B gene.

In another embodiment, the presence or absence of a number M of SNPs and/or combinations of SNPs is determined in step (a) of the method for predicting a treatment response, wherein M is sufficient to provide an accuracy of at least 80% and a sensitivity of at least 70% and a specificity of at least 70%. In another embodiment, M is sufficient to provide an accuracy of at least 85% and a sensitivity of at least 80% and a specificity of at least 80%. In one embodiment, a sufficient number M of SNPs and/or combinations of SNPs comprises at least one polymorphic variant in the AVPR1B gene in combination with a set or group of polymorphic variants in the patient's genome excluding the AVPR1B gene, e.g. to a combination of a polymorphic variant in the AVPR1B gene, optionally SNP rs28373064, with at least 1, at least 2, at least 3, at least 4, at least 5, at least 6, at least 7, at least 8, at least 9, at least 10, at least 11, at least 12, at least 13, or at least 14 polymorphic variant(s) as described herein, e.g. in Table 1, for polymorphic variants in the patient's genome excluding the AVPR1B gene.

Typically, at least 2, at least 5, at least 8 or at least 11 SNPs and/or combinations of SNPs are used for determination of the algorithm in step (d) of the method for providing a prediction algorithm.

In another embodiment, the algorithm determined in step (d) associates at least one SNP selected from the group consisting of SNPs described in Table 1 and an SNP in strong linkage disequilibrium with any of the foregoing SNPs with a value indicative for CRH overactivity or normal CRH activity.

The skilled person in the art knows that the use of different machine-learning methods and adapting parameters used therein can be also used for improvement of the prediction reliability. The whole statistical work-flow can be automated by a computer.

Thus, in one embodiment the above-described method for predicting a treatment response to a CRHR1 antagonist and/or $V_{1B}$ receptor antagonists further comprises a step (iii), wherein the treatment response to CRHR1 antagonists and/or $V_{1B}$ receptor antagonists is predicted by linking the algorithm provided by the above-described method for providing a prediction algorithm with the presence or absence of at least one SNP and combination of SNPs as determined in steps (i) and (ii) of said method. In particular, said SNPs correspond to the SNPs shown herein in Table 1 and the combinations of SNPs described herein.

"Linking an algorithm for predicting a treatment response to CRHR1 antagonists and/or $V_{1B}$ receptor antagonist in patients having depressive symptoms and/or anxiety symptoms with the presence or absence of the at least one SNP/combination of SNPs" as used herein may refer to using such an algorithm to predict the treatment response based on the determined presence or absence of the at least one SNP and/or combination of SNPs, e.g. by integrating the at least one SNP/combination of SPCs determined in step (a) of the above method by the algorithm. In one embodiment, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 may be integrated by the algorithm. In another embodiment the absence of SNP rs28373064 in combination with the absence of SNP rs13099050, SNP rs7441352 and SNP rs12424153 may be integrated by the algorithm. In particular, the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153 may be integrated by the algorithm. As already mentioned above, other factors such as the gender of the patient and the presence or absence of the SNPs defined herein in Table 1 may also be integrated by the algorithm.

As described above, the treatment response to a $V_{1B}$ antagonist and/or a CRHR1 antagonist may be predicted by determining the presence or absence of at least one polymorphic variant in the AVPR1B gene in combination with the presence or absence of at least one polymorphic variant in the patient's genome excluding the AVPR1B gene, whereby the presence or absence of at least one polymorphic variant in the AVPR1B gene in combination with the presence or absence of at least one polymorphic variant in the patient's genome excluding the AVPR1B gene is indicative for a patient responding to the treatment of said antagonists. Hence, $V_{1B}$ receptor antagonists and/or CRHR1 antagonists may be useful in the treatment of this specific patient group.

Accordingly, another aspect of the invention relates to a $V_{1B}$ receptor antagonist and/or CRHR1 antagonist for use in the treatment of depressive symptoms and/or anxiety symptoms in a patient, the patient showing in combination the presence or absence of at least one polymorphic variant in the AVPR1B gene with the presence or absence of at least one polymorphic variant in the patient's genome excluding the AVPR1B gene.

In one embodiment the invention relates to a $V_{1B}$ receptor antagonist for use in the treatment of depressive symptoms and/or anxiety symptoms in a patient, the patient showing in combination the presence or absence of at least one polymorphic variant in the AVPR1B gene with the presence or absence of at least one polymorphic variant in the patient's genome excluding the AVPR1B gene.

In one embodiment, the polymorphic variant in the AVPR1B gene and/or in the patient's genome excluding the AVPR1B gene is a single nucleotide polymorphism (SNP). For example, the polymorphic variant in the AVPR1B gene is an SNP. In addition or alternatively, the polymorphic variant in the patient's genome excluding the AVPR1B gene may be an SNP.

In one embodiment, a polymorphic variant or biomarker in the AVPR1B gene is SNP rs28373064 which is represented by a single polymorphic change at position 27 of SEQ ID NO: 1, wherein in one or two alleles of the wild-type nucleotide A is replaced by indicator nucleotide G.

In another embodiment, the patient shows the presence or absence of SNP rs28373064 in combination with at least 1, at least 2, at least 7 or at least 10 of the other biomarkers defined in Table 1. It is understood that the patient may furthermore show the presence of any further biomarker not explicitly described herein but considered suitable by the person skilled in the art for determination of a treatment response to CRHR1 and/or $V_{1B}$ receptor antagonists. Such additional biomarkers may include additional polymorphic variants which have been obtained by a genome wide screening for polymorphic variants in a patient having depressive symptoms and/or anxiety symptoms and, optionally, by identifying at least one polymorphic variant and/or combination of polymorphic variants associated with an increased ACTH response to a combined dex/CRH test.

In one embodiment, the at least one polymorphic variant in the patient's genome excluding the AVPR1B gene is selected from the group of corresponding biomarkers as described in Table 1. In a further embodiment, the at least one polymorphic variant in the patient's genome excluding the AVPR1B gene is selected from the group of biomarkers comprising at least 2, at least 5, at least 8 or at least 11 of the corresponding biomarkers as described in Table 1. In another embodiment, the at least one polymorphic variant in the patient's genome excluding the AVPR1B gene is selected from the group of biomarkers consisting of the corresponding biomarkers described in Table 1.

In another embodiment, a polymorphic variant in the AVPR1B gene of the patient's genome is SNP rs28373064 which is represented by a single polymorphic change at position 27 of SEQ ID NO: 1, wherein in one or two alleles of the wild-type nucleotide A is replaced by indicator nucleotide G or an SNP in strong linkage disequilibrium with SNP rs28373064.

In another embodiment, the at least one polymorphic variant in the patient's genome excluding the AVPR1B gene is selected from the group of biomarkers comprising SNP rs9880583 which is represented by a single polymorphic change at position 27 of SEQ ID NO: 2: wherein in one or two alleles the wild-type nucleotide C is replaced by indicator nucleotide G. SNP rs13099050 which is represented by a single polymorphic change at position 27 of SEQ ID NO: 3: wherein in one or two alleles the wild-type nucleotide A is replaced by indicator nucleotide C, SNP rs7441352 which is represented by a single polymorphic change at position 27 of SEQ ID NO: 4; wherein in one or two alleles the wild-type nucleotide A is replaced by indicator nucleotide G; SNP rs730258 which is represented by a single polymorphic change at position 27 of SEQ ID NO: 5, wherein in one or two alleles the wild-type nucleotide C is replaced by indicator nucleotide T; SNP rs12654236 which is represented by a single polymorphic change at position 27 of SEQ ID NO: 6, wherein in one or two alleles the wild-type nucleotide A is replaced by indicator nucleotide G; SNP rs17091872 which is represented by a single polymorphic change at position 27 of SEQ ID NO: 7, wherein in one or two alleles the wild-type nucleotide A is replaced by indicator nucleotide G; SNP rs12254219 which is represented by a single polymorphic change at position 27 of SEQ ID NO: 8, wherein in one or two alleles the wild-type nucleotide C is replaced by indicator nucleotide T; SNP rs11575663 which is represented by a single polymorphic change at position 27 of SEQ ID NO: 9, wherein in one or two alleles the wild-type nucleotide A is replaced by indicator nucleotide G; SNP rs7080276 which is represented by a single polymorphic change at position 27 of SEQ ID NO: 10, wherein in one or two alleles the wild-type nucleotide A is replaced by indicator nucleotide G; SNP rs7416 which is represented by a single polymorphic change at position 27 of SEQ ID NO: 11, wherein in one or two alleles the wild-type nucleotide A is replaced by indicator nucleotide G; SNP rs12424513 which is represented by a single polymorphic change at position 27 of SEQ ID NO: 12, wherein in one or two alleles the wild-type nucleotide C is replaced by indicator nucleotide T; SNP rs1035050 which is represented by a single polymorphic change at position 27 of SEQ ID NO: 13, wherein in one or two alleles the wild-type nucleotide C is replaced by indicator nucleotide T; SNP rs9959162 which is represented by a single polymorphic change at position 27 of SEQ ID NO: 14, wherein in one or two alleles the wild-type nucleotide A is replaced by indicator nucleotide C; SNP rs8088242 which is represented by a single polymorphic change at position 27 of SEQ ID NO: 15, wherein in one or two alleles the wild-type nucleotide A is replaced by indicator nucleotide G. and/or an SNP in strong linkage disequilibrium with any of the foregoing SNPs.

In another embodiment, the patient eligible for a therapy with a CRHR1 antagonist and/or a $V_{1B}$ receptor antagonist shows a combination of the presence or absence of SNP rs28373064 in combination with at least 1, at least 2, at least 3, at least 4, at least 5, at least 6, at least 7, at least 8, at least 9, at least 10, at least 11, at least 12, at least 13 or all of the other biomarkers described in Table 1.

In another embodiment, the patient eligible for a therapy with a CRHR1 antagonist and/or a $V_{1B}$ receptor antagonist shows the presence of SNP rs28373064 in combination with the presence of SNP rs9880583, SNP rs730258, SNP rs12654236. SNP rs17091872, SNP rs12254219, SNP rs11575663, SNP rs7080276, SNP rs7416, SNP rs1035050, SNP rs9959162 and SNP rs8088242. In another embodiment, the patient eligible for a therapy with a CRHR1 antagonist and/or a $V_{1B}$ receptor antagonist shows the absence of SNP rs28373064 in combination with the absence of SNP rs13099050, SNP rs7441352 and SNP rs12424153. In yet another embodiment, the patient eligible for a therapy with a CRHR1 antagonist and/or a $V_{1B}$ is receptor antagonist shows the presence of SNP rs28373064 in combination with the presence of SNP rs9880583, SNP rs730258, SNP rs12654236, SNP rs17091872, SNP rs12254219, SNP rs11575663, SNP rs7080276, SNP rs7416, SNP rs1035050, SNP rs9959162 and SNP rs8088242 and the absence of SNP rs28373064 in combination with the absence of SNP rs13099050, SNP rs7441352 and SNP rs12424153.

In yet another embodiment, the patient showing in combination the presence or absence of at least one polymorphic variant in the AVPR1B gene with the presence or absence of at least one polymorphic variant in the patient's genome excluding the AVPR1B gene is identified by (i) determining in a patient's sample the status of a biomarker as defined above; and (ii) identifying the patient as eligible for a therapy with a $V_{1B}$ receptor antagonist and/or a CRHR1 antagonist, where optionally the algorithm provided by the method described above predicts that the patient responds to the treatment with the $V_{1B}$ receptor antagonist and/or the CRHR1 antagonist.

In yet another embodiment, the patient showing in combination the presence or absence of at least one polymorphic variant in the AVPR1B gene with the presence or absence of at least one polymorphic variant in the patient's genome excluding the AVPR1B gene is identified by (i) determining in a patient's sample the status of a biomarker as defined above; and (ii) identifying the patient as eligible for a therapy with a $V_{1B}$ receptor antagonist and/or a CRHR1 antagonist, where the algorithm provided by the method described above predicts that the patient responds to the treatment with the $V_{1B}$ receptor antagonist and/or the CRHR1 antagonist.

In another embodiment, a further clinical marker as described herein may be present in the patient.

Another aspect of the invention concerns a method for monitoring depression and/or anxiety therapy of a patient with a CRHR1 antagonist and/or a $V_{1B}$ receptor antagonist comprising the step of determining the status of a biomarker or a group of biomarkers as defined above before and during the therapy, optionally also after the therapy.

One embodiment concerns a method for monitoring depression and/or anxiety therapy of a patient with a $V_{1B}$ receptor antagonist comprising the step of determining the status of a biomarker or a group of biomarkers as defined above before and during the therapy, optionally also after the therapy.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a patient's sample the status of a biomarker or a group of biomarkers as defined above;

(b) identifying the patient as eligible for a therapy with a CRHR1 antagonist and/or a $V_{1B}$ receptor antagonist, where optionally the algorithm provided by the method described herein predicts that patient responds to the treatment with CRHR1 antagonists and/or $V_{1B}$ receptor antagonists.

One embodiment of the invention concerns a method of identifying a patient with depressive symptoms and/or anxiety symptoms as eligible for a therapy with a Vie receptor antagonist, comprising:

(a) determining in a patient's sample the status of a biomarker or a group of biomarkers as defined above;

(b) identifying the patient as eligible for a therapy with a $V_{1B}$ receptor antagonist, where optionally the algorithm provided by the method described herein predicts that patient responds to the treatment with $V_{1B}$ receptor antagonists.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a nucleic acid sample isolated from a patient's sample the status of a biomarker or a group of biomarkers as defined above;

(b) identifying the patient as eligible for a therapy with a CRHR1 antagonist and/or a $V_{1B}$ receptor antagonist, where the algorithm provided by the method described herein predicts that patient responds to the treatment with CRHR1 antagonists and/or $V_{1B}$ receptor antagonists.

In one embodiment the invention concerns a method of identifying a patient with depressive symptoms and/or anxiety symptoms as eligible for a therapy with a $V_{1B}$ receptor antagonist, comprising:

(a) determining in a nucleic acid sample isolated from a patient's sample the status of a biomarker or a group of biomarkers as defined above:

(b) identifying the patient as eligible for a therapy with a $V_{1B}$ receptor antagonist, where the algorithm provided by the method described herein predicts that patient responds to the treatment with $V_{1B}$ receptor antagonists.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a nucleic acid sample isolated from a patient's sample the status of a biomarker or a group of biomarkers as defined above;

(b) identifying the patient as eligible for a therapy with a CRHR1 antagonist and/or a $V_{1B}$ receptor antagonist, where the patient's sample is classified as showing the presence of indicator nucleotides as defined above.

Another aspect of the invention concerns a method of identifying a patient with depressive symptoms and/or anxiety symptoms as eligible for a therapy with a $V_{1B}$ receptor antagonist, comprising:

(a) determining in a nucleic acid sample isolated from a patient's sample the status of a biomarker or a group of biomarkers as defined above;

(b) identifying the patient as eligible for a therapy with a $V_{1B}$ receptor antagonist, where the patient's sample is classified as showing the presence of indicator nucleotides as defined above.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a patient's sample the status of a biomarker or a group of biomarkers as defined above:

(b) identifying the patient as eligible for a therapy with a CRHR1 antagonist and/or a $V_{1B}$ receptor antagonist, where the patient's sample is classified as showing the presence or absence of indicator nucleotides as defined above.

In one embodiment the invention concerns a method of identifying a patient with depressive symptoms and/or anxiety symptoms as eligible for a therapy with a Vie receptor antagonist, comprising:

(a) determining in a patient's sample the status of a biomarker or a group of biomarkers as defined above:

(b) identifying the patient as eligible for a therapy with a $V_{1B}$ receptor antagonist, where the patient's sample is classified as showing the presence or absence of indicator nucleotides as defined above.

In some embodiments of the above methods of identifying a patient with depressive symptoms and/or anxiety symptoms as eligible for a therapy with a CRHR1 antagonist and/or a $V_{1B}$ receptor antagonist, the method may further comprise a step of administering a CRHR1 antagonist and/or a $V_{1B}$ receptor antagonist.

In some embodiments of the above methods of identifying a patient with depressive symptoms and/or anxiety symptoms as eligible for a therapy with a CRHR1 antagonist, the CRHR1 antagonist may be selected from the group consisting of CP154,526, Antalarmin, CRA 5626, Emicerfont, DMP-696, DMP-904, DMP-695, SC-241, BMS-561388, Pexacerfont, R121919, NBI30545, PD-171729, Verucerfont, NB134041, NB135965, SN003, CRA0450, SSR125543A, CP-316,311, CP-376,395, NBI-27914, ONO-2333Ms, NBI-34101, PF-572778, GSK561579 and GSK586529.

In some embodiments of the above methods of identifying a patient with depressive symptoms and/or anxiety symptoms as eligible for a therapy with a $V_{1B}$ receptor antagonist, the $V_{1B}$ receptor antagonist may be selected from the group consisting of SSR149415, Org 52186, ABT-436 and ABT-558.

Another aspect of the invention concerns a method for detecting CRH overactivity in a patient with depressive symptoms and/or anxiety symptoms, comprising determining the status of a biomarker or a group of biomarkers as defined above in a patient's sample, wherein the presence or absence of indicator nucleotides as defined above is indicative for CRH overactivity.

Another aspect of the invention concerns a method for detecting CRH overactivity in a patient with depressive symptoms and/or anxiety symptoms, comprising determining the status of a biomarker or a group of biomarkers as defined above in a nucleic acid isolated from a patient's sample, wherein the presence of indicator nucleotides as defined above is indicative for CRH overactivity.

In some embodiments of the method for detecting CRH overactivity in a patient with depressive symptoms and/or anxiety symptoms, the status of at least 2, at least 5, at least 8, at least 11 or all of the biomarkers as defined above is determined in a nucleic acid isolated from a patient's sample.

Another aspect of the invention concerns a method for monitoring depression and/or anxiety therapy of a patient with a CRHR1 antagonist and/or $V_{1B}$ receptor antagonist comprising the step of determining the status of a biomarker or a group of biomarkers as defined above before and during the therapy, optionally also after the therapy.

Another aspect of the invention concerns a method for monitoring depression and/or anxiety therapy of a patient with a $V_{1B}$ receptor antagonist comprising the step of determining the status of a biomarker or a group of biomarkers as defined above before and during the therapy, optionally also after the therapy.

In some embodiments of the method for monitoring depression and/or anxiety therapy of a patient with a CRHR1 antagonist and/or $V_{1B}$ receptor antagonist, the status of at least 2, at least 5, at least 8, at least 11 or all of the biomarkers as defined above is determined in a nucleic acid isolated from a patient's sample.

The term "monitoring" as used herein relates to the accompaniment of a depression and/or anxiety therapy during a certain period of time, typically during 6 months, 1 year, 2 years, 3 years, 5 years, 10 years, or any other period of time. The term "accompaniment" means that states of disease as defined herein and, in particular, changes of these states of disease may be detected by comparing the status of a biomarker of the present invention in a sample in any type of a periodical time segment, e.g. every week, every 2 weeks, every month, every 2, 3, 4, 5, 6, 7, 8, 9, 10, 11 or 12 month, every 1.5 year, every 2, 3, 4, 5, 6, 7, 8, 9 or 10 years, during any period of time, e.g. during 2 weeks, 3 weeks, 1, 2, 3, 4, 5, 6, 7, 8, 9, 10, 11, 12 months, 1.5, 2, 3, 4, 5, 6, 7, 8, 9, 10, 15 or 20 years, respectively. The term "before therapy of a patient with a CRHR1 antagonist and/or a $V_{1B}$ receptor antagonist" as used herein means that a patient or patient's sample may analyzed after an initial diagnosis of depression and/or anxiety and/or before the commencement of a treatment with a CRHR1 antagonist and/or a $V_{1B}$ receptor antagonist. The corresponding period of time may be 1 hour, 12 hours, 1 day, 2 days, 3 days, 4 days, 5 days, 6 days, 1 week, 2 weeks, 3 weeks, 4 weeks, 2 months, 3 months, 4 months, 5 months, 6 months, or more or any period of time in between these values. The term "during therapy of a patient with a CRHR1 antagonist and/or a $V_{1B}$ receptor antagonist" as used refers to the determination during the entire or during a part of a therapeutic treatment. For instance, the determination may be carried out between administration steps, or at a defined interval of 1 hour, 12 hours, 1 day, 2 days, 3 days, 4 days, 5 days, 6 days, 1 week, 2 weeks, 3 weeks, 4 weeks, 2 months, 3 months, 4 months, 5 months, 6 months, or more or any period of time in between these values. In a specific embodiment, the monitoring may also be carried out after the therapy of a patient with a CRHR1 antagonist and/or a $V_{1B}$ receptor antagonist, e.g. 1 hour, 12 hours, 1 day, 2 days, 3 days, 4 days, 5 days, 6 days, 1 week, 2 weeks, 3 weeks, 4 weeks, 2 months, 3 months, 4 months, 5 months, 6 months, or more or any period of time in between these values after the termination of the therapy of a patient with a CRHR1 antagonist and/or a $V_{1B}$ receptor antagonist. Changes of the status of biomarkers as defined herein above may provide the medical professional with indications regarding CRH overactivity and may lead to a modification of administration, the inclusion of other or more or less medicaments, a combination with further medicaments or any other suitable decision to increase the health of a patient.

In some embodiments of the above methods of identifying a patient with depressive symptoms and/or anxiety symptoms as eligible for a therapy with a CRHR1 antagonist, the method may further comprise a step of administering a CRHR1 antagonist. The CRHR1 antagonist may be a class I or a class II antagonist.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a nucleic acid sample isolated from a patient's sample the status of a biomarker as defined above;

(b) identifying the patient as eligible for a therapy with a CRHR1 antagonist and/or a $V_{1B}$ receptor antagonist, where the algorithm provided by the method described herein predicts that patient responds to the treatment with CRHR1 antagonists and/or $V_{1B}$ receptor antagonists.

One embodiment of the invention concerns a method of identifying a patient with depressive symptoms and/or anxiety symptoms as eligible for a therapy with a Vie receptor antagonist, comprising:

(a) determining in a nucleic acid sample isolated from a patient's sample the status of a biomarker as defined above;

(b) identifying the patient as eligible for a therapy with a $V_{1B}$ receptor antagonist, where the algorithm provided by the method described herein predicts that patient responds to the treatment with $V_{1B}$ receptor antagonists.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a patient's sample the status of a biomarker or a group of biomarkers as defined above:

(b) identifying the patient as eligible for a therapy with a CRHR1 antagonist and/or a $V_{1B}$ receptor antagonist, where optionally the algorithm provided by the method described herein predicts that the patient responds to the treatment with CRHR11 antagonists and/or $V_{1B}$ receptor antagonists.

One embodiment of the invention concerns a method of identifying a patient with depressive symptoms and/or anxiety symptoms as eligible for a therapy with a $V_{1B}$ receptor antagonist, comprising:

(a) determining in a patient's sample the status of a biomarker or a group of biomarkers as defined above;

(b) identifying the patient as eligible for a therapy with a $V_{1B}$ receptor antagonist, where optionally the algorithm provided by the method described herein predicts that the patient responds to the treatment with $V_{1B}$ receptor antagonists.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a nucleic acid sample isolated from a patient's sample the status of a biomarker as defined above;

(b) identifying the patient as eligible for a therapy with a CRHR1 antagonist and/or a $V_{1B}$ receptor antagonist, where the patient's sample is classified as showing the presence of indicator nucleotides as defined above.

One embodiment of the invention concerns a method of identifying a patient with depressive symptoms and/or anxiety symptoms as eligible for a therapy with a Via receptor antagonist, comprising:

(a) determining in a nucleic acid sample isolated from a patient's sample the status of a biomarker as defined above;

(b) identifying the patient as eligible for a therapy with a $V_{1B}$ receptor antagonist, where the patient's sample is classified as showing the presence of indicator nucleotides as defined above.

Another aspect of the invention concerns a method of identifying a patient with depressive symptoms and/or anxiety symptoms as eligible for a therapy with a CRHR1 antagonist and/or a $V_{1B}$ receptor antagonist, comprising:

(a) determining in a patient's sample the status of a biomarker or a group of biomarkers as defined above;

(b) identifying the patient as eligible for a therapy with a CRHR1 antagonist and/or a $V_{1B}$ receptor antagonist, where the patient's sample is classified as showing the presence or absence of indicator nucleotides as defined above.

One embodiment of the invention concerns a method of identifying a patient with depressive symptoms and/or anxiety symptoms as eligible for a therapy with a $V_{1B}$ receptor antagonist, comprising:

(a) determining in a patient's sample the status of a biomarker or a group of biomarkers as defined above;

(b) identifying the patient as eligible for a therapy with a $V_{1B}$ receptor antagonist, where the patient's sample is classified as showing the presence or absence of indicator nucleotides as defined above.

In some embodiments of the methods of identifying a patient with depressive symptoms and/or anxiety symptoms as eligible for a therapy with a CRHR1 antagonist and/or a $V_{1B}$ receptor antagonist, the status of at least 2, at least 5, at least 8, at least 11 or all of the biomarkers as defined above, e.g. in Table 1, is determined in a nucleic acid isolated from a patient's sample.

In some embodiments of the above methods of identifying a patient with depressive symptoms and/or anxiety symptoms as eligible for a therapy with a CRHR1 antagonist, the method may further comprise a step of administering a CRHR1 antagonist. The CRHR1 antagonist may be a class I or a class II antagonist.

Another aspect of the invention relates to $V_{1B}$ receptor antagonist and/or a CRHR1 antagonist for use in the treatment of depressive symptoms and/or anxiety symptoms in a patient predicted to respond to the treatment with the $V_{1B}$ receptor antagonist and/or the CRHR1 antagonist by an algorithm provided by the method described above.

One embodiment of the invention relates to $V_{1B}$ receptor antagonist for use in the treatment of depressive symptoms and/or anxiety symptoms in a patient predicted to respond to the treatment with the $V_{1B}$ receptor antagonist by an algorithm provided by the method described above.

Another aspect of the invention relates to a $V_{1B}$ receptor antagonist and/or a CRHR1 antagonist for use in the treatment of depressive symptoms and/or anxiety symptoms, wherein the treatment comprises a step of determining whether or not the patient is eligible for a therapy with a $V_{1B}$ receptor antagonist and/or a CRHR1 antagonist and wherein optionally the patient is determined to be eligible for a therapy with a Vie receptor antagonist and/or a CRHR1 antagonist by the methods described herein. For example, the patient can be predicted to respond to the treatment with the Via receptor antagonist and/or the CRHR1 antagonist by an algorithm provided by the method described above.

One embodiment of the invention relates to a $V_{1B}$ receptor antagonist for use in the treatment of depressive symptoms and/or anxiety symptoms, wherein the treatment comprises a step of determining whether or not the patient is eligible for a therapy with a $V_{1B}$ receptor antagonist and wherein optionally the patient is determined to be eligible for a therapy with a $V_{1B}$ receptor antagonist by the methods described herein. For example, the patient can be predicted to respond to the treatment with the $V_{1B}$ receptor antagonist by an algorithm provided by the method described above.

In one embodiment, the invention relates to a $V_{1B}$ receptor antagonist and/or a CRHR1 antagonist for use in the treatment of depressive symptoms and/or anxiety symptoms, wherein the treatment comprises a step of identifying a patient with depressive symptoms and/or anxiety symptoms as eligible for a therapy with a CRHR1 antagonist and/or a $V_{1B}$ receptor antagonist, wherein in a patient's sample the status of a biomarker or a group of biomarkers as defined above is determined and the patient is identified as eligible for a therapy with a CRHR1 antagonist and/or a $V_{1B}$ receptor antagonist, where the algorithm provided by the method described herein predicts that the patient responds to the treatment with CRHR1 antagonists and/or $V_{1B}$ receptor antagonists.

In another aspect, the invention relates to a method of treating depressive symptoms and/or anxiety symptoms in a patient, comprising (a) identifying a patient with depressive symptoms and/or anxiety symptoms as eligible for a therapy with a CRHR1 antagonist and/or a $V_{1B}$ receptor antagonist, wherein in a patient's sample the status of a biomarker or a group of biomarkers as defined above is determined, and the patient is identified as eligible for a therapy with a CRHR1 antagonist and/or a $V_{1B}$ receptor antagonist, where the algorithm provided by the method described herein predicts that the patient responds to the treatment with CRHR1 antagonists and/or $V_{1B}$ receptor antagonists; and (b) administering a $V_{1B}$ receptor antagonist and/or a CRHR1 antagonist to the patient if the patient is predicted to respond to the treatment with CRHR1 antagonists and/or $V_{1B}$ receptor antagonists.

In one embodiment, the invention relates to a method of treating depressive symptoms and/or anxiety symptoms in a patient, comprising (a) identifying a patient with depressive symptoms and/or anxiety symptoms as eligible for a therapy with a $V_{1B}$ receptor antagonist, wherein in a patient's sample the status of a biomarker or a group of biomarkers as defined above is determined, and the patient is identified as eligible for a therapy with a $V_{1B}$ receptor antagonist, where the algorithm provided by the method described herein predicts that the patient responds to the treatment with $V_{1B}$ receptor antagonists; and (b) administering a $V_{1B}$ receptor antagonist to the patient if the patient is predicted to respond to the treatment with $V_{1B}$ receptor antagonists.

The sample, in which the presence or absence of polymorphic variants as described herein may be determined in the methods of the invention, may be selected from a tissue sample and a bodily fluid sample, and is e.g. a blood sample, plasma sample or serum sample. The sample may comprise nucleic acids, proteins, hormones, or a combination thereof from the patient. A sample comprising nucleic acids is also referred to as a nucleic acid sample. The sample may be used directly as obtained from the patient or following pretreatment. Pretreatment may include extraction (e.g. nucleic acid extraction), concentration, inactivation of interfering components, the addition of reagents, or a combination thereof.

Vasopressin receptor 1B ($V_{1B}$ receptor) antagonist as used herein refers to any compound capable of binding directly or indirectly to a $V_{1B}$ receptor so as to modulate the receptor mediated activity. Vasopressin receptor 1B (Vie receptor) antagonists as used herein include $V_{1B}$ receptor antagonists which were tested in clinical trials as well as $V_{1B}$ receptor antagonists which are currently tested in clinical trials or already admitted to the market. Various $V_{1B}$ receptor antagonists have been described in the literature and tested in clinical trials. Exemplary $V_{1B}$ receptor antagonists that have been tested in clinical trials comprise SSR149415 (also denoted as Nelivaptan; Sanofi-Aventis), Org 52186 (Organon), ABT-436 (Abbott) and ABT-558 (Abbott). It is understood, that if $V_{1B}$ receptor antagonists are described as being useful for the treatment of anxiety and/or depressive symptoms herein, the treatment response to said $V_{1B}$ receptor antagonist and/or combinations thereof may also be predicted by the methods described herein.

One embodiment of the present invention relates to a $V_{1B}$ receptor antagonist for use in the treatment of depressive symptoms and/or anxiety symptoms in a patient as defined herein and/or for whom a positive treatment response has been predicted as described herein, wherein the $V_{1B}$ receptor antagonist is selected from the group consisting of SSR149415, Org 52186, ABT-436 and/or ABT 558. In some embodiments, a combination of $V_{1B}$ antagonists, e.g. a combination of any of the aforementioned $V_{1B}$ receptor antagonists may be used for treatment of depressive and/or anxiety symptoms in a patient as defined herein. In other embodiments, a compound selected from the group consisting of SRR149415, Org 52186. ABT-436 and/or ABT 558 may be used in combination with a further $V_{1B}$ receptor antagonist as defined herein for the treatment of depressive symptoms and/or anxiety symptoms in a patient as defined herein and/or for whom a positive treatment has been predicted as described herein. In a specific embodiment the present invention relates to a $V_{1B}$ receptor antagonist for use in the treatment of depressive symptoms and/or anxiety symptoms in a patient as defined herein and/or for whom a positive treatment response has been predicted as described herein, wherein the $V_{1B}$ receptor antagonist is SSR149415. The $V_{1B}$ receptor antagonist SSR149415 (also denoted as Nelivaptan) developed by Sanofi-Aventis is a non-peptide $V_{1B}$ receptor antagonist which is orally active (Serradeil-Le Gal et al. (2002); Characterization of (2S, 4R)-1-(5-chloro-1-[(2, 4-dimethoxyphenyl)sulfonyl]-3-(2-methoxy-phenyl)-2-oxo-2, 3-dihydro-1H-indol-3-yl)-4-hydroxy-N,N-dimethyl-2-pyrrolidine carboxamide (SSR149415), a Selective and Orally Active Vasopressine $V_{1b}$ Receptor Antagonist; JPET 300:1122-1130). SSR149415 is a (2S, 4R)-1-(5-chloro-1-[(2,4-dimethoxy phenyl)sulfonyl]-3-(2-methoxy-phenyl)-2-oxo-2,3-dihydro-1H-indol-3-yl)-4-hydroxy-N,N-dimethyl-2-pyrrolidinecarboxamide having the structural formula

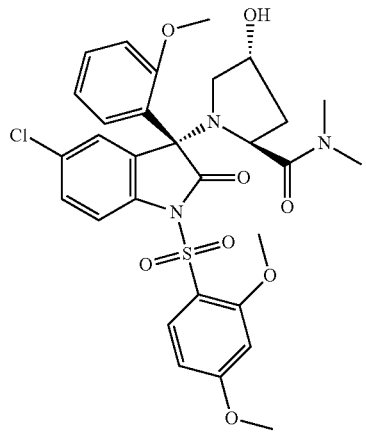 [SMILES: COc1ccc(S(=O)(=O)N2C(=O)[C@@](c3ccccc3OC)(N3C[C@H](O)C[C@H]3C(=O)N(C)C)c3cc(Cl)ccc32)c(OC)c1]

In another specific embodiment the present invention relates to a $V_{1B}$ receptor antagonist for use in the treatment of depressive symptoms and/or anxiety symptoms in a patient as defined herein and/or for whom a positive treatment response has been predicted as described herein, wherein the $V_{1B}$ antagonist is Org 52186. In a further specific embodiment the present invention relates to a $V_{1B}$ receptor antagonist for use in the treatment of depressive symptoms and/or anxiety symptoms in a patient as defined herein and/or for whom a positive treatment response has been predicted as described herein, wherein the $V_{1B}$ receptor antagonist is ABT-436. In another specific embodiment the present invention relates to a $V_{1B}$ receptor antagonist for use in the treatment of depressive symptoms and/or anxiety symptoms in a patient as defined herein and/or for whom a positive treatment response has been predicted as described herein, wherein the $V_{1B}$ receptor antagonist is ABT-558.

The term "CRHR1 antagonist" refers to a compound capable of binding directly or indirectly to a CRH receptor 1 so as to modulate the receptor mediated activity. It is understood, that if CRHR1 antagonists are described as being useful for the treatment of anxiety and/or depressive symptoms herein, the treatment response to said CRHR1 antagonist and/or combinations thereof may also be predicted by the methods described herein.

CRHR1 antagonists are well known in the literature and are e.g. described in WO 94/13676, EP 0 773 023. WO 2004/047866, WO 2004/094420, WO 98/03510, WO 97/029109, WO 2006/044958, WO 2001/005776 and WO 95/033750. Exemplary CRHR1 antagonists comprise NB130775/R121919 (Neurocrine), CP316.311 (Pfizer), CP154,526 (Pfizer), Emicerfont (Glaxo), ONO-2333Ms (Ono Pharmaceutical), Pexacerfont (Bristol-Myers-Squibb), SSR125543 (Sanofi-Aventis), NBI-34101 (Neurocrine) and TAI041 (Taisho). Further exemplary CRHR1 antagonists comprise Antalarmin, CRA 5626, DMP-696. DMP-904, DMP-695, SC-241, BMS-561388, NBI30545, PD-171729, Verucerfont, NB134041, NBI35965. SN003, CRA0450, CP-376,395, NBI-27914, PF-572778, GSK561579 and GSK586529.

In particular, the term "CRHR 1 antagonist" relates to class I or class II antagonists. Class I CRHR1 antagonists as used herein may be characterized in that the heterocyclic hydrogen bond acceptor and the bottom group are connected by a two-atom linker as exemplified by CRHR1 antagonists R-121919, NBI-30545, CP-154526, DMP696, pexacerfont (BMS-562086), emicerfont (GW876008), or verucerfont (GSK561679). Class II CRF1R antagonists as used herein may be characterized by a two-atom linker between hydrogen bond acceptor and the bottom group as present in CRHR1 antagonist SSR125543A.

In some embodiments, the CRHR1 antagonist may be selected from the group consisting of CP154,526. Antalarmin, CRA 5626, Emicerfont, DMP-696, DMP-904, DMP-695, SC-241, BMS-561388, Pexacerfont, R121919, NB130545, PD-171729, Verucerfont, NB134041, NBI35965, SN003, CRA0450, SSR125543A, CP-316,311, CP-376,395, NBI-27914, ONO-2333Ms, NBI-34101, PF-572778, GSK561579 and GSK586529.

The corresponding structural formulas of some of the above-mentioned CRHR1 antagonists for use in the present invention or for which a treatment response is to be predicted are set out in Table 3 below:

TABLE 3

| Structural formula | CRHR1 antagonist (name) |
|---|---|
| 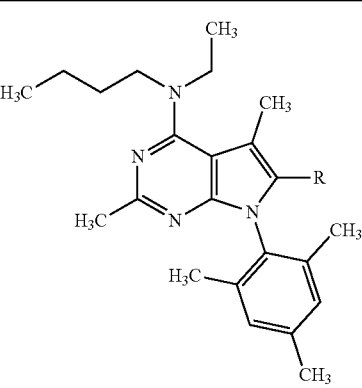 | R = H CP154,526<br>R = CH₃<br>Antalarmin |
| 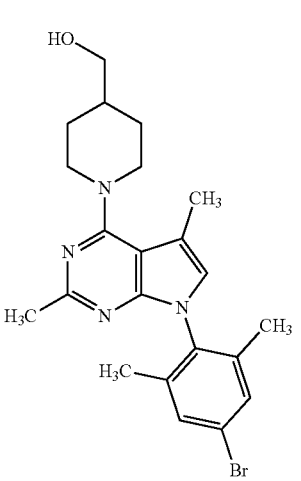 | CRA5626/<br>R317573/<br>JNJ19567470/<br>TAI-041 |
| 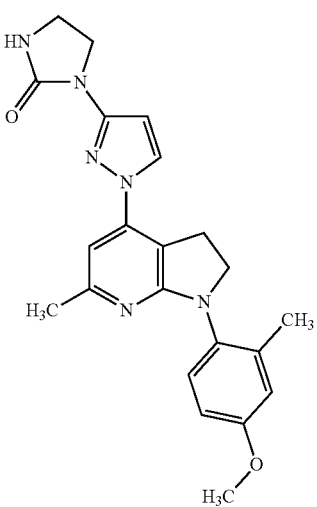 [SMILES: COc1ccc(N2CCc3c(-n4ccc(N5CCNC5=O)n4)cc(C)nc32)c(C)c1] | GW876008/<br>Emicerfont |

TABLE 3-continued
| Structural formula | CRHR1 antagonist (name) |
|---|---|
| 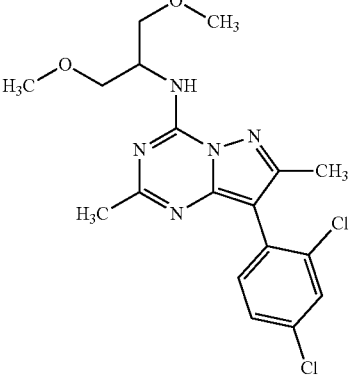 | DMP-696 |
| 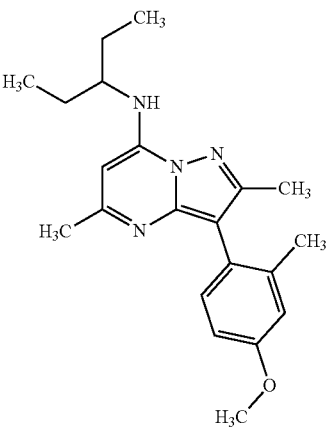 [SMILES: CCC(CC)Nc1cc(C)nc2c(-c3ccc(OC)cc3C)c(C)nn12] | DMP-904 |
| 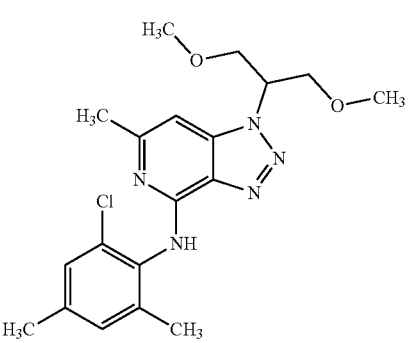 | DMP-695 |
| 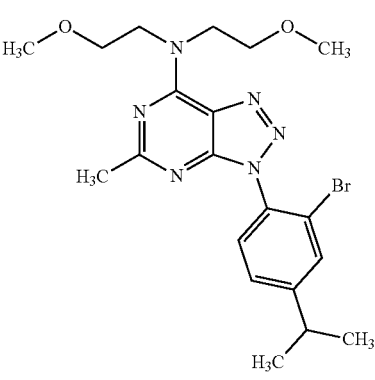 [SMILES: COCCN(CCOC)c1nc(C)nc2c1nnn2-c1ccc(C(C)C)cc1Br] | SC-241/LWH-234 |
| 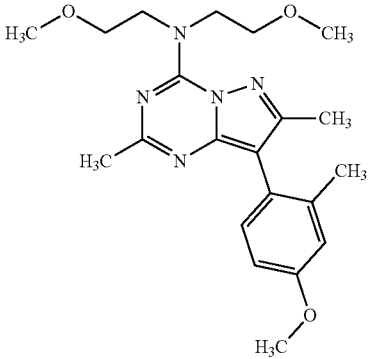 | BMS-561388 |
| 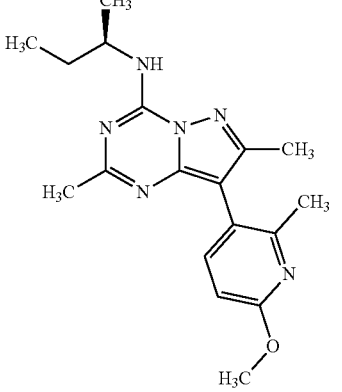 | BMS-562086/ Pexacerfont |
| 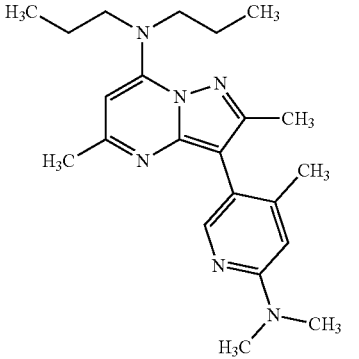 [SMILES: CCCN(CCC)c1cc(C)nc2c(-c3cnc(N(C)C)cc3C)c(C)nn12] | R121919/ NBI30775 |
| 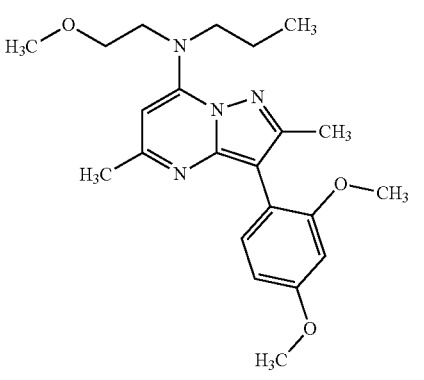 | NBI30545 |

TABLE 3-continued
| Structural formula | CRHR1 antagonist (name) |
|---|---|
| 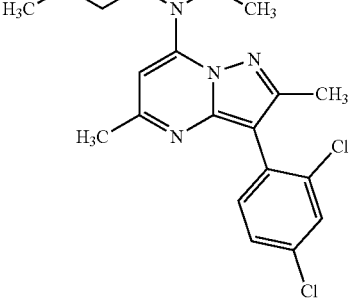 | PD-171729 |
| 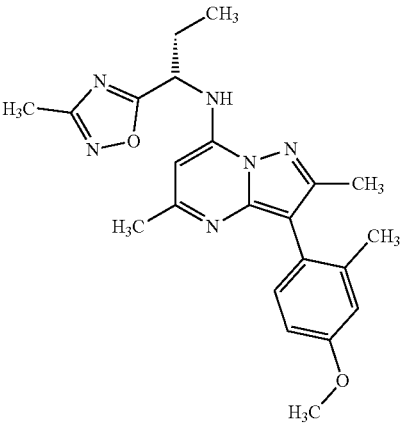 | GSK561679/ NBI-77860/ Verucerfont |
| 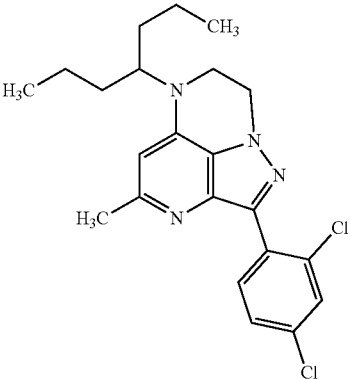 [SMILES: CCCC(CCC)N1CCn2nc(-c3ccc(Cl)cc3Cl)c3nc(C)cc1c32] | SB-723620/ NBI34041 |
| 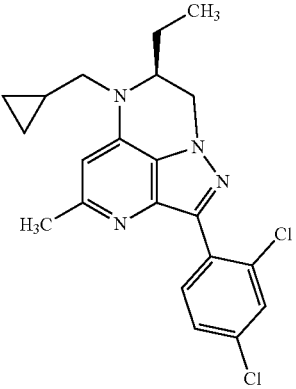 [SMILES: CC[C@H]1Cn2nc(-c3ccc(Cl)cc3Cl)c3nc(C)cc(c32)N1CC1CC1] | NBI35965 |
| 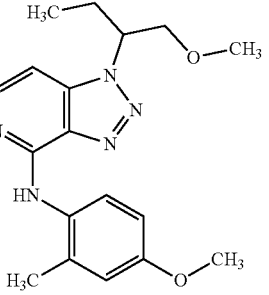 | SN003 |
| 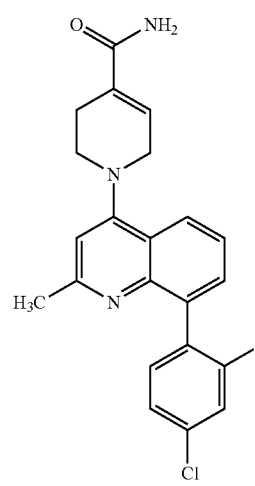 | CRA0450/ R278995 |
| 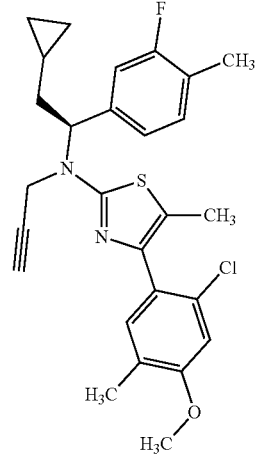 [SMILES: C#CCN(c1nc(-c2cc(C)c(OC)cc2Cl)c(C)s1)[C@@H](CC1CC1)c1ccc(C)c(F)c1] | SSR125543A |

TABLE 3-continued

| Structural formula | CRHR1 antagonist (name) |
|---|---|
| [structure with pyridine core, X linker, methyl groups] | X = O CP-316,311<br>X = NH CP-376,395 |
| [pyrimidine structure with cyclopropylmethyl and trichlorophenyl groups] | NBI-27914 |

ONO-2333Ms, NBI 34101, PF-572778, GSK561579 and GSK586529 are described by Zorilla and Koob (Drug Discovery Today, 2010, 371-383) as corticotropin releasing factor receptor antagonists (corticotropin releasing factor is a synonym for CRHR1 antagonists) tested in clinical trials.

The methods described above are not restricted to methods related to a treatment response to CRHR1 antagonists and/or $V_{1B}$ antagonists in patients with depressive symptoms and/or anxiety symptoms. The treatment response to any other compound, drug or biomolecule that is capable for treating depressive symptoms and/or anxiety symptoms in patients who have CRH overactivity may be also be predicted by methods described herein. In particular, the disclosure can be understood to mean that the term "CRHR1 antagonists" or "$V_{1B}$ antagonists" can be replaced by any other compound that interferes with the CRHR1 pathway and/or leads to a remission of depressive symptoms and/or anxiety symptoms patients with CRH overactivity.

As described herein, it has been found that a specific group of biomarkers may be used for predicting the treatment response to a CRHR1 antagonist and/or a $V_{1B}$ receptor antagonist in a patient suffering from depressive symptoms and/or anxiety symptoms. In another aspect the present invention thus relates to a group of biomarkers, comprising:

SNP rs28373064 which is represented by a single polymorphic change at position 27 of SEQ ID NO: 1, wherein in one or two alleles of the wild-type nucleotide A is replaced by indicator nucleotide G, SNP rs9880583 which is represented by a single polymorphic change at position 27 of SEQ ID NO: 2, wherein in one or two alleles the wild-type nucleotide C is replaced by indicator nucleotide G.

SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

It is understood that the group of biomarkers may, in addition to the above mentioned biomarkers, comprise any further biomarker considered suitable by the person skilled in the art for predicting a treatment response to a CRHR1 antagonist and/or a $V_{1B}$ receptor antagonist, in particular biomarkers identified by a genome wide screening for polymorphic variants in a patient having depressive symptoms and/or anxiety symptoms and, optionally, by identifying at least one polymorphic variant and/or combination of polymorphic variants associated with increased ACTH response to a combined dexamethasone supression/CRH stimulation test in the patient. In one embodiment the group of biomarkers consists only of the biomarkers described herein in Table 1.

In a further aspect, the present invention also relates to a kit, diagnostic composition or device for the analysis of at least two SNPs indicative for a treatment response to a V$_{1B}$ receptor antagonist and/or a CRHR1 antagonist in a patient with depressive and/or anxiety symptoms, comprising a probe selective for at least one polymorphic variant in the AVPR1B gene and at least one probe selective for a polymorphic variant in the patient's genome excluding the AVPR1B gene.

In one embodiment, the present invention also relates to a kit, diagnostic composition or device for the analysis of at least two SNPs indicative for a treatment response to a V$_{1B}$ receptor antagonist in a patient with depressive and/or anxiety symptoms, comprising a probe selective for at least one polymorphic variant in the AVPR1B gene and at least one probe selective for a polymorphic variant in the patient's genome excluding the AVPR1B gene.

In particular, the genetic variant in the AVPR1B gene to be analyzed is SNP rs28373064. In one embodiment the at least one polymorphic variant in the patient's genome excluding the AVPR1B gene is selected from the group of corresponding biomarkers defined in Table 1.

Hence, in one embodiment, the kit, diagnostic composition or device is for analysis of the group of biomarkers comprising SNP rs28373064 which is represented by a single polymorphic change at position 27 of SEQ ID NO: 1, wherein in one or two alleles of the wild-type nucleotide A is replaced by indicator nucleotide G, SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

In one embodiment, the kit, diagnostic composition or device comprises at least 2, at least 5, at least 8 or at least 11 probes selective for the biomarkers as defined in Table 1. In one embodiment, the kit, diagnostic composition or device comprises a probe selective for SNP rs28373064 and at least 1, at least 2, at least 3, at least 4, at least 5, at least 6, at least 7, at least 8, at least 10, at least 11, at least 12, at least 13 or at least 14 probes selective for a polymorphic variant in the patient's genome excluding the AVPR1B gene as described herein in Table 1. In another embodiment, the kit, diagnostic composition or device is for analysis of a group of biomarkers consisting of the biomarkers as described in Table 1, i.e. it comprises a set of probes selective for the biomarkers defined in Table 1 only. It is however understood that while in this case the kit, diagnostic composition or device only includes probes selective for the biomarkers of Table 1 and no probes selective for other biomarkers, it may nevertheless include further substances, ingredients or components suitable for the performance of the analysis.

In another embodiment, the kit, diagnostic composition or device may also be for analysis of the group of biomarkers described in Table 1 and any further marker considered suitable by the person skilled in the art for indicating a treatment response to a CRHR1 antagonist and/or a V$_{1B}$ antagonist. Such further biomarkers may be identified by the genotyping analysis as described herein.

The term "probe selective for the biomarkers" as used herein refers to a piece of DNA, which is capable of specifically binding to a polymorphic site according to the present invention. The probe may, for example, be designed such that, e.g. under stringent conditions it only binds to a sequence comprising the indicator nucleotide, or the wild-type sequence, or a complementary strand thereof. In other embodiments, the probe may be capable of binding to a polymorphic site according to the present invention, i.e. be able to bind to the wild-type sequence, the indicator nucleotide comprising sequence or any other variant at that position as defined herein above. The specificity of the probe may further be adjusted, for example in hybridization experiments, by the changing the concentration of salts, modifying the temperature of the reaction, adding further suitable compounds to the reaction etc.

The probe may also be designed such that it binds outside of the polymorphic site. e.g. within the sequence of SEQ ID NO: 1 to 15.

The probe according to the present invention may, in further embodiments, comprise, or consist of a nucleic acid molecule being at least 90%, 91%, 92%, 93%, 94%, 95%, 96%, 97%, 98% or 99% or 99.5% or 99.6%, 99.7%, 99.8%, or 99.9% identical to the sequence of SEQ ID NO: 1 to 15, or to fragments thereof, which comprise the polymorphic site as defined herein above, wherein said sequence of SEQ ID NO: 1 to 15 comprises the respective indicator nucleotide as described herein above, or to any fragments of said sequences, or to the corresponding wild-type sequences as defined herein above, or to the complementary sequences of these sequences.

A probe according to the present invention may have any suitable length, e.g. a length of 15, 20, 30, 40, 50, 100, 150, 200, 300, 500, 1000 or more than 1000 nucleotides. The probe may further be suitable modified, e.g. by the addition of labels, e.g. fluorescent labels, dyes, radioactive labels etc. In further embodiments, the probe may also be functionally adjusted to a detection method.

In further embodiments, the kit, diagnostic composition or device as defined herein above may comprise accessory ingredients such as PCR buffers, ions like bivalent cations or monovalent cations, hybridization solutions etc. The kit, diagnostic composition or device may comprise an enzyme for primer elongation, nucleotides and/or labeling agents. An enzyme for primer elongation may, for example, be a polymerase such as Taq polymerase. Pfu polymerase etc. Nucleotides may preferably be dNTPs, or derivatives thereof. A labeling agent may be, for example, an agent leading to the labeling with a radioactive label, an enzymatic label, a fluorescent label, a chemiluminescent or a bioluminescent label. The term "enzymatic label" relates to labels, which comprise enzymatic activities. A typical, preferred example is the horseradish peroxidase enzyme (HRP). This enzyme complex subsequently may catalyze the conversion of a suitable substrate, e.g. a chemiluminescent substrate into a sensitized reagent which ultimatly lead to the emission of light or production of a color reaction. The term "radioactive label" relates to labels emitting radioactive radiation, preferably composed of radioactive isotopes. The term "radioactive isotope" in the context of the label relates to any such factor known to the person skilled in the art. More preferably, the term relates to $^3$H, $^{14}$C, $^{32}$P. $^{33}$P, $^{35}$S or $^{125}$I. The term "chemiluminescent label" relates to a label, which is capable of emitting light (luminescence) with a limited emission of heat as the result of a chemical reaction. For example, the term relates to luminol, cyalume, oxalyl chloride, TMAE (tetrakis (dimethylamino) ethylene), pyragallol, lucigenin, acridinumester or dioxetane. The term "bioluminescent label" relates to a label, which is capable of emitting light due to a biochemical reaction. Typically, the term refers to the production of light due to the reaction of a luciferin and a luciferase. In such a reaction scheme, the luciferase catalyzes the oxidation of luciferin resulting in light and an inactive oxyluciferin. The term "fluorescent label" relates to chemically reactive derivatives of a fluorophores. Typically common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide. Reaction of any of these reactive dyes with another molecule results in a stable covalent bond formed between a fluorophore and a labelled molecule.

Following a fluorescent labeling reaction, it is often necessary to remove any nonreacted fluorophore from the labeled target molecule.

In further embodiments the kit, diagnostic composition or device may also comprise accessory ingredients like secondary affinity ligands, e.g. secondary antibodies, detection dyes, or other suitable compound or liquids necessary for the performance of a nucleic acid detection. Such ingredients as well as further details would be known to the person skilled in the art and may vary depending on the detection method carried out. Additionally, the kit or device may comprise an instruction leaflet and/or may provide information as to the relevance of the obtained results.

Another aspect of the invention relates to a microarray for the analysis of at least two SNPs indicative for a treatment response to a $V_{1B}$ receptor antagonist and/or a CRHR1 antagonist in a patient with depressive and/or anxiety symptoms, comprising a probe selective for a polymorphic variant in the AVPR1B gene, optionally SNP rs28373064 and at least one probe selective for a polymorphic variant in the patient's genome excluding the AVPR1B gene.

One embodiment of the invention relates to a microarray for the analysis of at least two SNPs indicative for a treatment response to a $V_{1B}$ receptor antagonist in a patient with depressive and/or anxiety symptoms, comprising a probe selective for a polymorphic variant in the AVPR1B gene, optionally SNP rs28373064 and at least one probe selective for a polymorphic variant in the patient's genome excluding the AVPR1B gene.

In one embodiment, the probe selective for the at least one a polymorphic variant in the patient's genome excluding the AVPR1B gene is selected from a group of probes comprising probes selective for the biomarkers:

SNP rs9880583 which is represented by a single polymorphic change at position 27 of SEQ ID NO: 2, wherein in one or two alleles the wild-type nucleotide C is replaced by indicator nucleotide G, SNP rs13099050 which is represented by a single polymorphic change at position 27 of SEQ ID NO: 3, wherein in one or two alleles the wild-type nucleotide A is replaced by indicator nucleotide C, SNP rs7441352 which is represented by a single polymorphic change at position 27 of SEQ ID NO: 4, wherein in one or two alleles the wild-type nucleotide A is replaced by indicator nucleotide G, SNP rs730258 which is represented by a single polymorphic change at position 27 of SEQ ID NO: 5, wherein in one or two alleles the wild-type nucleotide C is replaced by indicator nucleotide T, SNP rs12654236 which is represented by a single polymorphic change at position 27 of SEQ ID NO: 6, wherein in one or two alleles the wild-type nucleotide A is replaced by indicator nucleotide G, SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and/or SNP rs8088242 which is represented by a single polymorphic change at position 27 of SEQ ID NO: 15, wherein in one or two alleles the wild-type nucleotide A is replaced by indicator nucleotide G.

The microarray may comprise at least 2, at least 5, at least 8 or at least 11 probes selective for the biomarkers as defined in Table 1. In one embodiment, the biomarker may comprise a probe selective for SNP rs28373064 and at least 1, at least 2, at least 3, at least 4, at least 5, at least 6, at least 7, at least 8, at least 9, at least 10, at least 11, at least 12, at least 13 or at least 14 probes selective for the biomarkers defined in Table 1 (excluding SNP rs28373064). In another embodiment, the microarray consists of probes selective for the biomarkers as described in Table 1 only, i.e. it only includes probes selective for the biomarkers of Table 1 and no probes selective for other biomarkers.

In another embodiment, the microarray may comprise probes selective for the biomarkers of Table 1 and any further marker considered suitable by the person skilled in the art for indicating a treatment response to a CRHR1 antagonist and/or a $V_{1B}$ receptor antagonist. Such further biomarkers may be identified by the genotyping analysis as described herein.

It is understood that the term "probes selective for" relates to probes which are present on/in the microarray, kit, diagnostic composition or device and are selective for an indicator nucleotide or the corresponding wild-type nucleotide as defined herein above.

In a standard setup a microarray comprises immobilized probes to detect a nucleic acid comprising a polymorphic site as defined herein above. The probes on/in the microarray, kit, diagnostic composition or device may, for example, be complementary to one or more parts of the sequence of SEQ ID NO: 1 to 15 and/or to corresponding wild-type sequences. Typically, cDNAs, PCR products, and oligonucleotides may be used as probes. Furthermore, any type of fragment or sub-portion of any of the markers sequences may be combined with any further fragment or sub-portion of any of said sequences SEQ ID NO: 1 to 15, or corresponding wild-type sequences.

There is virtually no limitation on the number of probes which are spotted on a DNA array. Also, a marker can be represented by two or more probes, the probes hybridizing to different parts of a gene. Probes are designed for each selected marker gene. Such a probe is typically an oligonucleotide comprising 5-50 nucleotide residues. Longer DNAs can be synthesized by PCR or chemically. Methods for synthesizing such oligonucleotides and applying them on a substrate are well known in the field of micro-arrays.

The invention is further described in the following example which is solely for the purpose of illustrating specific embodiments of the invention, and is also not to be construed as limiting the scope of the invention in any way.

Example 1

Genetic polymorphisms that influence the extent of the ACTH response in the combined Dex/CRH test in patients with current moderate to severe depression were identified using genome-wide SNP analysis of epistasis with genetic variation in the AVPR1B gene, a key player in the pathways relating to the combined dex/CRH test.

These polymorphisms describe genetic variations that in interaction with genetic variation in the AVPR1B gene lead to major depression with CRH hyperdrive.

Patients carrying the alleles/genotypes associated with a larger cortisol or ACTH response in the dex/CRH test should therefore profit from CRHR1 antagonist and/or $V_{1B}$ receptor antagonist treatment of depression and anxiety.

Patients:

Patients with unipolar or bipolar depression admitted as inpatients to the Max Planck Institute of Psychiatry (MPI), Munich, Germany, for treatment of a depressive episode were included in the study. Patients were diagnosed by psychiatrists according to the Diagnostic and Statistical Manual of Mental Disorders (DSM) IV criteria. Patients with bipolar disorder or depressive disorder due to a general medical or neurological condition were excluded, as were patients with a lifetime diagnosis of drug abuse and depressive symptoms secondary to alcohol or substance abuse or dependency. Ethnicity was recorded using a self-report sheet for nationality, first language and ethnicity of the patient and of all four grandparents.

All patients were Caucasian and part of the Munich-Antidepressant-Response-Signature (MARS) project (Hennings et al. Clinical characteristics and treatment outcome in a representative sample of depressed inpatients—findings from the Munich Antidepressant Response Signature (MARS) project. *J Psychiatr Res*. January 2009; 43(3):215-229: www.mars-depression.de). They were treated with antidepressant medications according to doctor's choice. Severity of depressive symptoms was assessed at admission and at the time of the dex-CRH test by trained raters using the 17-item Hamilton Depression Rating Scale (HAM-D) (Hamilton M. A rating scale for depression. *J Neurol Neurosurg Psychiatry* 1960; 23:56-62). 352 patients fulfilling the criteria for at least a moderate to severe depressive episode (HAM-D≥18) at both time points and who had been administered a dex-CRH test within 10 days of in-patients admission and had genome-wide SNP data were included in this analysis. The study was approved by the Ethics Committee of the Ludwig Maximilians University in Munich. Germany, and written informed consent was obtained from all subjects.

Dex-CRH Test:

The dex-CRH test was administered as described in detail in Heuser et al. Shortly, subjects were pre-treated with 1.5 mg of dexamethasone per os at 1 pm. The following day, at 3 pm, 3.30 pm, 3.45 pm, 4 pm and 4.15 pm blood was drawn. An intravenous bolus of 100 μg of human CRH (Ferring, Kiel, Germany) was given at 3.02 pm. Plasma ACTH concentrations were assessed by an immunometric assay without extraction (Nichols Institute, San Juan Capistrano, Calif.; USA). The neuroendocrine response to the dex/CRH test was analyzed using the total area under the curve (AUC) of the ACTH response.

SNP Genotyping:

After enrollment in the study 40 ml of EDTA blood was drawn from each patient. DNA was extracted from fresh blood using the Puregene® whole blood DNA-extraction kit (Gentra Systems Inc; MN).

Genotyping was performed on Illumina Human 610k quad genotyping arrays (Illumina Inc., San Diego, USA) according to the manufacturer's standard protocols. The average call rate exceeded 99%, with samples below 98% being either retyped or excluded from the study. The reproducibility for samples genotyped twice was 99.99%6 or better.

Data Analysis:

To identify genetic predictors for the ACTH response to the dex/CRH test in patients with moderate to severe depression, the full sample of 352 patients was used. After natural log transformation of the AUC of the ACTH response in the dex-CRH test, an analysis of epistasis (gene by gene interaction with the AVPR1B SNP rs28373064) was used to determine SNPs associated with the quantitative phenotype natural log of the AUC of the ACTH response. This analysis was done genome wide and only SNPs with a P-value of $<1*10^{-5}$ were retained for the building of the genetic predictor. This resulted in a total of 14 SNPs. For the prediction analysis patients were dichotomized into high vs. low responders by selecting the top and the bottom quartile of the phenotype. This lead to a number of 88 patients in each group. For the low responder group the natural log of the AUC of the ACTH ranged from 5.704 to 6.384, for the high responder group the range of the natural log of the AUC of the ACTH ranged from 7.399 to 8.980. See the corresponding histogram in FIG. 1 for the trait distribution in the two groups The 14 SNPs retained were then used to predict either ACTH response status support vector machine" approach (implementation DTREG 10.6.21 www.dtreg.com). All values were derived from leave-one-out cross-validation.

Results:

The top 14 associations with ACTH response in interaction with AVPR1B genetic variation status are given in Table 4. The genotypes for the 14 SNPs each were then used to predict high vs. low ACTH response status using interaction with AVPR1B genetic variation applying leave-one-out cross-validation.

The Results of the Prediction are Summarized Below:

For the prediction of the dichotomized high vs low ACTH response status in the dex-CRH test the following prediction values in the leave-one-out cross validation were achieved:

ACTH:
Accuracy=75.00%
True positive (TP)=69 (39.2%)
True negative (TN)=63 (35.8%)
False positive (FP)=25 (14.2%)
False negative (FN)=19 (10.8%)
Sensitivity=78.41%
Specificity=71.59%
Geometric mean of sensitivity and specificity=74.92%
Positive Predictive Value (PPV)=73.40%
Negative Predictive Value (NPV)=76.83%
Geometric mean of PPV and NPV=75.10%
Precision=73.40%
Recall=78.41%
F-Measure=0.7582
Area under ROC curve (AUC)=0.780475

Summary and Discussion

Using genome-wide SNP association data for the ACTH response in the dex/CRH test, a subset of 14 SNPs was identified that, in conjunction with the SNP rs28373064, can be used for an accurate, sensitive and specific prediction of these phenotypes in patients. Increased ACTH secretion in this test has been linked to a possible increase in central CRH/CRHR1 function. It is surprising that genetic polymorphisms, which act in interaction with genetic variation in the AVPR1B gene, without taking into consideration other factors such as endocrine measures, are suitable predictors of the ACTH response in the dex/CRH test.

These variants may be used to identify patients that may have CRH system hyperactivity when depressed. Patients with depression or anxiety disorders, classified into the high ACTH response group according to the genotypes of the presented 14 SNPs and the SNP rs28373064 will be more likely to respond to CRHR1 antagonist and/or $V_{1B}$ antagonist treatment. This allows an enrichment of such patients for CRHR1 antagonist and/or $V_{1B}$ antagonist treatment studies who should respond to this specific treatment.

TABLE 4

List of 14 SNPs used to predict high vs low ACTH response status allowing for interaction with genetic variation in the AVPR1B gene.

| SNP | Chromosome | Coordinate_HG18 | GeneVariant | P-value for association with ln AUC ACTH in epistasis with genetic variation in AVPR1B | GeneName |
|---|---|---|---|---|---|
| rs9880583 | chr3 | 20980315 | INTERGENIC | 6,31E-005 | N/A |
| rs13099050 | chr3 | 21028194 | INTERGENIC | 4,50E-005 | N/A |
| rs7441352 | chr4 | 55608691 | INTERGENIC | 1,68E-005 | N/A |
| rs730258 | chr4 | 68431265 | INTRONIC | 9,08E-005 | TMPRSS11D |
| rs12654236 | chr5 | 169540125 | INTERGENIC | 9,98E-005 | N/A |
| rs17091872 | chr8 | 19876257 | INTERGENIC | 9,77E-005 | N/A |
| rs12254219 | chr10 | 79113526 | INTERGENIC | 6,05E-005 | N/A |
| rs11575663 | chr10 | 115316093 | INTRONIC | 7,92E-005 | HABP2 |
| rs7080276 | chr10 | 123112960 | INTERGENIC | 8,87E-005 | N/A |
| rs7416 | chr11 | 10485077 | 3PRIME_UTR | 5,61E-005 | AMPD3 |
| rs12424513 | chr12 | 95088085 | INTERGENIC | 4,20E-005 | N/A |
| rs1035050 | chr17 | 44919011 | INTERGENIC | 9,77E-005 | N/A |
| rs9959162 | chr18 | 68100371 | INTERGENIC | 5,57E-005 | N/A |
| rs8088242 | chr18 | 68100758 | INTERGENIC | 6,06E-005 | N/A |

Example 2

Sleep disturbances, such as decreased slow-wave sleep, increased sleep fragmentation and rapid-eye-movement sleep (REMS) disinhibition, are cardinal symptoms of major depression in humans. This study aims to identify those patients where a central CRH hyperdrive plays a causal role and which would therefore respond favourably to a CRHR1 antagonist. To test the relationship between a central CRH-overexpression and REM-disinhibition in particular, transgenic mouse models where CRH is overexpressed as a result of genetic engineering were employed.

Many animal models of depression share increases in REM-sleeps (REMS) as a common feature. Therefore, increased REMS in animals should reflect REMS-disinhibitions in humans. Mice with CNS-specific CRH-overexpression strikingly share the characteristic increases in REMS. As such, an increase in REMS indicates a central hypersecretion of CRH and may serve as a biomarker to identify those patients who would benefit from treatment with a CRHR1 antagonist.

Experiments were conducted with two different mouse lines of excessive central CRH secretion and their respective control littermates (CL). Mice of the CRH-COE$^{CNS}$ line are characterised by CRH-overexpression within the whole CNS, whereas mice of the Cor26 CRH line display a CRH-overexpression specific to CRH-ergic neurons of the CNS. Three different CRHR1 antagonists were tested. While DMP-696 (bicyclic) and CP-316,311 (monocyclic) are class I CRH-R1 antagonists. SSR125543A (long off-rate, typical slow-tight binding inhibitor) belongs to class II CRH-R1 antagonists. DMP-696 and SSR125543A were applied to CRH-COE$^{CNS}$ mice ($n_{DMP696}$=6/6 COE/CL; $n_{SSR125543}$=6/5 COE/CL), while CP-316,311 was tested in Cor26 CRH mice ($n_{CP316,311}$=5/3 Cor26/CL). In all cases, animals were left to recover from EEG/EMG-electrode implantation for two weeks, after which two days of baseline recording were initiated. Treatment with CRH-R1 antagonist or respective vehicle control commenced thereafter for five consecutive days. Antagonists were applied through the drinking water at a daily dose of 50 mg/kg body weight. EEG and EMG recordings were manually scored as wake, non-REMS (NREMS), and REMS in four second epochs by an experienced evaluator.

Figure 2:
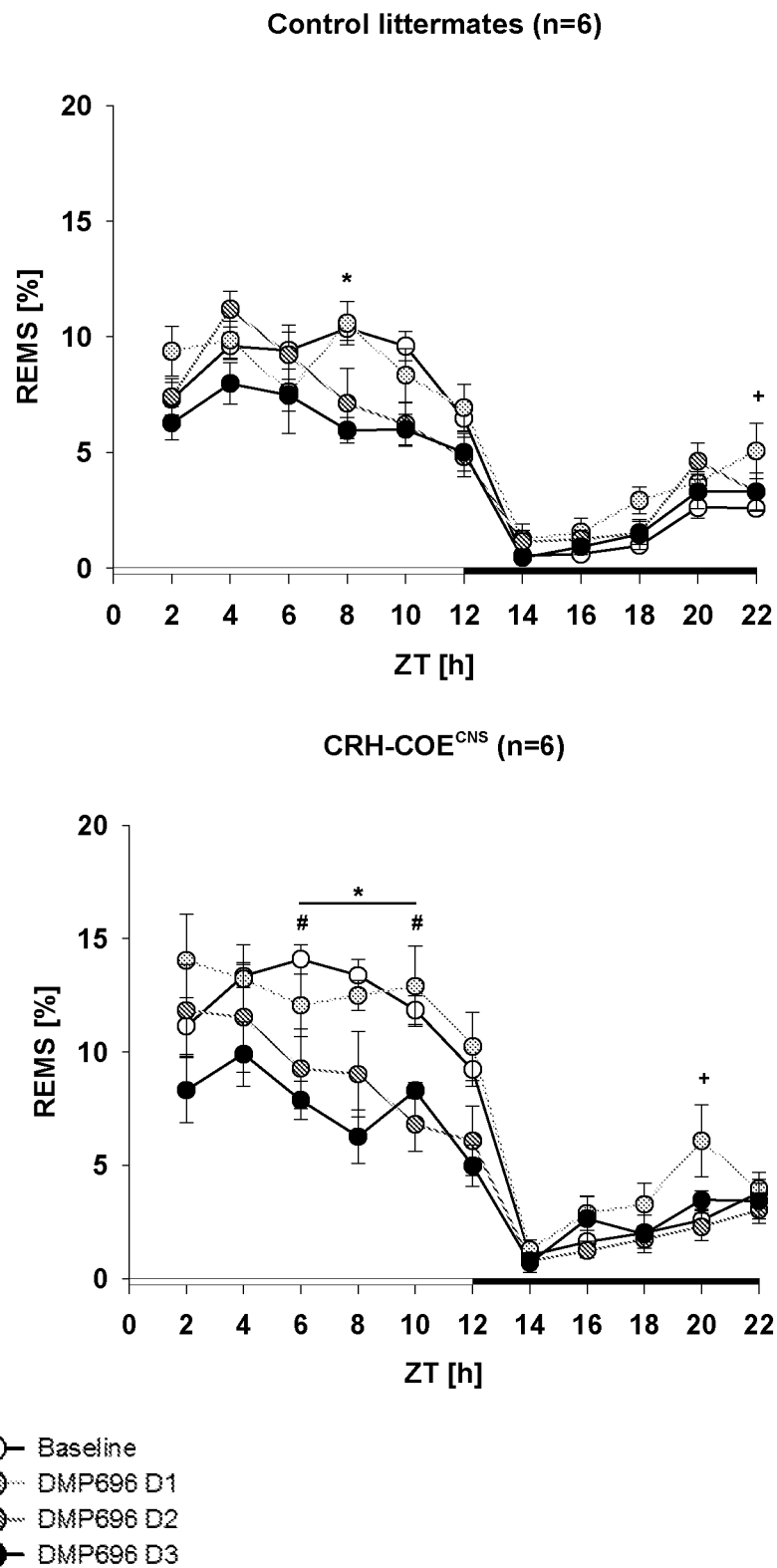
FIG. 2: Increased REMS activity in CRH-COE$^{CNS}$ mice is suppressed by DMP696 (50 mg/kg/d) application via drinking water. Treatment day one, light grey; treatment day 2, dark grey; treatment day three, black. Symbols indicate significant differences between baseline and treatment day one (+), two (#) or three (*). Light and dark bar on the x-axis indicate light and dark period, respectively.

As previously shown, CRH-COE$^{CNS}$ mice display significantly higher REMS activity under baseline condition as compared to controls. Chronic DMP-696 (50 mg/kg/d DMP-696) treatment entails only a mild suppression of REMS in CL mice. However, DMP-696-treated CRH-COE$^{CNS}$ mice show a significant decrease in REMS activity beginning with treatment day two ($P<0.05$). The strongest suppression of REMS activity in CRH-COE$^{CNS}$ animals could be observed on treatment day three (FIG. 2).

Figure 3:
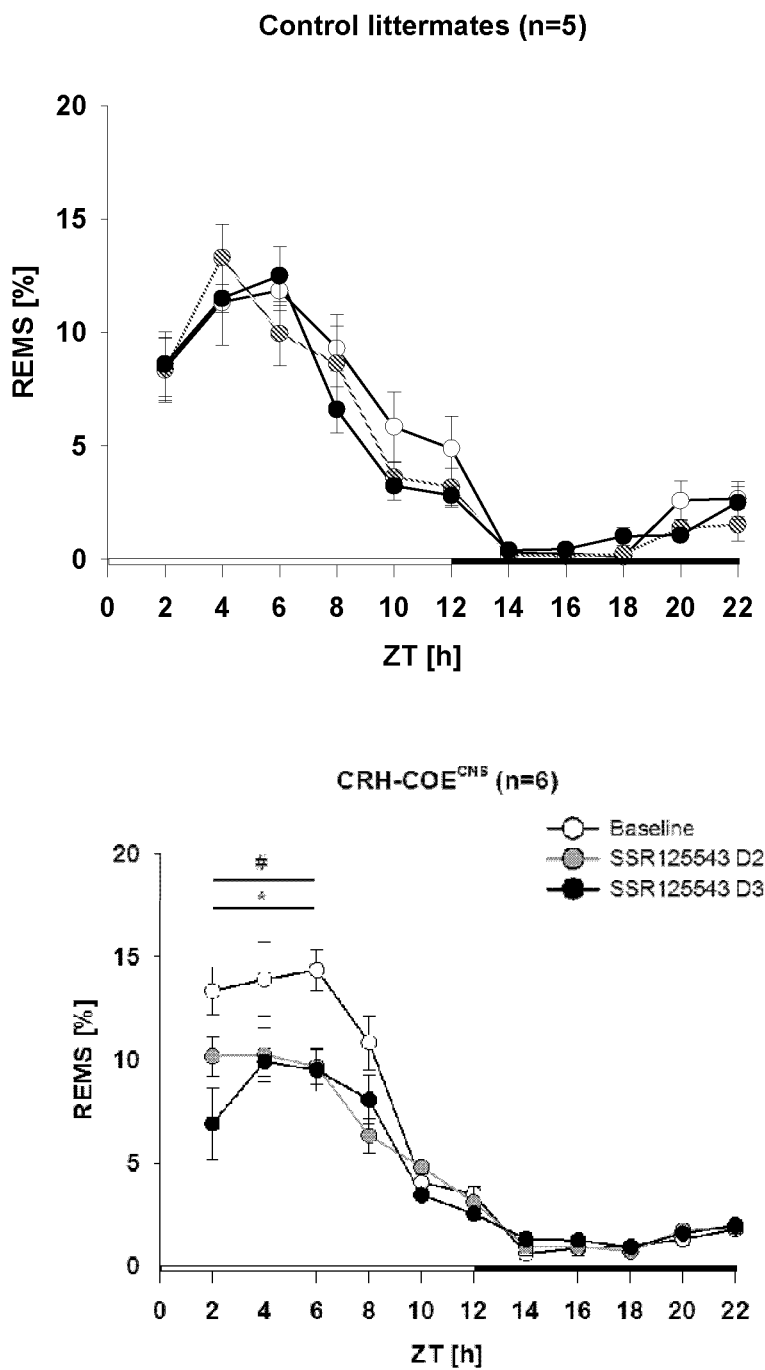
FIG. 3: Increased activity of REMS in CRH-COE$^{CNS}$ is suppressed by application of the CRH-R1 antagonist SSR125543 (50 mg/kg/d) via drinking water. Baseline day, white; treatment day two, dark grey treatment day three, black. Symbols indicate significant differences between baseline and treatment day two (#) or three (*). Light and dark bar on the x-axis indicate light and dark period, respectively.

Comparable to DMP-696 treatment, oral application of SSR125543A (50 mg/kg/d) affected REMS levels in CRH-overexpressing mice. No effects of SSR125543 on REMS activity in control animals could be detected. In contrast, a significant suppression of REMS could be observed beginning with day two in CRH-overexpressing animals ($P\leq0.035$). Similar to DMP-696 treatment, REMS suppression in CRH-COE$^{CNS}$ mice never exceeded baseline REMS-levels of CL (FIG. 3).

Figure 4:
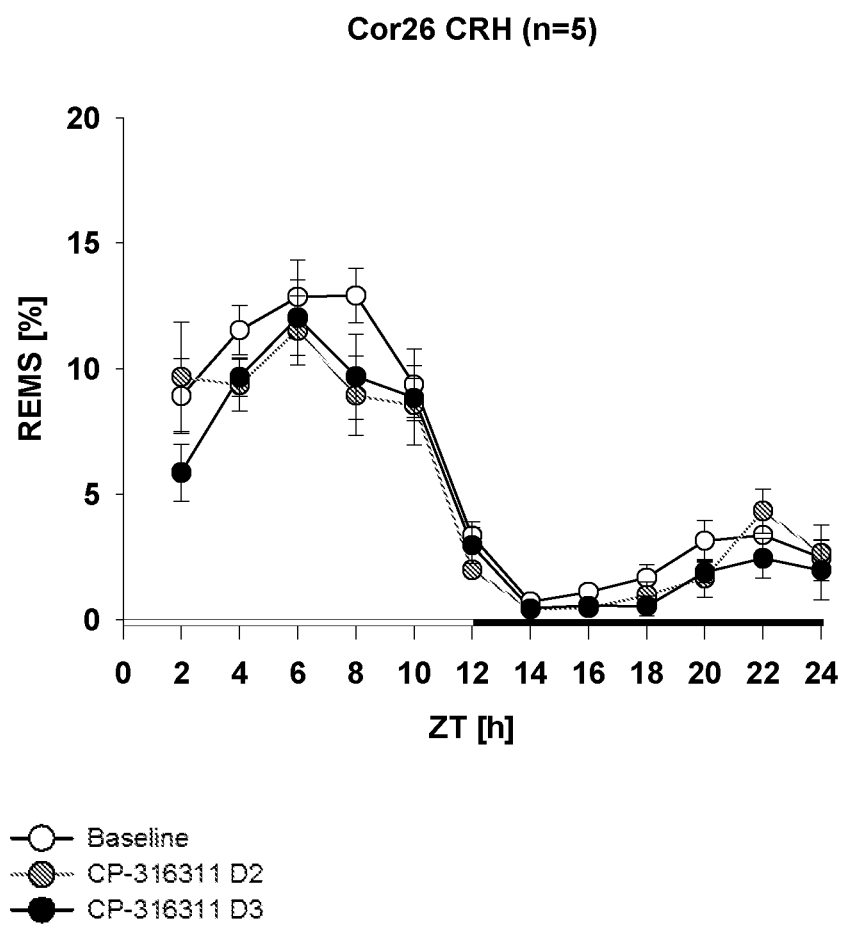
FIG. 4: REMS activity in Cor26 CRH mice is suppressed by application of the CRH-R1 antagonist CP-316311 (50 mg/kg/d) via drinking water. Baseline day, white; treatment day two, dark grey; treatment day three, black.

Application of CP-316,311 (Pfizer) in the Cor26 CRH mouse line showed no significant effect on REMS levels in CL animals. Similarly, in CRH-overexpressing Cor26 CRH mice suppression in REMS apparently seemed weak. However, comparison of the area under the curve (AUC) within the light period of baseline and treatment day three showed a significant decrease ($P=0.006$) of REMS levels after CP-316,311 application (FIG. 4).

CRH is one of the major drivers of the stress response in the brain. Hyperactivity of the CRH system seems to be responsible for cognitive impairments, emotional responses, and behavioural changes which are typical for depression. One of those behavioural changes are sleep disturbances exemplified by REMS disinhibition. The link between CRH-overexpression and REMS level increases is evidenced by the mouse lines used in these experiments. Since CRH-overexpression in the Cor26 CRH mouse line is limited to CRH-ergic neurons, the net increase of CRH is lower when compared to the whole brain overexpression in CRH-COE$^{CNS}$ mice. As a result, the phenotype of increased REMS levels was less profound in Cor26 CRH mice as compared to CRH-COE$^{CNS}$ animals.

A finding of this study is that the normalization of CRH-elicited sleep-EEG disturbances is striking when (1) different chemical classes of CRHR1 antagonists are used and (2) different animal models for CRH-induced sleep-EEG changes that are typical for human depression are employed. REMS disinhibition is indicative of a central CRH dysfuntion (i.e. hyperactivity) and as such may serve as a biomarker for the identification of depressed patients where depression is caused by central CRH-hyperdrive. Normalization of the sleep pattern by application of different CRHR1 antagonists could be shown in all of our experiments, employing different classes of CRHR1 receptors and different animal models overexpressing centrally CRH.

The invention claimed is:

1. A method of treating a human patient with depressive and/or anxiety symptoms comprising
administering an effective amount of a V1B receptor antagonist and/or CRHR1 antagonist to the patient in need thereof,
wherein the patient's genome has a polymorphic variant in the AVPR1B gene, the polymorphic variant is SNP rs28373064 which is represented by a single polymorphic change at position 27 of SEQ ID NO: 1, wherein in one or two alleles of the wild-type nucleotide A is replaced by indicator nucleotide G, or an SNP in strong linkage disequilibrium with SNP rs28373064, and
wherein the patient's genome excluding the AVPR1B gene has at least one polymorphic variant selected from the group of biomarkers consisting of:
SNP rs9880583 which is represented by a single polymorphic change at position 27 of SEQ ID NO: 2, wherein in one or two alleles the wild-type nucleotide C is replaced by indicator nucleotide G,
SNP rs13099050 which is represented by a single polymorphic change at position 27 of SEQ ID NO: 3, wherein in one or two alleles the wild-type nucleotide A is replaced by indicator nucleotide C,
SNP rs7441352 which is represented by a single polymorphic change at position 27 of SEQ ID NO: 4, wherein in one or two alleles the wild-type nucleotide A is replaced by indicator nucleotide G,
SNP rs730258 which is represented by a single polymorphic change at position 27 of SEQ ID NO: 5, wherein in one or two alleles the wild-type nucleotide C is replaced by indicator nucleotide T,
SNP rs12654236 which is represented by a single polymorphic change at position 27 of SEQ ID NO: 6, wherein in one or two alleles the wild-type nucleotide A is replaced by indicator nucleotide G,
SNP rs17091872 which is represented by a single polymorphic change at position 27 of SEQ ID NO: 7, wherein in one or two alleles the wild-type nucleotide A is replaced by indicator nucleotide G, SNP rs12254219 which is represented by a single polymorphic change at position 27 of SEQ ID NO: 8, wherein in one or two alleles the wild-type nucleotide C is replaced by indicator nucleotide T, SNP rs11575663 which is represented by a single polymorphic change at position 27 of SEQ ID NO: 9, wherein in one or two alleles the wild-type nucleotide A is replaced by indicator nucleotide G, SNP rs7080276 which is represented by a single polymorphic change at position 27 of SEQ ID NO: 10, wherein in one or two alleles the wild-type nucleotide A is replaced by indicator nucleotide G, SNP rs7416 which is represented by a single polymorphic change at position 27 of SEQ ID NO: 11, wherein in one or two alleles the wild-type nucleotide A is replaced by indicator nucleotide G, SNP rs12424513 which is represented by a single polymorphic change at position 27 of SEQ ID NO: 12, wherein in one or two alleles the wild-type nucleotide C is replaced by indicator nucleotide T, SNP rs1035050 which is represented by a single polymorphic change at position 27 of SEQ ID NO: 13, wherein in one or two alleles the wild-type nucleotide C is replaced by indicator nucleotide T, SNP rs9959162 which is represented by a single polymorphic change at position 27 of SEQ ID NO: 14, wherein in one or two alleles the wild-type nucleotide A is replaced by indicator nucleotide C, and SNP rs8088242 which is represented by a single polymorphic change at position 27 of SEQ ID NO: 15, wherein in one or two alleles the wild-type nucleotide A is replaced by indicator nucleotide G.

2. The method according to claim 1, wherein the patient's genome excluding the AVPR1B gene has at least two polymorphic variants selected from the group of biomarkers.

3. The method according to claim 1, wherein the method further comprises a step of determining the presence of at least one clinical marker selected from the group consisting of the AVP level, the response to the combined dex/CRH test and the rapid-eye-movement (REM) density.

4. The method according to claim 1, wherein the patient's genome has a polymorphic variant in the AVPR1B gene, the polymorphic variant is SNP rs28373064 which is represented by a single polymorphic change at position 27 of SEQ ID NO: 1, wherein in one or two alleles of the wild-type nucleotide A is replaced by indicator nucleotide G.

5. The method according to claim 1, wherein the combination of the polymorphic variant in the AVPR1B gene with the presence of the at least one polymorphic variant in the patient's genome excluding the AVPR1B gene is indicative for a treatment response.

6. The method of claim 1, wherein the V1B receptor antagonist is selected from the group consisting of SSR149415, Org 52186, ABT-436 and ABT-558.

7. The method according to claim 5, wherein the patient's genome excluding the AVPR1B gene has at least two polymorphic variants selected from the group of biomarkers.

8. The method according to claim 5, wherein the method further comprises a step of determining the presence of at least one clinical marker selected from the group consisting of the AVP level, the response to the combined dex/CRH test and the rapid-eye-movement (REM) density.

9. The method of claim 5, wherein the V1B receptor antagonist is selected from the group consisting of SSR149415, Org 52186, ABT-436 and ABT-558.

10. A method of treating a human patient with depressive and/or anxiety symptoms comprising administering an effective amount of a V1B receptor antagonist and/or CRHR1 antagonist to the patient in need thereof, wherein the patient's genome has a polymorphic variant in the AVPR1B gene, the polymorphic variant is SNP rs28373064 which is represented by a single polymorphic change at position 27 of SEQ ID NO: 1, wherein in one or two alleles of the wild-type nucleotide A is replaced by indicator nucleotide G, or an SNP in strong linkage disequilibrium with SNP rs28373064, and wherein the patient's genome excluding the AVPR1B gene has at least one polymorphic variant selected from the group of biomarkers consisting of:

SNP rs9880583 which is represented by a single polymorphic change at position 27 of SEQ ID NO: 2, wherein in one or two alleles the wild-type nucleotide C is replaced by indicator nucleotide G, or an SNP in strong linkage disequilibrium with SNP rs9880583, SNP rs13099050 which is represented by a single polymorphic change at position 27 of SEQ ID NO: 3, wherein in one or two alleles the wild-type nucleotide A is replaced by indicator nucleotide C, or an SNP in strong linkage disequilibrium with SNP rs13099050, SNP rs7441352 which is represented by a single polymorphic change at position 27 of SEQ ID NO: 4, wherein in one or two alleles the wild-type nucleotide A is replaced by indicator nucleotide G, or an SNP in strong linkage disequilibrium with SNP rs7441352, SNP rs730258 which is represented by a single polymorphic change at position 27 of SEQ ID NO: 5, wherein in one or two alleles the wild-type nucleotide C is replaced by indicator nucleotide T, or an SNP in strong linkage disequilibrium with SNP rs730258, SNP rs12654236 which is represented by a single polymorphic change at position 27 of SEQ ID NO: 6, wherein in one or two alleles the wild-type nucleotide A is replaced by indicator nucleotide G, or an SNP in strong linkage disequilibrium with SNP rs12654236, SNP rs17091872 which is represented by a single polymorphic change at position 27 of SEQ ID NO: 7, wherein in one or two alleles the wild-type nucleotide A is replaced by indicator nucleotide G, or an SNP in strong linkage disequilibrium with SNP rs17091872, SNP rs12254219 which is represented by a single polymorphic change at position 27 of SEQ ID NO: 8, wherein in one or two alleles the wild-type nucleotide C is replaced by indicator nucleotide T, or an SNP in strong linkage disequilibrium with SNP rs12254219, SNP rs11575663 which is represented by a single polymorphic change at position 27 of SEQ ID NO: 9, wherein in one or two alleles the wild-type nucleotide A is replaced by indicator nucleotide G, or an SNP in strong linkage disequilibrium with SNP rs11575663, SNP rs7080276 which is represented by a single polymorphic change at position 27 of SEQ ID NO: 10, wherein in one or two alleles the wild-type nucleotide A is replaced by indicator nucleotide G, or an SNP in strong linkage disequilibrium with SNP rs7080276, SNP rs7416 which is represented by a single polymorphic change at position 27 of SEQ ID NO: 11, wherein in one or two alleles the wild-type nucleotide A is replaced by indicator nucleotide G, or an SNP in strong linkage disequilibrium with SNP rs7416, SNP rs12424513 which is represented by a single polymorphic change at position 27 of SEQ ID NO: 12, wherein in one or two alleles the wild-type nucleotide C is replaced by indicator nucleotide T, or an SNP in strong linkage disequilibrium with SNP rs12424513, SNP rs1035050 which is represented by a single polymorphic change at position 27 of SEQ ID NO: 13, wherein in one or two alleles the wild-type nucleotide C is replaced by indicator nucleotide T, or an SNP in strong linkage disequilibrium with SNP rs1035050, SNP rs9959162 which is represented by a single polymorphic change at position 27 of SEQ ID NO: 14, wherein in one or two alleles the wild-type nucleotide A is replaced by indicator nucleotide C, or an SNP in strong linkage disequilibrium with SNP rs9959162, and SNP rs8088242 which is represented by a single polymorphic change at position 27 of SEQ ID NO: 15, wherein in one or two alleles the wild-type nucleotide A is replaced by indicator nucleotide G, or an SNP in strong linkage disequilibrium with SNP rs8088242.

* * * * *

SEQUENCE LISTING

<160> NUMBER OF SEQ ID NOS: 15

<210> SEQ ID NO 1
<211> LENGTH: 52
<212> TYPE: DNA
<213> ORGANISM: Homo sapiens

<400> SEQUENCE: 1
tcctgcaccg gctagccggc tggcagaggg cgcgccaaca gccgccagcc ga        52

<210> SEQ ID NO 2
<211> LENGTH: 52
<212> TYPE: DNA
<213> ORGANISM: Homo sapiens

<400> SEQUENCE: 2
aaatgaagcc acttgtttct tctccaccta tgacctagac accccctccc ca        52

<210> SEQ ID NO 3
<211> LENGTH: 52
<212> TYPE: DNA
<213> ORGANISM: Homo sapiens

<400> SEQUENCE: 3
aatgaataag aagcctctca agacagaagg attcaacctt atagctttga ta    52

<210> SEQ ID NO 4
<211> LENGTH: 52
<212> TYPE: DNA
<213> ORGANISM: Homo sapiens

<400> SEQUENCE: 4
tcctctcccc ctatctctgc ttttcaacat tgtactggaa gtcctagcta at    52

<210> SEQ ID NO 5
<211> LENGTH: 52
<212> TYPE: DNA
<213> ORGANISM: Homo sapiens

<400> SEQUENCE: 5
agaaataaaa tcatttcata ttcatgcaat agatacaaga aatgtattaa ag    52

<210> SEQ ID NO 6
<211> LENGTH: 52
<212> TYPE: DNA
<213> ORGANISM: Homo sapiens

<400> SEQUENCE: 6
ggactgtttt tgtattcagt gcacagatgt gtgtgaagac acccagcatg tt    52

<210> SEQ ID NO 7
<211> LENGTH: 52
<212> TYPE: DNA
<213> ORGANISM: Homo sapiens

<400> SEQUENCE: 7
aatgcaaatt tttatcaagt acctacaatg tgcgggcaat tttgcaaggt gc    52

<210> SEQ ID NO 8
<211> LENGTH: 52
<212> TYPE: DNA
<213> ORGANISM: Homo sapiens

<400> SEQUENCE: 8
ctgtgtcctt gaagcccatg acagtgcctg acacaaagta gttgctcaat aa    52

<210> SEQ ID NO 9
<211> LENGTH: 52
<212> TYPE: DNA
<213> ORGANISM: Homo sapiens

<400> SEQUENCE: 9
ctttatttac aaaaacaaaa ctgctaagct tggcccaagg gcccttattt gc    52

<210> SEQ ID NO 10
<211> LENGTH: 52
<212> TYPE: DNA
<213> ORGANISM: Homo sapiens

<400> SEQUENCE: 10
gtccacgtga cttcacacat cagccaatga ggtctggcct ctgtcaccaa ac    52

```
<210> SEQ ID NO 11
<211> LENGTH: 52
<212> TYPE: DNA
<213> ORGANISM: Homo sapiens
<220> FEATURE:
<221> NAME/KEY: misc_feature
<222> LOCATION: (21)..(25)
<223> OTHER INFORMATION: n is a, c, g, or t

<400> SEQUENCE: 11
gtaaccggat gcattttttt nnnnnaaaat ttctcccttta tctactatga tg        52

<210> SEQ ID NO 12
<211> LENGTH: 52
<212> TYPE: DNA
<213> ORGANISM: Homo sapiens

<400> SEQUENCE: 12
gcagccggac cctgtattga ggaggacggg cagggaaagc atgctttaga ga        52

<210> SEQ ID NO 13
<211> LENGTH: 52
<212> TYPE: DNA
<213> ORGANISM: Homo sapiens

<400> SEQUENCE: 13
ctccccatct ttgtattgat gtaagcctca cctctctgcc cactggcatc cg        52

<210> SEQ ID NO 14
<211> LENGTH: 52
<212> TYPE: DNA
<213> ORGANISM: Homo sapiens

<400> SEQUENCE: 14
tcctcctgat tgccttcaaa ttaggaaatc agttgaagtt cctgctttca ga        52

<210> SEQ ID NO 15
<211> LENGTH: 52
<212> TYPE: DNA
<213> ORGANISM: Homo sapiens

<400> SEQUENCE: 15
aacatctgac aaaaggtaag aactcaataa atgctttgat agaacttaaa ta        52
```